US012281168B2

(12) United States Patent
Liu et al.

(10) Patent No.: US 12,281,168 B2
(45) Date of Patent: Apr. 22, 2025

(54) BINDING MOLECULE SPECIFIC FOR LIF AND USE THEREOF

(71) Applicant: JACOBIO PHARMACEUTICALS CO., LTD., Beijing (CN)

(72) Inventors: Qinghao Liu, Beijing (CN); Jun Tao, Beijing (CN); Wenlai Zhou, Beijing (CN); Shanshan He, Beijing (CN); Haiyan Yang, Beijing (CN); Hongling Wang, Beijing (CN); Guiqun Yang, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

(21) Appl. No.: 17/407,264

(22) Filed: Aug. 20, 2021

(65) Prior Publication Data

US 2021/0403582 A1 Dec. 30, 2021

Related U.S. Application Data

(63) Continuation of application No. PCT/CN2020/118247, filed on Sep. 28, 2020.

(30) Foreign Application Priority Data

Sep. 29, 2019 (WO) ................ PCT/CN2019/108904
Feb. 27, 2020 (WO) ................ PCT/CN2020/077049

(51) Int. Cl.
| C07K 16/24 | (2006.01) |
| A61P 35/00 | (2006.01) |
| C07K 16/28 | (2006.01) |
| C07K 16/46 | (2006.01) |
| A61K 39/00 | (2006.01) |

(52) U.S. Cl.
CPC .......... *C07K 16/2866* (2013.01); *A61P 35/00* (2018.01); *A61K 2039/505* (2013.01); *C07K 2317/24* (2013.01); *C07K 2317/31* (2013.01); *C07K 2317/55* (2013.01); *C07K 2317/565* (2013.01); *C07K 2317/569* (2013.01); *C07K 2317/622* (2013.01); *C07K 2317/732* (2013.01); *C07K 2317/94* (2013.01)

(58) Field of Classification Search
CPC ................................................ C07K 16/2866
See application file for complete search history.

(56) References Cited

U.S. PATENT DOCUMENTS

| 10,968,273 | B2 | 4/2021 | Suarez et al. | |
| 2006/0115832 | A1* | 6/2006 | Hoon ................... | C12Q 1/6886 435/6.16 |
| 2006/0275844 | A1* | 12/2006 | Linke ..................... | G16H 70/60 702/19 |
| 2008/0280297 | A1* | 11/2008 | Dalla-Favera ... | G01N 33/57426 435/6.16 |
| 2012/0178111 | A1* | 7/2012 | Diamandis ........ | G01N 33/57423 435/7.1 |
| 2018/0243414 | A1 | 8/2018 | Seoane et al. | |

FOREIGN PATENT DOCUMENTS

| CN | 103797031 | 5/2014 |
| JP | 2013523796 | 6/2013 |
| JP | 2019502664 | 1/2019 |
| WO | 2011124566 | 10/2011 |
| WO | 2017089614 | 6/2017 |
| WO | 2018115960 | 6/2018 |
| WO | 2019243893 | 12/2019 |

OTHER PUBLICATIONS

Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Portolano (The Journal of Immunology, vol. 150, No. 3, p. 880-887, 1993) (Year: 1993).*
Beiboer (J. Mol. Biol. (2000) 296:833-849) (Year: 2000).*
Paul (Fundamental Immunology, 3rd Edition, 1993, pp. 292-295) (Year: 1993).*
Schiffman et Al. (The New England Journal of Medicine, Vo. 353, No. 20, p. 2101-2104, 2005) (Year: 2005).*
Cuzick et Al. (The Lancet, vol. 361, p. 296-300, 2003) (Year: 2003).*
Hernandez-Ledesma (Peptides, vol. 30, p. 426-430, 2009) (Year: 2009).*
Baxevanis (Expert Opinion: Drug Discovery, vol. 3, No. 4, p. 441-452, 2008) (Year: 2008).*
Komenaka et Al., Clinics in Dermatology, 2004, vol. 22, p. 251-265 (Year: 2004).*
Evans et Al. (Q. J. Med 1999: 92: 299-307) (Year: 1999).*
Shi Y, Gao W, Lytle NK, Huang P, Yuan X, Dann AM, Ridinger-Saison M, DelGiorno KE, Antal CE, Liang G, Atkins AR. Targeting LIF-mediated paracrine interaction for pancreatic cancer therapy and monitoring. Nature. May 2, 2019;569(7754):131-5.
Peñuelas S, Anido J, Prieto-Sánchez RM, Folch G, Barba I, Cuartas I, Garcia-Dorado D, Poca MA, Sahuquillo J, Baselga J, Seoane J. TGF-β increases glioma-initiating cell self-renewal through the induction of LIF in human glioblastoma. Cancer cell. Apr. 7, 2009;15(4):315-27.
Wu HX, Cheng X, Jing XQ, Ji XP, Chen XZ, Zhang YQ, He YG, Liu K, Ye F, Sun HX, Gao Hj. LIFR promotes tumor angiogenesis by up-regulating IL-8 levels in colorectal cancer. Biochimica et Biophysica Acta (BBA)-Molecular Basis of Disease. Sep. 1, 2018;1864(9):2769-84.

(Continued)

*Primary Examiner* — Michael Allen
(74) *Attorney, Agent, or Firm* — Robin L. Teskin; Baker, Donelson, Bearman, Caldwell & Berkowitz PC

(57) ABSTRACT

Provided is a binding molecule specific for LIF and use thereof. Specifically, provided is an isolated antibody or an antigen-binding fragment thereof that binds to LIF and inhibits the activity of LIF. Also provided are uses of the isolated antibody or the antigen-binding fragment thereof in treatment of diseases.

9 Claims, 15 Drawing Sheets

Specification includes a Sequence Listing.

(56) References Cited

OTHER PUBLICATIONS

McLean, K., Tan, L., Bolland, D.E. et al. Leukemia inhibitory factor functions in parallel with interleukin-6 to promote ovarian cancer growth. Oncogene 38, 1576-1584 (2019). https://doi.org/10.1038/s41388-018-0523-6.
Liu YN, Niu S, Chen WY, Zhang Q, Tao Y, Chen WH, Jiang KC, Chen X, Shi H, Liu A, Li J. Leukemia inhibitory factor promotes castration-resistant prostate cancer and neuroendocrine differentiation by activated ZBTB46. Clinical Cancer Research. Jul. 1, 2019;25(13):4128-40.
Anonymous: "A Phase 1 Multicenter, Open-Label, Dose-Escalation and Dose-Expansion Study to Evaluate the Safety, Pharmacokinetics, Pharmacodynamics, Immunogenicity and Antitumor Activity of MSC-1 in Patients With Advanced Solid Tumors", cinicaltrials.gov, Mar. 30, 2018, 8 pages, XP055648550.
Jeanne Magram et al: "LIF as a novel cancer immunotherapy target: modulating the tumor microenvironment with MSC-1, a humanized anti-LIF monoclonal antibody", Internet citation, Jan. 1, 2018, p. 1, XP002779777.
Xiaoyan Li et al: "LIF promotes tumorigenesis and metastasis of breast cancer through the AKT-mTOR pathway", Oncotarget, Feb. 15, 2014, p. 788, XP055156398.
Borazanci E et al: "Phase I, first-in-human study of MSC-1 (AZD0171), a humanized anti-leukemia inhibitory factor monoclonal antibody, for advanced solid tumors", Esmo Open: Cancer Horizons, vol. 7, No. 4, Aug. 1, 2022, p. 100530, XP093084517.

* cited by examiner

A

Lane 1: Negative control
Lane 2: Full-length LIF protein
Lane 3: Mut3 protein
Lane 4: Mut4 protein

B

BINDING MOLECULE SPECIFIC FOR LIF AND USE THEREOF

CROSS-REFERENCE TO RELATED APPLICATIONS

This application is a continuation application of Int'l Appl. No. PCT/CN2020/118247, filed Sep. 28, 2020, which claims priority to Int'l Appl. No. PCT/CN2020/077049, filed Feb. 27, 2020, and claims priority to Int'l Appl. No. PCT/CN2019/108904, filed Sep. 29, 2019, of which is incorporated herein by reference in its entirety.

SEQUENCE DISCLOSURE

This application includes as part of its disclosure an electronic sequence listing text file named "11584980004201.txt", having a size of 128,467 bytes and created on Sep. 20, 2023, which is hereby incorporated by reference in its entirety.

TECHNICAL FIELD

The invention relates to an isolated antibody or antigen-binding fragment thereof specifically binding to LIF, and the use of the isolated antibody or antigen-binding fragment thereof of the invention, and the treatment method using the isolated antibody or antigen-binding fragment thereof of the invention.

BACKGROUND ART

Leukemia inhibitory factor (LIF) is a member of the IL6 type cytokines, and it has various biological activity including stimulating or inhibiting each of cell proliferation, differentiation and survival [1]. Human LIF protein has 202 amino acids, and it has two receptors on the cell membrane surface, GP130 and LIFR. The LIF protein binds to these two receptors, causing the two receptors to form a heterodimer, thereby activating the downstream signaling pathways, such as MAPK signaling pathway and JAK/STAT signaling pathway [2]. It has reported that overexpression of LIF protein and increased serum levels of LIF protein are correlated with poor prognosis of multiple tumors [3, 4]. LIF is a key regulator of cancer stem cells, plays an important role in stem cell maintenance, self-renewal and pluripotency, etc., and is associated with chemoresistance [5, 6]. In addition, LIF can also promote the growth and metastasis of the tumor [7]. Recent evidence indicates that LIF upregulated JAK-STAT3 signaling pathway via autocrine and paracrine mechanisms in tumors, thereby playing a role of promoting tumor growth and inhibiting immune response [8, 9, 10]. Therefore, LIF is a potential therapeutic target. However, the currently developed treatment method for LIF targets is not optimistic. For example, many literatures report that reducing the expression of LIF protein by RNA interference can inhibit tumor growth [11, 12], but the technique of RNA interference has the weakness of poor targeting, short half-life, poor membrane permeability, and is difficult to make medicine. EC359 is a small molecule inhibitor for LIFR. It can not only inhibit the binding of LIFR to LIF, but also inhibit the binding of OSM, CTF1 and CNTF to LIFR [13]. It is unknown whether these additional inhibitions will lead to additional toxicity, and the small molecule inhibitors specific for LIF protein have not been reported yet. Only one antibody drug targeting LIF protein is currently in clinical development stage, and its relevant safety and efficacy data have not yet been published.

Therefore, more researches are needed to develop drugs and combination therapies for LIF targets.

SUMMARY OF INVENTION

The invention provides an isolated antibody or antigen-binding fragment specifically binding to LIF and the use thereof in the treatment of diseases.

In one respect, the invention provides an isolated antibody or antigen-binding fragment thereof that binds at an epitope represented by an amino acid sequence TYGPDTSGKDVFQKK(SEQ ID NO: 61) of human LIF protein or at an epitope of the corresponding amino acid sequence of a different mammalian species.

In another respect, the invention provides an isolated antibody or antigen-binding fragment thereof, which comprises:
(a) LCDR1 comprising an amino acid sequence selected from a group consisting of SEQ ID NO: 1 or 66, and conservative modifications thereof;
(b) LCDR2 comprising an amino acid sequence selected from a group consisting of SEQ ID NO: 2 or 67, and conservative modifications thereof;
(c) LCDR3 comprising an amino acid sequence selected from a group consisting of SEQ ID NO: 3 or 68, and conservative modifications thereof;
(d) HCDR1 comprising an amino acid sequence selected from a group consisting of SEQ ID NO: 4 or 69, and conservative modifications thereof;
(e) HCDR2 comprising an amino acid sequence selected from a group consisting of SEQ ID NO: 5, 45, or 70, and conservative modifications thereof; and
(f) HCDR3 comprising an amino acid sequence selected from a group consisting of SEQ ID NO: 6 or 71, and conservative modifications thereof.

Optionally, the LCDR1, LCDR2, LCDR3, HCDR1, HCDR2 or HCDR3 has additions, substitutions, deletions and/or insertions of 17 or less amino acids.

In some embodiments, the isolated antibody or antigen-binding fragment thereof comprises:
(a) LCDR1 comprising an amino acid sequence selected from a group consisting of SEQ ID NO: 1, and conservative modifications thereof;
(b) LCDR2 comprising an amino acid sequence selected from a group consisting of SEQ ID NO: 2, and conservative modifications thereof;
(c) LCDR3 comprising an amino acid sequence selected from a group consisting of SEQ ID NO: 3, and conservative modifications thereof;
(d) HCDR1 comprising an amino acid sequence selected from a group consisting of SEQ ID NO: 4, and conservative modifications thereof;
(e) HCDR2 comprising an amino acid sequence selected from a group consisting of SEQ ID NO: 5 or 45, and conservative modifications thereof;
(f) HCDR3 comprising an amino acid sequence selected from a group consisting of SEQ ID NO: 6, and conservative modifications thereof.

Optionally, the LCDR1, LCDR2, LCDR3, HCDR1, HCDR2 or HCDR3 has additions, substitutions, deletions and/or insertions of 17 or less amino acids.

In some embodiments, optionally, the LCDR1, LCDR2, LCDR3, HCDR1, HCDR2 or HCDR3 has additions, substitutions, deletions and/or insertions of 9 or less amino acids.

In some embodiments, optionally, the LCDR1, LCDR2, LCDR3, HCDR1, HCDR2 or HCDR3 has additions, substitutions, deletions and/or insertions of 5 or less amino acids.

In some embodiments, the isolated antibody or antigen-binding fragment thereof comprises:

1) (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 5, and (f) HCDR3 comprising SEQ ID NO: 6;
2) (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 45, and (f) HCDR3 comprising SEQ ID NO: 6; or 3) (a) LCDR1 comprising SEQ ID NO: 66, (b) LCDR2 comprising SEQ ID NO: 67,
(c) LCDR3 comprising SEQ ID NO: 68, (d) HCDR1 comprising SEQ ID NO: 69, (e) HCDR2 comprising SEQ ID NO: 70, and (f) HCDR3 comprising SEQ ID NO: 71.

In some embodiments, the isolated antibody or antigen-binding fragment thereof comprises:

1) (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 5, and (f) HCDR3 comprising SEQ ID NO: 6; or
2) (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 45, and (f) HCDR3 comprising SEQ ID NO: 6.

In some embodiments, the isolated antibody or antigen-binding fragment thereof comprises:

(a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 5, and (f) HCDR3 comprising SEQ ID NO: 6.

In some embodiments, the isolated antibody or antigen-binding fragment thereof comprises:

(a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 45, and (f) HCDR3 comprising SEQ ID NO: 6.

In some embodiments, the isolated antibody or antigen-binding fragment thereof comprises:

(a) LCDR1 comprising SEQ ID NO: 66, (b) LCDR2 comprising SEQ ID NO: 67, (c) LCDR3 comprising SEQ ID NO: 68, (d) HCDR1 comprising SEQ ID NO: 69, (e) HCDR2 comprising SEQ ID NO: 70, and (f) HCDR3 comprising SEQ ID NO: 71.

In some embodiments, the isolated antibody or antigen-binding fragment thereof is a murine antibody or antigen-binding fragment thereof, a chimeric antibody or antigen-binding fragment thereof, a fully human antibody or antigen-binding fragment thereof, or a humanized antibody or antigen-binding fragment thereof.

In some embodiments, the antibody is a humanized antibody comprising a framework region or a framework region variant thereof derived from human antibody.

In some embodiments, the isolated antibody or antigen-binding fragment thereof comprises:

(i) a light chain variable region (VL) comprising an amino acid sequence with at least 85% identity to an amino acid sequence selected from a group consisting of SEQ ID NO: 7, 11, 15, 19, 46, 74 or 82, and conservative modifications thereof; and
(ii) a heavy chain variable region (VH) comprising an amino acid sequence with at least 85% identity to an amino acid sequence selected from a group consisting of SEQ ID NO: 23, 27, 31, 48, 75 or 83, and conservative modifications thereof.

In some embodiments, the isolated antibody or antigen-binding fragment thereof comprises:

(i) a light chain variable region (VL) comprising an amino acid sequence with at least 85% identity to an amino acid sequence selected from a group consisting of SEQ ID NO: 7, 11, 15, 19 or 46, and conservative modifications thereof; and
(ii) a heavy chain variable region (VH) comprising an amino acid sequence with at least 85% identity to an amino acid sequence selected from a group consisting of SEQ ID NO: 23, 27, 31 or 48, and conservative modifications thereof.

In some embodiments, the isolated antibody or antigen-binding fragment thereof comprises:

(i) a light chain variable region (VL) comprising an amino acid sequence with at least 85% identity to an amino acid sequence selected from a group consisting of SEQ ID NO: 7, 11, 15 or 19, and conservative modifications thereof; and
(ii) a heavy chain variable region (VH) comprising an amino acid sequence with at least 85% identity to an amino acid sequence selected from a group consisting of SEQ ID NO: 23, 27 or 31, and conservative modifications thereof.

In some embodiments, the light chain variable region comprises an amino acid sequence with at least 90%, at least 95%, at least 96%, at least 97%, at least 98%, at least 99%, or 100% identity to the light chain variable region selected from (i), and the heavy chain variable region comprises an amino acid sequence with at least 90%, at least 95%, at least 96%, at least 97%, at least 98%, at least 99%, or 100% identity to the heavy chain variable region selected from (ii).

In some embodiments, the isolated antibody or antigen-binding fragment thereof comprises:

1) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 23;
2) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 27;
3) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 31;
4) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 23;
5) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 27;
6) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 31;
7) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 23;
8) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 27;
9) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 31;
10) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 23;
11) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 27;
12) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 31;
13) a light chain variable region (VL) that comprises an amino acid sequence with at least 85% identity to an amino acid sequence of SEQ ID NO: 46, and a heavy chain variable region (VH) that comprises an amino acid sequence with at least 85% identity to an amino acid sequence of SEQ ID NO: 48;
14) a light chain variable region (VL) that comprises an amino acid sequence with at least 85% identity to an amino acid sequence of SEQ ID NO: 74, and a heavy chain variable region (VH) that comprises an amino acid sequence with at least 85% identity to an amino acid sequence of SEQ ID NO: 75; or
15) a light chain variable region (VL) that comprises an amino acid sequence with at least 85% identity to an amino acid sequence of SEQ ID NO: 82, and a heavy chain variable region (VH) that comprises an amino acid sequence with at least 85% identity to an amino acid sequence of SEQ ID NO:83.

In some embodiments, the isolated antibody or antigen-binding fragment thereof comprises:
1) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 23;
2) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 27;
3) a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 31;
4) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 23;
5) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 27;
6) a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 31;
7) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 23;
8) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 27;
9) a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 31;
10) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 23;
11) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 27; or 12) a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 31.

In some embodiments, the isolated antibody or antigen-binding fragment thereof comprises:
a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 23.

In some embodiments, the isolated antibody or antigen-binding fragment thereof comprises:
a light chain variable region (VL) that comprises an amino acid sequence with at least 85% identity to an amino acid sequence of SEQ ID NO: 7, and a heavy chain variable region(VH) that comprises an amino acid sequence with at least 85% identity to an amino acid sequence of SEQ ID NO: 27.

In some embodiments, the isolated antibody or antigen-binding fragment thereof comprises:
a light chain variable region (VL) that comprises an amino acid sequence with at least 85% identity to an amino acid sequence of SEQ ID NO: 7, and a heavy chain variable region (VH) that comprises an amino acid sequence with at least 85% identity to an amino acid sequence of SEQ ID NO: 31.

In some embodiments, the isolated antibody or antigen-binding fragment thereof comprises: a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 23.

In some embodiments, the isolated antibody or antigen-binding fragment thereof comprises:
a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 27.

In some embodiments, the isolated antibody or antigen-binding fragment thereof comprises:
a light chain variable region (VL) that comprises an amino acid sequence with at least 85% identity to an amino acid sequence of SEQ ID NO: 11, and a heavy chain variable region (VH) that comprises an amino acid sequence with at least 85% identity to an amino acid sequence of SEQ ID NO: 31.

In some embodiments, the isolated antibody or antigen-binding fragment thereof comprises:
a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 23.

In some embodiments, the isolated antibody or antigen-binding fragment thereof comprises:
a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 27.

In some embodiments, the isolated antibody or antigen-binding fragment thereof comprises: a light chain variable region (VL) that comprises an amino acid sequence with at least 85% identity to an amino acid sequence of SEQ ID NO: 15, and a heavy chain variable region (VH) that comprises an amino acid sequence with at least 85% identity to an amino acid sequence of SEQ ID NO: 31.

In some embodiments, the isolated antibody or antigen-binding fragment thereof comprises:
a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 23.

In some embodiments, the isolated antibody or antigen-binding fragment thereof comprises:
a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 27.

In some embodiments, the isolated antibody or antigen-binding fragment thereof comprises:
a light chain variable region (VL) that comprises an amino acid sequence with at least 85% identity to an amino acid sequence of SEQ ID NO: 19, and a heavy chain variable region (VH) that comprises an amino acid sequence with at least 85% identity to an amino acid sequence of SEQ ID NO: 31.

In some embodiments, the isolated antibody or antigen-binding fragment thereof comprises:
a light chain variable region (VL) that comprises an amino acid sequence with at least 85% identity to an amino acid sequence of SEQ ID NO: 46, and a heavy chain variable region (VH) that comprises an amino acid sequence with at least 85% identity to an amino acid sequence of SEQ ID NO: 48.

In some embodiments, the isolated antibody or antigen-binding fragment thereof comprises: a light chain variable region (VL) that comprises an amino acid sequence with at least 85% identity to an amino acid sequence of SEQ ID NO: 74, and a heavy chain variable region (VH) that comprises an amino acid sequence with at least 85% identity to an amino acid sequence of SEQ ID NO: 75.

In some embodiments, the isolated antibody or antigen-binding fragment thereof comprises:
a light chain variable region (VL) that comprises an amino acid sequence with at least 85% identity to an amino acid sequence of SEQ ID NO: 82, and a heavy chain variable region (VH) that comprises an amino acid sequence with at least 85% identity to an amino acid sequence of SEQ ID NO:83.

In some embodiments, the light and heavy chain variable region comprise an amino acid sequence with at least 90%, at least 95%, at least 96%, at least 97%, at least 98%, at least 99%, or 100% identity to the light and heavy chain variable region selected from 1)-15), respectively.

In one respect, the invention provides an isolated antibody or antigen-binding fragment thereof comprising a combination of a heavy and a light chain variable region selected from any one of the following (i) to (ii):
  (i) a light chain variable region (VL) comprising LCDR1, LCDR2 and LCDR3 that have the same sequence as any one of SEQ ID NO: 7, 11, 15, 19, 46 or 82; and (ii) a heavy chain variable region (VH) comprising HCDR1, HCDR2 and HCDR3 that have the same sequence as any one of SEQ ID NO: 23, 27, 31, 48 or 83.

In some embodiments, the isolated antibody or antigen-binding fragment thereof comprises a light and a heavy chain, wherein:
  (I) the light chain comprises an amino acid sequence with at least 85% identity to an amino acid sequence selected from a group consisting of SEQ ID NO: 9, 13, 17, 21, 37, 39, 50 or 54, and conservative modifications thereof; and
  (II) the heavy chain comprises an amino acid sequence with at least 85% identity to an amino acid sequence selected from a group consisting of SEQ ID NO: 25, 29, 33, 35, 52 or 56, and conservative modifications thereof.

In some embodiments, the isolated antibody or antigen-binding fragment thereof comprises a light and a heavy chain, wherein:
  (I) the light chain comprises an amino acid sequence with at least 85% identity to an amino acid sequence selected from a group consisting of SEQ ID NO: 9, 13, 17, 21, 37, 39 or 50, and conservative modifications thereof; and
  (II) the heavy chain comprises an amino acid sequence with at least 85% identity to an amino acid sequence selected from a group consisting of SEQ ID NO: 25, 29, 33, 35 or 52, and conservative modifications thereof.

In some embodiments, the isolated antibody or antigen-binding fragment thereof comprises a light and a heavy chain, wherein:
  (I) the light chain comprises an amino acid sequence with at least 85% identity to an amino acid sequence selected from a group consisting of SEQ ID NO: 9, 13, 17 or 21, and conservative modifications thereof; and
  (II) the heavy chain comprises an amino acid sequence with at least 85% identity to an amino acid sequence selected from a group consisting of SEQ ID NO: 25, 29 or 33, and conservative modifications thereof.

In some embodiments, the light chain comprises an amino acid sequence with at least 90%, at least 95%, at least 96%, at least 97%, at least 98%, at least 99%, or 100% identity to an light chain selected from (I), and the heavy chain comprises an amino acid sequence with at least 90%, at least 95%, at least 96%, at least 97%, at least 98%, at least 99%, or 100% identity to an heavy chain selected from (II).

In some embodiments, the isolated antibody or antigen-binding fragment thereof comprises:
  1) a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 25,
  2) a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 29,
  3) a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 33,
  4) a light chain that comprises an amino acid sequence with at least 85% identity to an amino acid sequence of SEQ ID NO: 13, and a heavy chain that comprises an amino acid sequence with at least 85% identity to an amino acid sequence of SEQ ID NO: 25,
  5) a light chain that comprises an amino acid sequence with at least 85% identity to an amino acid sequence of SEQ ID NO: 13, and a heavy chain that comprises an amino acid sequence with at least 85% identity to an amino acid sequence of SEQ ID NO: 29,
  6) a light chain that comprises an amino acid sequence with at least 85% identity to an amino acid sequence of SEQ ID NO: 13, and a heavy chain that comprises an amino acid sequence with at least 85% identity to an amino acid sequence of SEQ ID NO: 33,
  7) a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 25,
  8) a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 29,
  9) a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 33,
  10) a light chain that comprises an amino acid sequence with at least 85% identity to an amino acid sequence of SEQ ID NO: 21, and a heavy chain that comprises an amino acid sequence with at least 85% identity to an amino acid sequence of SEQ ID NO: 25,
  11) a light chain that comprises an amino acid sequence with at least 85% identity to an amino acid sequence of SEQ ID NO: 21, and a heavy chain that comprises an amino acid sequence with at least 85% identity to an amino acid sequence of SEQ ID NO: 29,
  12) a light chain that comprises an amino acid sequence with at least 85% identity to an amino acid sequence of SEQ ID NO: 21, and a heavy chain that comprises an amino acid sequence with at least 85% identity to an amino acid sequence of SEQ ID NO: 33,
  13) a light chain that comprises an amino acid sequence with at least 85% identity to an amino acid sequence of SEQ ID NO: 37, and a heavy chain that comprises an amino acid sequence with at least 85% identity to an amino acid sequence of SEQ ID NO: 35,
  14) a light chain that comprises an amino acid sequence with at least 85% identity to an amino acid sequence of SEQ ID NO: 39, and a heavy chain that comprises an amino acid sequence with at least 85% identity to an amino acid sequence of SEQ ID NO: 35,
  15) a light chain that comprises an amino acid sequence with at least 85% identity to an amino acid sequence of SEQ ID NO: 50, and a heavy chain that comprises an amino acid sequence with at least 85% identity to an amino acid sequence of SEQ ID NO: 52, or
  16) a light chain that comprises an amino acid sequence with at least 85% identity to an amino acid sequence of SEQ ID NO: 54, and a heavy chain that comprises an amino acid sequence with at least 85% identity to an amino acid sequence of SEQ ID NO: 56.

In some embodiments, the light and heavy chain comprise an amino acid sequence with at least 90%, at least 95%, at least 96%, at least 97%, at least 98%, at least 99%, or 100% identity to a light and heavy chain selected from 1)-16), respectively.

In some embodiments, the isolated antibody or antigen-binding fragment thereof comprises:
a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 25.

In some embodiments, the isolated antibody or antigen-binding fragment thereof comprises:
a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 29.

In some embodiments, the isolated antibody or antigen-binding fragment thereof comprises:
a light chain that comprises an amino acid sequence with at least 85% identity to an amino acid sequence of SEQ ID NO: 9, and a heavy chain that comprises an amino acid sequence with at least 85% identity to an amino acid sequence of SEQ ID NO: 33.

In some embodiments, the isolated antibody or antigen-binding fragment thereof comprises:
a light chain that comprises an amino acid sequence with at least 85% identity to an amino acid sequence of SEQ ID NO: 13, and a heavy chain that comprises an amino acid sequence with at least 85% identity to an amino acid sequence of SEQ ID NO: 25.

In some embodiments, the isolated antibody or antigen-binding fragment thereof comprises:
a light chain variable region (VL) that comprises an amino acid sequence with at least amino acid sequence of SEQ ID NO: 13, and a heavy chain that comprises an amino acid sequence with at least 85% identity to an amino acid sequence of SEQ ID NO: 29.

In some embodiments, the isolated antibody or antigen-binding fragment thereof comprises:
a light chain that comprises an amino acid sequence with at least 85% identity to an amino acid sequence of SEQ ID NO: 13, and a heavy chain that comprises an amino acid sequence with at least 85% identity to an amino acid sequence of SEQ ID NO: 33.

In some embodiments, the isolated antibody or antigen-binding fragment thereof comprises:
a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 25.

In some embodiments, the isolated antibody or antigen-binding fragment thereof comprises:
a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 29.

In some embodiments, the isolated antibody or antigen-binding fragment thereof comprises:
a light chain that comprises an amino acid sequence with at least 85% identity to an amino acid sequence of SEQ ID NO: 17, and a heavy chain that comprises an amino acid sequence with at least 85% identity to an amino acid sequence of SEQ ID NO: 33.

In some embodiments, the isolated antibody or antigen-binding fragment thereof comprises:
a light chain variable region (VL) that comprises an amino acid sequence with at least amino acid sequence of SEQ ID NO: 21, and a heavy chain that comprises an amino acid sequence with at least 85% identity to an amino acid sequence of SEQ ID NO: 25.

In some embodiments, the isolated antibody or antigen-binding fragment thereof comprises:
a light chain that comprises an amino acid sequence with at least 85% identity to an amino acid sequence of SEQ ID NO: 21, and a heavy chain that comprises an amino acid sequence with at least 85% identity to an amino acid sequence of SEQ ID NO: 29.

In some embodiments, the isolated antibody or antigen-binding fragment thereof comprises:
a light chain that comprises an amino acid sequence with at least 85% identity to an amino acid sequence of SEQ ID NO: 21, and a heavy chain that comprises an amino acid sequence with at least 85% identity to an amino acid sequence of SEQ ID NO: 33.

In some embodiments, the isolated antibody or antigen-binding fragment thereof comprises:
a light chain that comprises an amino acid sequence with at least 85% identity to an amino acid sequence of SEQ ID NO: 37, and a heavy chain that comprises an amino acid sequence with at least 85% identity to an amino acid sequence of SEQ ID NO: 35.

In some embodiments, the isolated antibody or antigen-binding fragment thereof comprises:
a light chain that comprises an amino acid sequence with at least 85% identity to an amino acid sequence of SEQ ID NO: 39, and a heavy chain that comprises an amino acid sequence with at least 85% identity to an amino acid sequence of SEQ ID NO: 35.

In some embodiments, the isolated antibody or antigen-binding fragment thereof comprises:
a light chain variable region (VL) that comprises an amino acid sequence with at least amino acid sequence of SEQ ID NO: 50, and a heavy chain that comprises an amino acid sequence with at least 85% identity to an amino acid sequence of SEQ ID NO: 52.

In some embodiments, the isolated antibody or antigen-binding fragment thereof comprises:
a light chain that comprises an amino acid sequence with at least 85% identity to an amino acid sequence of SEQ ID NO: 54, and a heavy chain that comprises an amino acid sequence with at least 85% identity to an amino acid sequence of SEQ ID NO: 56.

In another respect, the invention provides an isolated antibody or antigen-binding fragment thereof comprising (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 5, and (f) HCDR3 comprising SEQ ID NO: 6.

In yet another respect, the invention provides an isolated antibody or antigen-binding fragment thereof comprising (a) LCDR1 comprising SEQ ID NO: 1, (b) LCDR2 comprising SEQ ID NO: 2, (c) LCDR3 comprising SEQ ID NO: 3, (d) HCDR1 comprising SEQ ID NO: 4, (e) HCDR2 comprising SEQ ID NO: 45, and (f) HCDR3 comprising SEQ ID NO: 6.

In yet another respect, the invention provides an isolated antibody or antigen-binding fragment thereof comprising a light chain variable region (VL) represented by SEQ ID NO: 7, and a heavy chain variable region (VH) represented by SEQ ID NO: 23.

In yet another respect, the invention provides an isolated antibody or antigen-binding fragment thereof comprising a light chain variable region (VL) represented by SEQ ID NO: 11, and a heavy chain variable region (VH) represented by SEQ ID NO: 31.

In yet another respect, the invention provides an isolated antibody or antigen-binding fragment thereof comprising a light chain variable region (VL) represented by SEQ ID NO: 19, and a heavy chain variable region (VH) represented by SEQ ID NO: 31.

In some embodiments, the isolated antibody is a monoclonal antibody, a chimeric antibody, a humanized antibody, a human engineered antibody, a human antibody, a bispecific antibody, Fv, a single chain antibody (scFv), a Fab, a Fab', a Fab'-SH or a F(ab')2.

In some embodiments, the isolated antibody is an IgG.

In some embodiments, the isolated antibody is an IgG1, IgG2 or IgG4.

In some embodiments, the isolated antibody or antigen-binding fragment thereof is leukemia inhibitory factor (LIF) antagonist.

In some embodiments, the isolated antibody or antigen-binding fragment thereof is capable of inhibiting the expression of LIF and/or blocking the activity of LIF.

In some embodiments, the isolated antibody or antigen-binding fragment thereof is capable of competing or cross competing for binding to LIF.

In yet another respect, the invention provides a nucleotide composition comprising a nucleotide molecule encoding the isolated antibody or antigen-binding fragment thereof of the invention. In some embodiments, the nucleotide molecule is DNA or RNA. In some embodiments, the nucleotide molecule is DNA.

In some embodiments, the nucleotide composition comprises:
  (i) a first nucleic acid molecule comprising DNA encoding a light chain variable region (VL) as represented by an amino acid sequence of SEQ ID NO: 7, 11, 15, 19, 46 or 82; and
  (ii) a second nucleic acid molecule comprising DNA encoding a heavy chain variable region (VH) as represented by an amino acid sequence of SEQ ID NO: 23, 27, 31, 48 or 83.

In some embodiments, the nucleotide composition comprises:
  (i) a first nucleic acid molecule comprising DNA encoding a light chain variable region (VL) as represented by an amino acid sequence of SEQ ID NO: 7, 11, 15, 19 or 46; and
  (ii) a second nucleic acid molecule comprising DNA encoding a heavy chain variable region (VH) as represented by an amino acid sequence of SEQ ID NO: 23, 27, 31 or 48.

In some embodiments, the nucleotide composition comprises:
  (i) a first nucleic acid molecule comprising DNA encoding a light chain variable region (VL) as represented by an amino acid sequence of SEQ ID NO: 7, 11, 15, or 19; and
  (ii) a second nucleic acid molecule comprising DNA encoding a heavy chain variable region (VH) as represented by an amino acid sequence of SEQ ID NO: 23, 27 or 31.

In some embodiments, the first nucleic acid molecule comprises DNA with at least 90%, at least 95%, at least 96%, at least 97%, at least 98%, at least 99% or 100% identity to the first nucleic acid molecule selected from (i); the second nucleic acid molecule comprises DNA with at least 90%, at least 95%, at least 96%, at least 97%, at least 98%, at least 99% or 100% identity to the second nucleic acid molecule selected from (ii).

In some embodiments, the nucleotide composition comprises:
  1) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 23;
  2) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 27;
  3) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 31;
  4) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 23;
  5) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 27;
  6) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 31;
  7) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 23;
  8) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 27;
  9) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 31;
  10) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 23;
11) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 27;
12) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 31;
13) a first nucleic acid molecule comprising DNA encoding a light chain variable region (VL) as represented by an amino acid sequence of SEQ ID NO: 46 and a second nucleic acid molecule comprising DNA encoding a heavy chain variable region (VH) as represented by an amino acid sequence of SEQ ID NO: 48;
14) a first nucleic acid molecule comprising DNA encoding a light chain variable region (VL) as represented by an amino acid sequence of SEQ ID NO: 74 and a second nucleic acid molecule comprising DNA encoding a heavy chain variable region (VH) as represented by an amino acid sequence of SEQ ID NO: 75; or
15) a first nucleic acid molecule comprising DNA encoding a light chain variable region (VL) as represented by an amino acid sequence of SEQ ID NO: 82 and a second nucleic acid molecule comprising DNA encoding a heavy chain variable region (VH) as represented by an amino acid sequence of SEQ ID NO: 83.

In some embodiments, the nucleotide composition comprises:
1) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 23;
2) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 27;
3) a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 31;
4) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 23;
5) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 27;
6) a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 31;
7) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 23;
8) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 27;
9) a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 31;
10) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 23;
11) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 27; or
12) a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 31.

In some embodiments, the nucleotide composition comprises:
a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 23.

In some embodiments, the nucleotide composition comprises:
a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 27.

In some embodiments, the nucleotide composition comprises:
a first nucleic acid molecule comprising DNA encoding a light chain variable region (VL) as represented by an amino acid sequence of SEQ ID NO: 7 and a second nucleic acid molecule comprising DNA encoding a heavy chain variable region (VH) as represented by an amino acid sequence of SEQ ID NO: 31.

In some embodiments, the nucleotide composition comprises:
a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 23.

In some embodiments, the nucleotide composition comprises:
a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 27.

In some embodiments, the nucleotide composition comprises:
a first nucleic acid molecule comprising DNA encoding a light chain variable region (VL) as represented by an amino acid sequence of SEQ ID NO: 11 and a second nucleic acid molecule comprising DNA encoding a heavy chain variable region (VH) as represented by an amino acid sequence of SEQ ID NO: 31.

In some embodiments, the nucleotide composition comprises:
a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 23.

In some embodiments, the nucleotide composition comprises:
a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 27.

In some embodiments, the nucleotide composition comprises:
a first nucleic acid molecule comprising DNA encoding a light chain variable region (VL) as represented by an amino acid sequence of SEQ ID NO: 15 and a second nucleic acid molecule comprising DNA encoding a heavy chain variable region (VH) as represented by an amino acid sequence of SEQ ID NO: 31.

In some embodiments, the nucleotide composition comprises:
a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 23.

In some embodiments, the nucleotide composition comprises:
a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 27.

In some embodiments, the nucleotide composition comprises:
a first nucleic acid molecule comprising DNA encoding a light chain variable region (VL) as represented by an amino acid sequence of SEQ ID NO: 19 and a second nucleic acid molecule comprising DNA encoding a heavy chain variable region (VH) as represented by an amino acid sequence of SEQ ID NO: 31;

In some embodiments, the nucleotide composition comprises:
a first nucleic acid molecule comprising DNA encoding a light chain variable region (VL) as represented by an amino acid sequence of SEQ ID NO: 46 and a second nucleic acid molecule comprising DNA encoding a heavy chain variable region (VH) as represented by an amino acid sequence of SEQ ID NO: 48.

In some embodiments, the nucleotide composition comprises:
a first nucleic acid molecule comprising DNA encoding a light chain variable region (VL) as represented by an amino acid sequence of SEQ ID NO: 74 and a second nucleic acid molecule comprising DNA encoding a heavy chain variable region (VH) as represented by an amino acid sequence of SEQ ID NO: 75.

In some embodiments, the nucleotide composition comprises:
a first nucleic acid molecule comprising DNA encoding a light chain variable region (VL) as represented by an amino acid sequence of SEQ ID NO: 82 and a second nucleic acid molecule comprising DNA encoding a heavy chain variable region (VH) as represented by an amino acid sequence of SEQ ID NO: 83.

In some embodiments, the first nucleic acid sequence and the second nucleic acid sequence comprise a DNA sequence with at least 90%, at least 95%, at least 96%, at least 97%, at least 98%, at least 99% or 100% identity to the first nucleic acid sequence or the second nucleic acid sequence selected from 1)-15), respectively.

In some embodiments, DNA encoding a light chain variable region (VL) as represented by an amino acid sequence of SEQ ID NO: 7 is shown as SEQ ID NO: 8.

In some embodiments, DNA encoding a light chain variable region (VL) as represented by an amino acid sequence of SEQ ID NO: 11 is shown as SEQ ID NO: 12.

In some embodiments, DNA encoding a light chain variable region (VL) as represented by an amino acid sequence of SEQ ID NO: 15 is shown as SEQ ID NO: 16.

In some embodiments, DNA encoding a light chain variable region (VL) as represented by an amino acid sequence of SEQ ID NO: 19 is shown as SEQ ID NO: 20.

In some embodiments, DNA encoding a light chain variable region (VL) as represented by an amino acid sequence of SEQ ID NO: 46 is shown as SEQ ID NO: 47.

In some embodiments, DNA encoding a light chain variable region (VL) as represented by an amino acid sequence of SEQ ID NO: 74 is shown as SEQ ID NO: 76.

In some embodiments, DNA encoding a light chain variable region (VL) as represented by an amino acid sequence of SEQ ID NO: 82 is shown as SEQ ID NO: 72.

In some embodiments, DNA encoding a heavy chain variable region (VH) as represented by an amino acid sequence of SEQ ID NO: 23 is shown as SEQ ID NO: 24.

In some embodiments, DNA encoding a heavy chain variable region (VH) as represented by an amino acid sequence of SEQ ID NO: 27 is shown as SEQ ID NO: 28.

In some embodiments, DNA encoding a heavy chain variable region (VH) as represented by an amino acid sequence of SEQ ID NO: 31 is shown as SEQ ID NO: 32.

In some embodiments, DNA encoding a heavy chain variable region (VH) as represented by an amino acid sequence of SEQ ID NO: 48 is shown as SEQ ID NO: 49.

In some embodiments, DNA encoding a heavy chain variable region (VH) as represented by an amino acid sequence of SEQ ID NO: 75 is shown as SEQ ID NO:

In some embodiments, DNA encoding a heavy chain variable region (VH) as represented by an amino acid sequence of SEQ ID NO: 83 is shown as SEQ ID NO: 73.

In some embodiments, the nucleotide composition comprises:
(I) a first nucleic acid sequence comprising DNA encoding a light chain as represented by an amino acid sequence of SEQ ID NO: 9, 13, 17, 21, 37, 39, 50 or 54; and
(II) a second nucleic acid sequence comprising DNA encoding a heavy chain as represented by an amino acid sequence of SEQ ID NO: 25, 29, 33, 35, 52 or 56.

In some embodiments, the nucleotide composition comprises:
(I) a first nucleic acid molecule comprising DNA encoding a light chain as represented by an amino acid sequence of SEQ ID NO: 9, 13, 17, 21, 37, 39 or 50; and
(II) a second nucleic acid molecule comprising DNA encoding a heavy chain as represented by an amino acid sequence of SEQ ID NO: 25, 29, 33, 35 or 52.

In some embodiments, the nucleotide composition comprises:
(I) a first nucleic acid molecule comprising DNA encoding a light chain as represented by an amino acid sequence of SEQ ID NO: 9, 13, 17 or 21; and
(II) a second nucleic acid molecule comprising DNA encoding a heavy chain as represented by an amino acid sequence of SEQ ID NO: 25, 29 or 33.

In some embodiments, the first nucleic acid molecule comprises DNA with at least 90%, at least 95%, at least 96%, at least 97%, at least 98%, at least 99% or 100% identity to the first nucleic acid molecule selected from (I); the second nucleic acid molecule comprises DNA with at least 90%, at least 95%, at least 96%, at least 97%, at least 98%, at least 99%, or 100% identity to the second nucleic acid molecule selected from (II).

In some embodiments, the nucleotide composition comprises:
1) a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 25;
2) a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 29;
3) a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 33;
4) a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 25;
5) a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 29;
6) a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 33;
7) a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 25;
8) a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 29;
9) a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 33;
10) a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 25;
11) a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 29;
12) a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 33;
13) a first nucleic acid molecule comprising DNA encoding a light chain as represented by an amino acid sequence of SEQ ID NO: 37 and a second nucleic acid molecule comprising DNA encoding a heavy chain as represented by an amino acid sequence of SEQ ID NO: 35;
14) a first nucleic acid molecule comprising DNA encoding a light chain as represented by an amino acid sequence of SEQ ID NO: 39 and a second nucleic acid molecule comprising DNA encoding a heavy chain as represented by an amino acid sequence of SEQ ID NO: 35;
15) a first nucleic acid molecule comprising DNA encoding a light chain as represented by an amino acid sequence of SEQ ID NO: 50 and a second nucleic acid molecule comprising DNA encoding a heavy chain as represented by an amino acid sequence of SEQ ID NO: 52; or
16) a first nucleic acid molecule comprising DNA encoding a light chain as represented by an amino acid sequence of SEQ ID NO: 54 and a second nucleic acid molecule comprising DNA encoding a heavy chain as represented by an amino acid sequence of SEQ ID NO: 56.

In some embodiments, the first nucleic acid molecule and the second nucleic acid molecule comprise DNA with at least 90%, at least 95%, at least 96%, at least 97%, at least 98%, at least 99% or 100% identity to the first nucleic acid molecule or the second nucleic acid molecule selected from 1)-16).

In some embodiments, the nucleotide composition comprises:
a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 25.

In some embodiments, the nucleotide composition comprises:
a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 29.

In some embodiments, the nucleotide composition comprises:
a first nucleic acid molecule comprising DNA encoding a light chain as represented by an amino acid sequence of SEQ ID NO: 9 and a second nucleic acid molecule comprising DNA encoding a heavy chain as represented by an amino acid sequence of SEQ ID NO: 33.

In some embodiments, the nucleotide composition comprises:
a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 25.

In some embodiments, the nucleotide composition comprises:
a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 29.

In some embodiments, the nucleotide composition comprises:
a first nucleic acid molecule comprising DNA encoding a light chain as represented by an amino acid sequence of SEQ ID NO: 13 and a second nucleic acid molecule comprising DNA encoding a heavy chain as represented by an amino acid sequence of SEQ ID NO: 33.

In some embodiments, the nucleotide composition comprises:
a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 25.

In some embodiments, the nucleotide composition comprises:
a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 29.

In some embodiments, the nucleotide composition comprises:
a first nucleic acid molecule comprising DNA encoding a light chain as represented by an amino acid sequence of SEQ ID NO: 17 and a second nucleic acid molecule comprising DNA encoding a heavy chain as represented by an amino acid sequence of SEQ ID NO: 33.

In some embodiments, the nucleotide composition comprises:
a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 25.

In some embodiments, the nucleotide composition comprises:
a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 29.

In some embodiments, the nucleotide composition comprises:
a first nucleic acid molecule comprising DNA encoding a light chain as represented by an amino acid sequence of SEQ ID NO: 21 and a second nucleic acid molecule comprising DNA encoding a heavy chain as represented by an amino acid sequence of SEQ ID NO: 33.

In some embodiments, the nucleotide composition comprises:
a first nucleic acid molecule comprising DNA encoding a light chain as represented by an amino acid sequence of SEQ ID NO: 37 and a second nucleic acid molecule comprising DNA encoding a heavy chain as represented by an amino acid sequence of SEQ ID NO: 35.

In some embodiments, the nucleotide composition comprises:
a first nucleic acid molecule comprising DNA encoding a light chain as represented by an amino acid sequence of SEQ ID NO: 39 and a second nucleic acid molecule comprising DNA encoding a heavy chain as represented by an amino acid sequence of SEQ ID NO: 35.

In some embodiments, the nucleotide composition comprises:
a first nucleic acid molecule comprising DNA encoding a light chain as represented by an amino acid sequence of SEQ ID NO: 50 and a second nucleic acid molecule comprising DNA encoding a heavy chain as represented by an amino acid sequence of SEQ ID NO: 52.

In some embodiments, the nucleotide composition comprises:
a first nucleic acid molecule comprising DNA encoding a light chain as represented by an amino acid sequence of SEQ ID NO: 54 and a second nucleic acid molecule comprising DNA encoding a heavy chain as represented by an amino acid sequence of SEQ ID NO: 56.

In some embodiments, DNA encoding a light chain as represented by an amino acid sequence of SEQ ID NO: 9 is shown as SEQ ID NO: 10.

In some embodiments, DNA encoding a light chain as represented by an amino acid sequence of SEQ ID NO: 13 is shown as SEQ ID NO: 14.

In some embodiments, DNA encoding a light chain as represented by an amino acid sequence of SEQ ID NO: 17 is shown as SEQ ID NO: 18.

In some embodiments, DNA encoding a light chain as represented by an amino acid sequence of SEQ ID NO: 21 is shown as SEQ ID NO: 22.

In some embodiments, DNA encoding a light chain as represented by an amino acid sequence of SEQ ID NO: 37 is shown as SEQ ID NO: 38.

In some embodiments, DNA encoding a light chain as represented by an amino acid sequence of SEQ ID NO: 39 is shown as SEQ ID NO: 40.

In some embodiments, DNA encoding a light chain as represented by an amino acid sequence of SEQ ID NO: 50 is shown as SEQ ID NO: 51.

In some embodiments, DNA encoding a light chain as represented by an amino acid sequence of SEQ ID NO: 54 is shown as SEQ ID NO: 55.

In some embodiments, DNA encoding a heavy chain as represented by an amino acid sequence of SEQ ID NO: 25 is shown as SEQ ID NO: 26.

In some embodiments, DNA encoding a heavy chain as represented by an amino acid sequence of SEQ ID NO: 29 is shown as SEQ ID NO: 30.

In some embodiments, DNA encoding a heavy chain as represented by an amino acid sequence of SEQ ID NO: 33 is shown as SEQ ID NO: 34.

In some embodiments, DNA encoding a heavy chain as represented by an amino acid sequence of SEQ ID NO: 35 is shown as SEQ ID NO: 36.

In some embodiments, DNA encoding a heavy chain as represented by an amino acid sequence of SEQ ID NO: 52 is shown as SEQ ID NO: 53.

In some embodiments, DNA encoding a heavy chain as represented by an amino acid sequence of SEQ ID NO: 56 is shown as SEQ ID NO: 57.

In yet another respect, the invention provides a vector comprising the nucleotide composition of the invention.

In some embodiments, the vector is a eukaryotic expression vector, a prokaryotic expression vector or a viral vector.

In yet another respect, the invention provides a host cell comprising the vector of the invention.

In some embodiments, the host cell comprising the vector is obtained by vector transformation.

In some embodiments, the host cell is bacteria, yeast or mammalian cell.

In some embodiments, the host cell is *Escherichia coli*, pichia yeast, Chinese hamster ovary cells or human embryonic kidney 293 cells.

In yet another respect, the invention provides a method of preparing the antibody or antigen-binding fragment thereof of the invention, comprising expressing the antibody or antigen-binding fragment thereof in the host cell of the invention and isolating the antibody or antigen-binding fragment thereof.

In yet another respect, the invention provides a pharmaceutical composition comprising a therapeutically effective amount of the above-mentioned isolated antibody or antigen-binding fragment thereof, and a pharmaceutical acceptable excipient.

In yet another respect, the invention provides a reagent for detecting LIF in biological samples comprising the above-mentioned isolated antibody or antigen-binding fragment thereof.

In some embodiments, the biological samples are blood, serum, urine, biopsy materials, tumor, or any tissues suspected of having abnormal LIF levels.

In another respect, the invention provides a method for inhibiting the expression of LIF and/or blocking the activity of LIF, comprising administering to the patient in need thereof a therapeutically effective amount of the above-mentioned isolated antibody or antigen-binding fragment thereof, and/or the above-mentioned pharmaceutical composition.

In yet another respect, the invention provides use of the above-mentioned isolated antibody or antigen-binding fragment thereof, and/or the above-mentioned pharmaceutical composition in manufacture of a medicament used for inhibiting the expression of LIF and/or blocking the activity of LIF.

In yet another respect, the invention provides the above-mentioned isolated antibody or antigen-binding fragment thereof and/or the above-mentioned pharmaceutical composition for use in inhibiting the expression of LIF and/or blocking the activity of LIF.

In another respect, the invention provides a method for treating a disease or condition related to LIF comprising administering to the patient in need a therapeutically effective amount of the above-mentioned isolated antibody or antigen-binding fragment, and/or the above-mentioned pharmaceutical composition. In some embodiments, the disease or condition related to LIF is tumor. In some embodiments, the tumor is solid tumor. In some embodiments, the solid tumor comprises glioblastoma, lung cancer, ovarian cancer, colorectal cancer, pancreatic cancer or prostate cancer.

In yet another respect, the invention provides use of the above-mentioned isolated antibody or antigen-binding fragment thereof, and/or the above-mentioned pharmaceutical composition in manufacture of a medicament for treating a disease or condition related to LIF. In some embodiments, the disease or condition related to LIF is tumor. In some embodiments, the tumor is solid tumor. In some embodiments, the solid tumor comprises glioblastoma, lung cancer, ovarian cancer, colorectal cancer, pancreatic cancer or prostate cancer.

In yet another respect, the invention provides the above-mentioned isolated antibody or antigen-binding fragment thereof, and/or the above-mentioned pharmaceutical composition for use in treating a disease or condition related to LIF. In some embodiments, the disease related to LIF is tumor. In some embodiments, the tumor is solid tumor. In some embodiments, the solid tumor comprises glioblastoma, lung cancer, ovarian cancer, colorectal cancer, pancreatic cancer or prostate cancer.

A disease or condition related to LIF means that blocking LIF and LIRR and/or GP130 can treat, alleviate, relieve and/or stabilize the disease or condition.

In another respect, the invention provides a method for detecting the LIF in biological samples comprising (i) obtaining a subject's tissue or liquid sample, (ii) exposing the tissue or liquid sample to the above-mentioned isolated antibody or antigen-binding fragment thereof or the above-mentioned reagent; and (iii) comparing the LIF binding to the tissue or liquid sample of (ii) with the LIF binding to a control sample, wherein the increase in the amount of the bound LIF compared with the control sample shows the abnormal level of LIF production, expression or activation.

In some embodiments, the tissue or liquid sample comprises blood, serum, urine, biopsy materials, tumor, or any tissues suspected of having abnormal LIF levels.

TABLE I

Description of the antibody sequence of the invention

| Sequence No. | Sequence |
|---|---|
| SEQ ID NO: 1 (LCDR1 aa of 38E10E1C11, humanized anti-LIF antibody or 38E Chimeric) | RASENIYSYLA |

TABLE I-continued

Description of the antibody sequence of the invention

| Sequence No. | Sequence |
| --- | --- |
| SEQ ID NO: 2 (LCDR2 aa of 38E10E1C11, humanized anti-LIF antibody or 38E Chimeric) | NAKTLAE |
| SEQ ID NO: 3 (LCDR3 aa of 38E10E1C11, humanized anti-LIF antibody or 38E Chimeric) | QHHYVTPLT |
| SEQ ID NO: 4 (HCDR1 aa of 38E10E1C11, humanized anti-LIF antibody or 38E Chimeric) | SYAMS |
| SEQ ID NO: 5 (HCDR2 aa of humanized anti-LIF antibody) | TISSGGSNTYSPDTVKG |
| SEQ ID NO: 6 (HCDR3 aa of 38E10E1C11, humanized anti-LIF antibody or 38E Chimeric) | YYGYYFDF |
| SEQ ID NO: 7 (VL1, aa) | DIQMTQSPSSLSASVGDRVTITCRASENIYSYLAWYQQK PGKSPKLLVYNAKTLAEGVPSRFSGSGSGTDFTLTISSLQ PEDFATYYCQHHYVTPLTFGQGTKLEIKR |
| SEQ ID NO: 8 (VL1, nt) | GACATCCAGATGACCCAGAGCCCCAGCAGCCTGAGC GCCAGCGTGGGCGACAGGGTGACCATCACCTGCAGG GCCAGCGAGAACATCTACAGCTACCTGGCCTGGTACC AGCAGAAGCCCGGCAAGAGCCCCAAGCTGCTGGTGT ACAACGCCAAGACCCTGGCCGAGGGCGTGCCCAGCA GGTTCAGCGGCAGCGGCAGCGGCACCGACTTCACCCT GACCATCAGCAGCCTGCAGCCCGAGGACTTCGCCACC TACTACTGCCAGCACCACTACGTGACCCCCCTGACCT TCGGCCAGGGCACCAAGCTGGAGATCAAGAGG |
| SEQ ID NO: 9 (full light chain 1, aa) | DIQMTQSPSSLSASVGDRVTITCRASENIYSYLAWYQQK PGKSPKLLVYNAKTLAEGVPSRFSGSGSGTDFTLTISSLQ PEDFATYYCQHHYVTPLTFGQGTKLEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| SEQ ID NO: 10 (full light chain 1, nt) | GACATCCAGATGACCCAGAGCCCCAGCAGCCTGAGC GCCAGCGTGGGCGACAGGGTGACCATCACCTGCAGG GCCAGCGAGAACATCTACAGCTACCTGGCCTGGTACC AGCAGAAGCCCGGCAAGAGCCCCAAGCTGCTGGTGT ACAACGCCAAGACCCTGGCCGAGGGCGTGCCCAGCA GGTTCAGCGGCAGCGGCAGCGGCACCGACTTCACCCT GACCATCAGCAGCCTGCAGCCCGAGGACTTCGCCACC TACTACTGCCAGCACCACTACGTGACCCCCCTGACCT TCGGCCAGGGCACCAAGCTGGAGATCAAGAGGACCG TGGCCGCCCCCAGCGTGTTCATCTTCCCCCCCAGCGA CGAGCAGCTGAAGAGCGGCACCGCCAGCGTGGTGTG CCTGCTGAACAACTTCTACCCCAGGGAGGCCAAGGTG CAGTGGAAGGTGGACAACGCCCTGCAGAGCGGCAAC AGCCAGGAGAGCGTGACCGAGCAGGACAGCAAGGAC AGCACCTACAGCCTGAGCAGCACCCTGACCCTGAGC AAGGCCGACTACGAGAAGCACAAGGTGTACGCCTGC GAGGTGACCCACCAGGGCCTGAGCAGCCCCGTGACC AAGAGCTTCAACAGGGGCGAGTGC |
| SEQ ID NO: 11 (VL2, aa) | DIHMTQSPSSLSASVGDRVTITCRASENIYSYLAWYQQK PGKSPKLLVYNAKTLAEGVPSRFSGSGSGTDFTLTISSLQ PEDFATYYCQHHYVTPLTFGQGTKLEIKR |
| SEQ ID NO: 12 (VL2, nt) | GACATCCACATGACCCAGAGCCCCAGCAGCCTGAGC GCCAGCGTGGGCGACAGGGTGACCATCACCTGCAGG GCCAGCGAGAACATCTACAGCTACCTGGCCTGGTACC AGCAGAAGCCCGGCAAGAGCCCCAAGCTGCTGGTGT ACAACGCCAAGACCCTGGCCGAGGGCGTGCCCAGCA GGTTCAGCGGCAGCGGCAGCGGCACCGACTTCACCCT GACCATCAGCAGCCTGCAGCCCGAGGACTTCGCCACC |

TABLE I-continued

Description of the antibody sequence of the invention

| Sequence No. | Sequence |
|---|---|
| | TACTACTGCCAGCACCACTACGTGACCCCCCTGACCT<br>TCGGCCAGGGCACCAAGCTGGAGATCAAGAGG |
| SEQ ID NO: 13 (full light chain 2, aa) | DIHMTQSPSSLSASVGDRVTITCRASENIYSYLAWYQQK<br>PGKSPKLLVYNAKTLAEGVPSRFSGSGSGTDFTLTISSLQ<br>PEDFATYYCQHHYVTPLTFGQGTKLEIKRTVAAPSVFIF<br>PPSDEQLKSGTASVVCLLNNFYPREAKVQWKVDNALQ<br>SGNSQESVTEQDSKDSTYSLSSTLTLSKADYEKHKVYA<br>CEVTHQGLSSPVTKSFNRGEC |
| SEQ ID NO: 14 (full light chain 2, nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCCCGGCAAGAGCCCCAAGCTGCTGGTGT<br>ACAACGCCAAGACCCTGGCCGAGGGCGTGCCCAGCA<br>GGTTCAGCGGCAGCGGCAGCGGCACCGACTTCACCCT<br>GACCATCAGCAGCCTGCAGCCCGAGGACTTCGCCACC<br>TACTACTGCCAGCACCACTACGTGACCCCCCTGACCT<br>TCGGCCAGGGCACCAAGCTGGAGATCAAGAGGACCG<br>TGGCCGCCCCCAGCGTGTTCATCTTCCCCCCCAGCGA<br>CGAGCAGCTGAAGAGCGGCACCGCCAGCGTGGTGTG<br>CCTGCTGAACAACTTCTACCCCAGGGAGGCCAAGGTG<br>CAGTGGAAGGTGGACAACGCCCTGCAGAGCGGCAAC<br>AGCCAGGAGAGCGTGACCGAGCAGGACAGCAAGGAC<br>AGCACCTACAGCCTGAGCAGCACCCTGACCCTGAGC<br>AAGGCCGACTACGAGAAGCACAAGGTGTACGCCTGC<br>GAGGTGACCCACCAGGGCCTGAGCAGCCCCGTGACC<br>AAGAGCTTCAACAGGGGCGAGTGC |
| SEQ ID NO: 15 (VL3, aa) | DIHMTQSPSSLSASVGDRVTITCRASENIYSYLAWYQQK<br>PGKSPQLLVYNAKTLAEGVPSRFSGSGSGTQFTLTISSLQ<br>PEDFATYYCQHHYVTPLTFGQGTKLEIKR |
| SEQ ID NO: 16 (VL3, nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCCCGGCAAGAGCCCCCAGCTGCTGGTGT<br>ACAACGCCAAGACCCTGGCCGAGGGCGTGCCCAGCA<br>GGTTCAGCGGCAGCGGCAGCGGCACCCAGTTCACCCT<br>GACCATCAGCAGCCTGCAGCCCGAGGACTTCGCCACC<br>TACTACTGCCAGCACCACTACGTGACCCCCCTGACCT<br>TCGGCCAGGGCACCAAGCTGGAGATCAAGAGG |
| SEQ ID NO: 17 (full light chain 3, aa) | DIHMTQSPSSLSASVGDRVTITCRASENIYSYLAWYQQK<br>PGKSPQLLVYNAKTLAEGVPSRFSGSGSGTQFTLTISSLQ<br>PEDFATYYCQHHYVTPLTFGQGTKLEIKRTVAAPSVFIF<br>PPSDEQLKSGTASVVCLLNNFYPREAKVQWKVDNALQ<br>SGNSQESVTEQDSKDSTYSLSSTLTLSKADYEKHKVYA<br>CEVTHQGLSSPVTKSFNRGEC |
| SEQ ID NO: 18 (full light chain 3, nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCCCGGCAAGAGCCCCCAGCTGCTGGTGT<br>ACAACGCCAAGACCCTGGCCGAGGGCGTGCCCAGCA<br>GGTTCAGCGGCAGCGGCAGCGGCACCCAGTTCACCCT<br>GACCATCAGCAGCCTGCAGCCCGAGGACTTCGCCACC<br>TACTACTGCCAGCACCACTACGTGACCCCCCTGACCT<br>TCGGCCAGGGCACCAAGCTGGAGATCAAGAGGACCG<br>TGGCCGCCCCCAGCGTGTTCATCTTCCCCCCCAGCGA<br>CGAGCAGCTGAAGAGCGGCACCGCCAGCGTGGTGTG<br>CCTGCTGAACAACTTCTACCCCAGGGAGGCCAAGGTG<br>CAGTGGAAGGTGGACAACGCCCTGCAGAGCGGCAAC<br>AGCCAGGAGAGCGTGACCGAGCAGGACAGCAAGGAC<br>AGCACCTACAGCCTGAGCAGCACCCTGACCCTGAGC<br>AAGGCCGACTACGAGAAGCACAAGGTGTACGCCTGC<br>GAGGTGACCCACCAGGGCCTGAGCAGCCCCGTGACC<br>AAGAGCTTCAACAGGGGCGAGTGC |
| SEQ ID NO: 19 (VL4, aa) | DIHMTQSPSSLSASVGDRVTITCRASENIYSYLAWYQQK<br>QGKSPQLLVYNAKTLAEGVPSRFSGSGSGTQFTLKINSL<br>QPEDFATYYCQHHYVTPLTFGQGTKLEIKR |
| SEQ ID NO: 20 (VL4, nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC |

TABLE I-continued

Description of the antibody sequence of the invention

| Sequence No. | Sequence |
|---|---|
| | AGCAGAAGCAGGGCAAGAGCCCCCAGCTGCTGGTGT<br>ACAACGCCAAGACCCTGGCCGAGGGCGTGCCCAGCA<br>GGTTCAGCGGCAGCGGCAGCGGCACCCAGTTCACCCT<br>GAAGATCAACAGCCTGCAGCCCGAGGACTTCGCCAC<br>CTACTACTGCCAGCACCACTACGTGACCCCCCTGACC<br>TTCGGCCAGGGCACCAAGCTGGAGATCAAGAGG |
| SEQ ID NO: 21(full light<br>chain 4, aa) | DIHMTQSPSSLSASVGDRVTITCRASENIYSYLAWYQQK<br>QGKSPQLLVYNAKTLAEGVPSRFSGSGSGTQFTLKINSL<br>QPEDFATYYCQHHYVTPLTFGQGTKLEIKRTVAAPSVFI<br>FPPSDEQLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC |
| SEQ ID NO: 22(full light<br>chain 4, nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCAGGGCAAGAGCCCCCAGCTGCTGGTGT<br>ACAACGCCAAGACCCTGGCCGAGGGCGTGCCCAGCA<br>GGTTCAGCGGCAGCGGCAGCGGCACCCAGTTCACCCT<br>GAAGATCAACAGCCTGCAGCCCGAGGACTTCGCCAC<br>CTACTACTGCCAGCACCACTACGTGACCCCCCTGACC<br>TTCGGCCAGGGCACCAAGCTGGAGATCAAGAGGACC<br>GTGGCCGCCCCCAGCGTGTTCATCTTCCCCCCCAGCG<br>ACGAGCAGCTGAAGAGCGGCACCGCCAGCGTGGTGT<br>GCCTGCTGAACAACTTCTACCCCAGGGAGGCCAAGGT<br>GCAGTGGAAGGTGGACAACGCCCTGCAGAGCGGCAA<br>CAGCCAGGAGAGCGTGACCGAGCAGGACAGCAAGGA<br>CAGCACCTACAGCCTGAGCAGCACCCTGACCCTGAGC<br>AAGGCCGACTACGAGAAGCACAAGGTGTACGCCTGC<br>GAGGTGACCCACCAGGGCCTGAGCAGCCCCGTGACC<br>AAGAGCTTCAACAGGGGCGAGTGC |
| SEQ ID NO: 23(VH1,<br>aa) | EVMLLESGGGLVQPGGSLRLSCAASGFIFSSYAMS<br>WVRQAPGTGLEWVATISSGGSNTYSPDTVKGRFTIS<br>RDNSKNTLYLQMNSLRAEDTAVYYCARYYGYYFD<br>FWGQGTLLTVSS |
| SEQ ID NO: 24(VH1,<br>nt) | GAGGTGATGCTGCTGGAGAGCGGCGGCGGCCTG<br>GTGCAGCCCGGCGGCAGCCTGAGGCTGAGCTGCG<br>CCGCCAGCGGCTTCATCTTCAGCAGCTACGCCAT<br>GAGCTGGGTGAGGCAGGCCCCCGGCACCGGCCTG<br>GAGTGGGTGGCCACCATCAGCAGCGGCGGCAGC<br>AACACCTACAGCCCCGACACCGTGAAGGGCAGGT<br>TCACCATCAGCAGGGACAACAGCAAGAACACCCT<br>GTACCTGCAGATGAACAGCCTGAGGGCCGAGGA<br>CACCGCCGTGTACTACTGCGCCAGGTACTACGGC<br>TACTACTTCGACTTCTGGGGCCAGGGCACCCTGC<br>TGACCGTGAGCAGC |
| SEQ ID NO: 25(full heavy<br>chain 1,<br>aa) | EVMLLESGGGLVQPGGSLRLSCAASGFIFSSYAMS<br>WVRQAPGTGLEWVATISSGGSNTYSPDTVKGRFTIS<br>RDNSKNTLYLQMNSLRAEDTAVYYCARYYGYYFD<br>FWGQGTLLTVSSASTKGPSVFPLAPSSKSTSGGTAALG<br>CLVKDYFPEPVTVSWNSGALTSGVHTFPAVLQSSGLYS<br>LSSVVTVPSSSLGTQTYICNVNHKPSNTKVDKKVEPKSC<br>DKTHTCPPCPAPELLGGPSVFLFPPKPKDTLMISRTPEVT<br>CVVVDVSHEDPEVKFNWYVDGVEVHNAKTKPREEQY<br>ASTYRVVSVLTVLHQDWLNGKEYKCKVSNKALPAPIE<br>KTISKAKGQPREPQVYTLPPSREEMTKNQVSLTCLVKGF<br>YPSDIAVEWESNGQPENNYKTTPPVLDSDGSFFLYSKLT<br>VDKSRWQQGNVFSCSVMHEALHNHYTQKSLSLSPGK |
| SEQ ID NO: 26(full heavy<br>chain 1,<br>nt) | GAGGTGATGCTGCTGGAGAGCGGCGGCGGCCTG<br>GTGCAGCCCGGCGGCAGCCTGAGGCTGAGCTGCG<br>CCGCCAGCGGCTTCATCTTCAGCAGCTACGCCAT<br>GAGCTGGGTGAGGCAGGCCCCCGGCACCGGCCTG<br>GAGTGGGTGGCCACCATCAGCAGCGGCGGCAGC<br>AACACCTACAGCCCCGACACCGTGAAGGGCAGGT<br>TCACCATCAGCAGGGACAACAGCAAGAACACCCT<br>GTACCTGCAGATGAACAGCCTGAGGGCCGAGGA<br>CACCGCCGTGTACTACTGCGCCAGGTACTACGGC<br>TACTACTTCGACTTCTGGGGCCAGGGCACCCTGC<br>TGACCGTGAGCAGCGCCAGCACCAAGGGCCCCA<br>GCGTGTTCCCCCTGGCCCCCAGCAGCAAGAGCAC<br>CAGCGGCGGCACCGCCGCCCTGGGCTGCCTGGTG |

TABLE I-continued

Description of the antibody sequence of the invention

| Sequence No. | Sequence |
|---|---|
| | AAGGACTACTTCCCCGAGCCCGTGACCGTGAGCT<br>GGAACAGCGGCGCCCTGACCAGCGGCGTGCACA<br>CCTTCCCCGCCGTGCTGCAGAGCAGCGGCCTGTA<br>CAGCCTGAGCAGCGTGGTGACCGTGCCCAGCAGC<br>AGCCTGGGCACCCAGACCTACATCTGCAACGTGA<br>ACCACAAGCCCAGCAACACCAAGGTGGACAAGA<br>AGGTGGAGCCCAAGAGCTGCGACAAGACCCACA<br>CCTGCCCCCCCTGCCCCGCCCCCGAGCTGCTGGG<br>CGGCCCCAGCGTGTTCCTGTTCCCCCCCAAGCCC<br>AAGGACACCCTGATGATCAGCAGGACCCCCGAG<br>GTGACCTGCGTGGTGGTGGACGTGAGCCACGAGG<br>ACCCCGAGGTGAAGTTCAACTGGTACGTGGACGG<br>CGTGGAGGTGCACAACGCCAAGACCAAGCCCAG<br>GGAGGAGCAGTACAACAGCACCTACAGGGTGGT<br>GAGCGTGCTGACCGTGCTGCACCAGGACTGGCTG<br>AACGGCAAGGAGTACAAGTGCAAGGTGAGCAAC<br>AAGGCCCTGCCCGCCCCCATCGAGAAGACCATCA<br>GCAAGGCCAAGGGCCAGCCCAGGGAGCCCCAGG<br>TGTACACCCTGCCCCCCAGCAGGGAGGAGATGAC<br>CAAGAACCAGGTGAGCCTGACCTGCCTGGTGAAG<br>GGCTTCTACCCCAGCGACATCGCCGTGGAGTGGG<br>AGAGCAACGGCCAGCCCGAGAACAACTACAAGA<br>CCACCCCCCCCGTGCTGGACAGCGACGGCAGCTT<br>CTTCCTGTACAGCAAGCTGACCGTGGACAAGAGC<br>AGGTGGCAGCAGGGCAACGTGTTCAGCTGCAGCG<br>TGATGCACGAGGCCCTGCACAACCACTACACCCA<br>GAAGAGCCTGAGCCTGAGCCCCGGCAAG |
| SEQ ID NO: 27(VH2, aa) | EVMLVESGGGLVQPGGSLRLSCAASGFIFSSYAMSWVR<br>QAPGTGLEWVATISSGGSNTYSPDTVKGRFTISRDNSKN<br>TLYLQMNSLRAEDTAMYYCARYYGYYFDFWGQGTLL<br>TVSS |
| SEQ ID NO: 28(VH2, nt) | GAGGTGATGCTGGTGGAGAGCGGCGGCGGCCTGGTG<br>CAGCCCGGCGGCAGCCTGAGGCTGAGCTGCGCCGCC<br>AGCGGCTTCATCTTCAGCAGCTACGCCATGAGCTGGG<br>TGAGGCAGGCCCCCGGCACCGGCCTGGAGTGGGTGG<br>CCACCATCAGCAGCGGCGGCAGCAACACCTACAGCC<br>CCGACACCGTGAAGGGCAGGTTCACCATCAGCAGGG<br>ACAACAGCAAGAACACCCTGTACCTGCAGATGAACA<br>GCCTGAGGGCCGAGGACACCGCCATGTACTACTGCG<br>CCAGGTACTACGGCTACTACTTCGACTTCTGGGGCCA<br>GGGCACCCTGCTGACCGTGAGCAGC |
| SEQ ID NO: 29(full heavy chain 2, aa) | EVMLVESGGGLVQPGGSLRLSCAASGFIFSSYAMSWVR<br>QAPGTGLEWVATISSGGSNTYSPDTVKGRFTISRDNSKN<br>TLYLQMNSLRAEDTAMYYCARYYGYYFDFWGQGTLL<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKKVEPKSCDKTHTCPPC<br>PAPELLGGPSVFLFPPKPKDTLMISRTPEVTCVVVDVSH<br>EDPEVKFNWYVDGVEVHNAKTKPREEQYNSTYRVVSV<br>LTVLHQDWLNGKEYKCKVSNKALPAPIEKTISKAKGQP<br>REPQVYTLPPSREEMTKNQVSLTCLVKGFYPSDIAVEW<br>ESNGQPENNYKTTPPVLDSDGSFFLYSKLTVDKSRWQQ<br>GNVFSCSVMHEALHNHYTQKSLSLSPGK |
| SEQ ID NO: 30 (full heavy chain 2, nt) | GAGGTGATGCTGGTGGAGAGCGGCGGCGGCCTGGTG<br>CAGCCCGGCGGCAGCCTGAGGCTGAGCTGCGCCGCC<br>AGCGGCTTCATCTTCAGCAGCTACGCCATGAGCTGGG<br>TGAGGCAGGCCCCCGGCACCGGCCTGGAGTGGGTGG<br>CCACCATCAGCAGCGGCGGCAGCAACACCTACAGCC<br>CCGACACCGTGAAGGGCAGGTTCACCATCAGCAGGG<br>ACAACAGCAAGAACACCCTGTACCTGCAGATGAACA<br>GCCTGAGGGCCGAGGACACCGCCATGTACTACTGCG<br>CCAGGTACTACGGCTACTACTTCGACTTCTGGGGCCA<br>GGGCACCCTGCTGACCGTGAGCAGCGCCAGCACCAA<br>GGGCCCCAGCGTGTTCCCCCTGGCCCCCAGCAGCAAG<br>AGCACCAGCGGCGGCACCGCCGCCCTGGGCTGCCTG<br>GTGAAGGACTACTTCCCCGAGCCCGTGACCGTGAGCT<br>GGAACAGCGGCGCCCTGACCAGCGGCGTGCACACCT<br>TCCCCGCCGTGCTGCAGAGCAGCGGCCTGTACAGCCT<br>GAGCAGCGTGGTGACCGTGCCCAGCAGCAGCCTGGG<br>CACCCAGACCTACATCTGCAACGTGAACCACAAGCCC<br>AGCAACACCAAGGTGGACAAGAAGGTGGAGCCCAAG<br>AGCTGCGACAAGACCCACACCTGCCCCCCCTGCCCCG |

TABLE I-continued

Description of the antibody sequence of the invention

| Sequence No. | Sequence |
|---|---|
| | CCCCCGAGCTGCTGGGCGGCCCCAGCGTGTTCCTGTT<br>CCCCCCCAAGCCCAAGGACACCCTGATGATCAGCAG<br>GACCCCCGAGGTGACCTGCGTGGTGGTGGACGTGAG<br>CCACGAGGACCCCGAGGTGAAGTTCAACTGGTACGT<br>GGACGGCGTGGAGGTGCACAACGCCAAGACCAAGCC<br>CAGGGAGGAGCAGTACAACAGCACCTACAGGGTGGT<br>GAGCGTGCTGACCGTGCTGCACCAGGACTGGCTGAA<br>CGGCAAGGAGTACAAGTGCAAGGTGAGCAACAAGGC<br>CCTGCCCGCCCCCATCGAGAAGACCATCAGCAAGGC<br>CAAGGGCCAGCCCAGGGAGCCCCAGGTGTACACCCT<br>GCCCCCCAGCAGGGAGGAGATGACCAAGAACCAGGT<br>GAGCCTGACCTGCCTGGTGAAGGGCTTCTACCCCAGC<br>GACATCGCCGTGGAGTGGGAGAGCAACGGCCAGCCC<br>GAGAACAACTACAAGACCACCCCCCCCGTGCTGGAC<br>AGCGACGGCAGCTTCTTCCTGTACAGCAAGCTGACCG<br>TGGACAAGAGCAGGTGGCAGCAGGGCAACGTGTTCA<br>GCTGCAGCGTGATGCACGAGGCCCTGCACAACCACT<br>ACACCCAGAAGAGCCTGAGCCTGAGCCCCGGCAAG |
| SEQ ID NO: 31 (VH3, aa) | EVMLVESGGGLVQPGGSLRLSCAASGFIFSSYAMS<br>WVRQAPETRLEWVATISSGGSNTYSPDTVKGRFTIS<br>RDNSKNTLYLQMNSLRAEDTAMYYCARYYGYYFD<br>FWGQGTLLTVSS |
| SEQ ID NO: 32 (VH3, nt) | GAGGTGATGCTGGTGGAGAGCGGCGGCGGCCTG<br>GTGCAGCCCGGCGGCAGCCTGAGGCTGAGCTGCG<br>CCGCCAGCGGCTTCATCTTCAGCAGCTACGCCAT<br>GAGCTGGGTGAGGCAGGCCCCCGAGACCAGGCT<br>GGAGTGGGTGGCCACCATCAGCAGCGGCGGCAG<br>CAACACCTACAGCCCCGACACCGTGAAGGGCAG<br>GTTCACCATCAGCAGGGACAACAGCAAGAACAC<br>CCTGTACCTGCAGATGAACAGCCTGAGGGCCGAG<br>GACACCGCCATGTACTACTGCGCCAGGTACTACG<br>GCTACTACTTCGACTTCTGGGGCCAGGGCACCCT<br>GCTGACCGTGAGCAGC |
| SEQ ID NO: 33 (full heavy chain 3, aa) | EVMLVESGGGLVQPGGSLRLSCAASGFIFSSYAMS<br>WVRQAPETRLEWVATISSGGSNTYSPDTVKGRFTIS<br>RDNSKNTLYLQMNSLRAEDTAMYYCARYYGYYFD<br>FWGQGTLLTVSSASTKGPSVFPLAPSSKSTSGGTAALG<br>CLVKDYFPEPVTVSWNSGALTSGVHTFPAVLQSSGLYS<br>LSSVVTVPSSSLGTQTYICNVNHKPSNTKVDKKVEPKSC<br>DKTHTCPPCPAPELLGGPSVFLFPPKPKDTLMISRTPEVT<br>CVVVDVSHEDPEVKFNWYVDGVEVHNAKTKPREEQY<br>ASTYRVVSVLTVLHQDWLNGKEYKCKVSNKALPAPIE<br>KTISKAKGQPREPQVYTLPPSREEMTKNQVSLTCLVKGF<br>YPSDIAVEWESNGQPENNYKTTPPVLDSDGSFFLYSKLT<br>VDKSRWQQGNVFSCSVMHEALHNHYTQKSLSLSPGK |
| SEQ ID NO: 34 (full heavy chain 3, nt) | GAGGTGATGCTGGTGGAGAGCGGCGGCGGCCTGGTG<br>CAGCCCGGCGGCAGCCTGAGGCTGAGCTGCGCCGCC<br>AGCGGCTTCATCTTCAGCAGCTACGCCATGAGCTGGG<br>TGAGGCAGGCCCCCGAGACCAGGCTGGAGTGGGTGG<br>CCACCATCAGCAGCGGCGGCAGCAACACCTACAGCC<br>CCGACACCGTGAAGGGCAGGTTCACCATCAGCAGGG<br>ACAACAGCAAGAACACCCTGTACCTGCAGATGAACA<br>GCCTGAGGGCCGAGGACACCGCCATGTACTACTGCG<br>CCAGGTACTACGGCTACTACTTCGACTTCTGGGGCCA<br>GGGCACCCTGCTGACCGTGAGCAGCGCCAGCACCAA<br>GGGCCCCAGCGTGTTCCCCCTGGCCCCCAGCAGCAAG<br>AGCACCAGCGGCGGCACCGCCGCCCTGGGCTGCCTG<br>GTGAAGGACTACTTCCCCGAGCCCGTGACCGTGAGCT<br>GGAACAGCGGCGCCCTGACCAGCGGCGTGCACACCT<br>TCCCCGCCGTGCTGCAGAGCAGCGGCCTGTACAGCCT<br>GAGCAGCGTGGTGACCGTGCCCAGCAGCAGCCTGGG<br>CACCCAGACCTACATCTGCAACGTGAACCACAAGCCC<br>AGCAACACCAAGGTGGACAAGAAGGTGGAGCCCAAG<br>AGCTGCGACAAGACCCACACCTGCCCCCCCTGCCCCG<br>CCCCCGAGCTGCTGGGCGGCCCCAGCGTGTTCCTGTT<br>CCCCCCCAAGCCCAAGGACACCCTGATGATCAGCAG<br>GACCCCCGAGGTGACCTGCGTGGTGGTGGACGTGAG<br>CCACGAGGACCCCGAGGTGAAGTTCAACTGGTACGT<br>GGACGGCGTGGAGGTGCACAACGCCAAGACCAAGCC<br>CAGGGAGGAGCAGTACAACAGCACCTACAGGGTGGT<br>GAGCGTGCTGACCGTGCTGCACCAGGACTGGCTGAA<br>CGGCAAGGAGTACAAGTGCAAGGTGAGCAACAAGGC |

TABLE I-continued

Description of the antibody sequence of the invention

| Sequence No. | Sequence |
| --- | --- |
| | CCTGCCCGCCCCCATCGAGAAGACCATCAGCAAGGC<br>CAAGGGCCAGCCCAGGGAGCCCCAGGTGTACACCCT<br>GCCCCCCAGCAGGGAGGAGATGACCAAGAACCAGGT<br>GAGCCTGACCTGCCTGGTGAAGGGCTTCTACCCCAGC<br>GACATCGCCGTGGAGTGGGAGAGCAACGGCCAGCCC<br>GAGAACAACTACAAGACCACCCCCCCCGTGCTGGAC<br>AGCGACGGCAGCTTCTTCCTGTACAGCAAGCTGACCG<br>TGGACAAGAGCAGGTGGCAGCAGGGCAACGTGTTCA<br>GCTGCAGCGTGATGCACGAGGCCCTGCACAACCACT<br>ACACCCAGAAGAGCCTGAGCCTGAGCCCCGGCAAG |
| SEQ ID NO: 35(38E<br>HuH3L2-m or 38E<br>HuH3L4-m full heavy<br>chain, aa) | EVMLVESGGGLVQPGGSLRLSCAASGFIFSSYAMSWVR<br>QAPETRLEWVATISSGGSNTYSPDTVKGRFTISRDNSKN<br>TLYLQMNSLRAEDTAMYYCARYYGYYFDFWGQGTLL<br>TVSSAKTTPPSVYPLAPGSAAQTNSMVTLGCLVKGYFP<br>EPVTVTWNSGSLSSGVHTFPAVLQSDLYTLSSSVTVPSS<br>TWPSETVTCNVAHPASSTKVDKKIVPRDCGCKPCICTVP<br>EVSSVFIFPPKPKDVLTITLTPKVTCVVVDISKDDPEVQF<br>SWFVDDVEVHTAQTQPREEQFNSTFRSVSELPIMHQDW<br>LNGKEFKCRVNSAAFPAPIEKTISKTKGRPKAPQVYTIPP<br>PKEQMAKDKVSLTCMITDFFPEDITVEWQWNGQPAEN<br>YKNTQPIMDTDGSYFVYSKLNVQKSNWEAGNTFTCSV<br>LHEGLHNHHTEKSLSHSPGK |
| SEQ ID NO: 36(38E<br>HuH3L2-m or 38E<br>HuH3L4-m full heavy chain,<br>nt) | GAGGTGATGCTGGTGGAGAGCGGCGGCGGCCTGGTG<br>CAGCCCGGCGGCAGCCTGAGGCTGAGCTGCGCCGCC<br>AGCGGCTTCATCTTCAGCAGCTACGCCATGAGCTGGG<br>TGAGGCAGGCCCCCGAGACCAGGCTGGAGTGGGTGG<br>CCACCATCAGCAGCGGCGGCAGCAACACCTACAGCC<br>CCGACACCGTGAAGGGCAGGTTCACCATCAGCAGGG<br>ACAACAGCAAGAACACCCTGTACCTGCAGATGAACA<br>GCCTGAGGGCCGAGGACACCGCCATGTACTACTGCG<br>CCAGGTACTACGGCTACTACTTCGACTTCTGGGGCCA<br>GGGCACCCTGCTGACCGTGAGCAGCGCCAAGACCAC<br>CCCCCCCAGCGTGTACCCCCTGGCCCCCGGCAGCGCC<br>GCCCAGACCAACAGCATGGTGACCCTGGGCTGCCTG<br>GTGAAGGGCTACTTCCCCGAGCCCGTGACCGTGACCT<br>GGAACAGCGGCAGCCTGAGCAGCGGCGTGCACACCT<br>TCCCCGCCGTGCTGCAGAGCGACCTGTACACCCTGAG<br>CAGCAGCGTGACCGTGCCCAGCAGCACCTGGCCCAG<br>CGAGACCGTGACCTGCAACGTGGCCCACCCCGCCAG<br>CAGCACCAAGGTGGACAAGAAGATCGTGCCCAGGGA<br>CTGCGGCTGCAAGCCCTGCATCTGCACCGTGCCCGAG<br>GTGAGCAGCGTGTTCATCTTCCCCCCCAAGCCCAAGG<br>ACGTGCTGACCATCACCCTGACCCCCAAGGTGACCTG<br>CGTGGTGGTGGACATCAGCAAGGACGACCCCGAGGT<br>GCAGTTCAGCTGGTTCGTGGACGACGTGGAGGTGCAC<br>ACCGCCCAGACCCAGCCCAGGGAGGAGCAGTTCAAC<br>AGCACCTTCAGGAGCGTGAGCGAGCTGCCCATCATGC<br>ACCAGGACTGGCTGAACGGCAAGGAGTTCAAGTGCA<br>GGGTGAACAGCGCCGCCTTCCCCGCCCCCATCGAGAA<br>GACCATCAGCAAGACCAAGGGCAGGCCCAAGGCCCC<br>CCAGGTGTACACCATCCCCCCCCCCAAGGAGCAGATG<br>GCCAAGGACAAGGTGAGCCTGACCTGCATGATCACC<br>GACTTCTTCCCCGAGGACATCACCGTGGAGTGGCAGT<br>GGAACGGCCAGCCCGCCGAGAACTACAAGAACACCC<br>AGCCCATCATGGACACCGACGGCAGCTACTTCGTGTA<br>CAGCAAGCTGAACGTGCAGAAGAGCAACTGGGAGGC<br>CGGCAACACCTTCACCTGCAGCGTGCTGCACGAGGGC<br>CTGCACAACCACCACACCGAGAAGAGCCTGAGCCAC<br>AGCCCCGGCAAG |
| SEQ ID NO: 37 (38E<br>HuH3L2-m full light chain,<br>aa) | DIHMTQSPSSLSASVGDRVTITCRASENIYSYLAWYQQK<br>PGKSPKLLVYNAKTLAEGVPSRFSGSGSGTDFTLTISSLQ<br>PEDFATYYCQHHYVTPLTFGQGTKLEIKRADAAPTVSIF<br>PPSSEQLTSGGASVVCFLNNFYPKDINVKWKIDGSERQN<br>GVLNSWTDQDSKDSTYSMSSTLTLTKDEYERHNSYTCE<br>ATHKTSTSPIVKSFNRNEC |
| SEQ ID NO: 38 (38E<br>HuH3L2-m full light chain,<br>nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCCCGGCAAGAGCCCCAAGCTGCTGGTGT<br>ACAACGCCAAGACCCTGGCCGAGGGCGTGCCCAGCA<br>GGTTCAGCGGCAGCGGCAGCGGCACCGACTTCACCCT<br>GACCATCAGCAGCCTGCAGCCCGAGGACTTCGCCACC |

TABLE I-continued

Description of the antibody sequence of the invention

| Sequence No. | Sequence |
|---|---|
| | TACTACTGCCAGCACCACTACGTGACCCCCCTGACCT<br>TCGGCCAGGGCACCAAGCTGGAGATCAAGAGGGCCG<br>ACGCCGCCCCCACCGTGAGCATCTTCCCCCCCAGCAG<br>CGAGCAGCTGACCAGCGGCGGCGCCAGCGTGGTGTG<br>CTTCCTGAACAACTTCTACCCCAAGGACATCAACGTG<br>AAGTGGAAGATCGACGGCAGCGAGAGGCAGAACGGC<br>GTGCTGAACAGCTGGACCGACCAGGACAGCAAGGAC<br>AGCACCTACAGCATGAGCAGCACCCTGACCCTGACC<br>AAGGACGAGTACGAGAGGCACAACAGCTACACCTGC<br>GAGGCCACCCACAAGACCAGCACCAGCCCCATCGTG<br>AAGAGCTTCAACAGGAACGAGTGC |
| SEQ ID NO: 39 (38E<br>HuH3L4-m full light chain,<br>aa) | DIHMTQSPSSLSASVGDRVTITCRASENIYSYLAWYQQK<br>QGKSPQLLVYNAKTLAEGVPSRFSGSGSGTQFTLKINSL<br>QPEDFATYYCQHHYVTPLTFGQGTKLEIKRADAAPTVSI<br>FPPSSEQLTSGGASVVCFLNNFYPKDINVKWKIDGSERQ<br>NGVLNSWTDQDSKDSTYSMSSTLTLTKDEYERHNSYTC<br>EATHKTSTSPIVKSFNRNEC |
| SEQ ID NO: 40 (38E<br>HuH3L4-m full light chain,<br>nt) | GACATCCACATGACCCAGAGCCCCAGCAGCCTGAGC<br>GCCAGCGTGGGCGACAGGGTGACCATCACCTGCAGG<br>GCCAGCGAGAACATCTACAGCTACCTGGCCTGGTACC<br>AGCAGAAGCAGGGCAAGAGCCCCCAGCTGCTGGTGT<br>ACAACGCCAAGACCCTGGCCGAGGGCGTGCCCAGCA<br>GGTTCAGCGGCAGCGGCAGCGGCACCCAGTTCACCCT<br>GAAGATCAACAGCCTGCAGCCCGAGGACTTCGCCAC<br>CTACTACTGCCAGCACCACTACGTGACCCCCCTGACC<br>TTCGGCCAGGGCACCAAGCTGGAGATCAAGAGGACC<br>GTGGCCGCCCCCAGCGTGTTCATCTTCCCCCCCAGCG<br>ACGAGCAGCTGAAGAGCGGCACCGCCAGCGTGGTGT<br>GCCTGCTGAACAACTTCTACCCCAGGGAGGCCAAGGT<br>GCAGTGGAAGGTGGACAACGCCCTGCAGAGCGGCAA<br>CAGCCAGGAGAGCGTGACCGAGCAGGACAGCAAGGA<br>CAGCACCTACAGCCTGAGCAGCACCCTGACCCTGAGC<br>AAGGCCGACTACGAGAAGCACAAGGTGTACGCCTGC<br>GAGGTGACCCACCAGGGCCTGAGCAGCCCCGTGACC<br>AAGAGCTTCAACAGGGGCGAGTGC |
| SEQ ID NO: 41<br>(38E10E1C11 full light<br>chain aa) | DIHMTQSPASLSASVGETVTITCRASENIYSYLAWYQQK<br>QGKSPQLLVYNAKTLAEGVPSRFSGSGSGTQFSLKINSL<br>QPEDFGSYYCQHHYVTPLTFGAGTKLELKRADAAPTVS<br>IFPPSSEQLTSGGASVVCFLNNFYPKDINVKWKIDGSER<br>QNGVLNSWTDQDSKDSTYSMSSTLTLTKDEYERHNSYT<br>CEATHKTSTSPIVKSFNRNEC |
| SEQ ID NO: 42<br>(38E10E1C11 full light<br>chain nt) | GACATCCACATGACTCAGTCTCCAGCCTCCCTATCTG<br>CATCTGTGGGAGAAACTGTCACCATCACATGTCGAGC<br>AAGTGAGAATATTTACAGTTATTTAGCATGGTATCAG<br>CAGAAACAGGGAAAATCTCCTCAGCTCCTGGTCTATA<br>ATGCAAAAACCTTAGCAGAAGGTGTGCCATCAAGGT<br>TCAGTGGCAGTGGATCAGGCACACAGTTTTCTCTGAA<br>GATCAACAGCCTGCAGCCTGAAGATTTTGGGAGTTAT<br>TACTGTCAACATCATTATGTTACTCCGCTCACGTTCGG<br>TGCTGGGACCAAGCTGGAGCTGAAACGGGCTGATGC<br>TGCACCAACTGTATCCATCTTCCCACCATCCAGTGAG<br>CAGTTAACATCTGGAGGTGCCTCAGTCGTGTGCTTCT<br>TGAACAACTTCTACCCCAAAGACATCAATGTCAAGTG<br>GAAGATTGATGGCAGTGAACGACAAAATGGCGTCCT<br>GAACAGTTGGACTGATCAGGACAGCAAAGACAGCAC<br>CTACAGCATGAGCAGCACCCTCACGTTGACCAAGGA<br>CGAGTATGAACGACATAACAGCTATACCTGTGAGGC<br>CACTCACAAGACATCAACTTCACCCATTGTCAAGAGC<br>TTCAACAGGAATGAGTGT |
| SEQ ID NO: 43<br>(38E10E1C11 full heavy<br>chain aa) | EVMLVESGGGLVKPGGSLKLSCAASGFIFSSYAMSWVR<br>QSPETRLEWVATISSGGSNTYSPDSVKGRFTISRDNAKN<br>TLYLQMSSLRSEDTAMYYCARYYGYYFDFWGQGTTLT<br>VSSAKTTPPSVYPLAPGSAAQTNSMVTLGCLVKGYFPEP<br>VTVTWNSGSLSSGVHTFPAVLQSDLYTLSSSVTVPSSTW<br>PSETVTCNVAHPASSTKVDKKIVPRDCGCKPCICTVPEV<br>SSVFIFPPKPKDVLTITLTPKVTCVVVDISKDDPEVQFSW<br>FVDDVEVHTAQTQPREEQFNSTFRSVSELPIMHQDWLN<br>GKEFKCRVNSAAFPAPIEKTISKTKGRPKAPQVYTIPPPK<br>EQMAKDKVSLTCMITDFFPEDITVEWQWNGQPAENYK<br>NTQPIMDTDGSYFVYSKLNVQKSNWEAGNTFTCSVLHE<br>GLHNHHTEKSLSHSPGK |

TABLE I-continued

Description of the antibody sequence of the invention

| Sequence No. | Sequence |
|---|---|
| SEQ ID NO: 44 (38E10E1C11 full heavy chain nt) | GAAGTGATGCTGGTGGAGTCTGGGGGAGGCTTAGTG AAGCCTGGAGGGTCCCTGAAACTCTCCTGTGCAGCCT CTGGATTCATTTTCAGTAGTTATGCCATGTCTTGGGTT CGCCAGAGTCCGGAGACGAGGCTGGAGTGGGTCGCA ACCATTAGTAGTGGTGGTAGTAACACCTACTCTCCAG ACAGTGTGAAGGGGCGATTCACCATCTCCAGAGACA ATGCCAAGAACACCCTGTACCTGCAAATGAGCAGTCT GAGGTCTGAGGACACGGCCATGTATTACTGTGCAAG ATATTATGGTTACTACTTTGACTTCTGGGGCCAAGGC ACCACTCTCACAGTCTCCTCAGCCAAAACGACACCCC CATCTGTCTATCCACTGGCCCCTGGATCTGCTGCCCA AACTAACTCCATGGTGACCCTGGGATGCCTGGTCAAG GGCTATTTCCCTGAGCCAGTGACAGTGACCTGGAACT CTGGATCCCTGTCCAGCGGTGTGCACACCTTCCCAGC TGTCCTGCAGTCTGACCTCTACACTCTGAGCAGCTCA GTGACTGTCCCCTCCAGCACCTGGCCCAGCGAGACCG TCACCTGCAACGTTGCCCACCGGCCAGCAGCACCAA GGTGGACAAGAAAATTGTGCCCAGGGATTGTGGTTGT AAGCCTTGCATATGTACAGTCCCAGAAGTATCATCTG TCTTCATCTTCCCCCAAAGCCCAAGGATGTGCTCAC CATTACTCTGACTCCTAAGGTCACGTGTGTTGTGGTA GACATCAGCAAGGATGATCCCGAGGTCCAGTTCAGCT GGTTTGTAGATGATGTGGAGGTGCACACAGCTCAGAC GCAACCCCGGGAGGAGCAGTTCAACAGCACTTTCCG CTCAGTCAGTGAACTTCCCATCATGCACCAGGACTGG CTCAATGGCAAGGAGTTCAAATGCAGGGTCAACAGT GCAGCTTTCCCTGCCCCATCGAGAAAACCATCTCCA AAACCAAAGGCAGACCGAAGGCTCCACAGGTGTACA CCATTCCACCTCCCAAGGAGCAGATGGCCAAGGATA AAGTCAGTCTGACCTGCATGATAACAGACTTCTTCCC TGAAGACATTACTGTGGAGTGGCAGTGGAATGGGCA GCCAGCGGAGAACTACAAGAACACTCAGCCCATCAT GGACACAGATGGCTCTTACTTCGTCTACAGCAAGCTC AATGTGCAGAAGAGCAACTGGGAGGCAGGAAATACT TTCACCTGCTCTGTGTTACATGAGGGCCTGCACAACC ACCATACTGAGAAGAGCCTCTCCCACTCTCCTGGTAA A |
| SEQ ID NO: 45 (38E10E1C11 或 38E Chimeric HCDR2 aa) | TISSGGSNTYSPDSVKG |
| SEQ ID NO: 46 (38E Chimeric VL aa) | DIHMTQSPASLSASVGETVTITCRASENIYSYLAWYQQK QGKSPQLLVYNAKTLAEGVPSRFSGSGSGTQFSLKINSL QPEDFGSYYCQHHYVTPLTFGAGTKLELKR |
| SEQ ID NO: 47 (38E Chimeric VL nt) | GACATCCACATGACTCAGTCTCCAGCCTCCCTATCTG CATCTGTGGGAGAAACTGTCACCATCACATGTCGAGC AAGTGAGAATATTTACAGTTATTTAGCATGGTATCAG CAGAAACAGGGAAAATCTCCTCAGCTCCTGTCTATAA TGCAAAAACCTTAGCAGAAGGTGTGCCATCAAGGTTC AGTGGCAGTGGATCAGGCACACATTTTCTCTGAAGAT CAACAGCCTGCAGCCTGAAGATTTTGGGAGTTATTAC TGTCAACATCATTATGTTACTCCGCTCACGTTCGGTGC TGGGACCAAGCTGGAGCTGAAACGGGC |
| SEQ ID NO: 48 (38E Chimeric VH aa) | EVMLVESGGGLVKPGGSLKLSCAASGFIFSSYAMSWVR QSPETRLEWVATISSGGSNTYSPDSVKGRFTISRDNAKN TLYLQMSSLRSEDTAMYYCARYYGYYFDFWGQGTTLT VSS |
| SEQ ID NO: 49 (38E Chimeric VH nt) | GAAGTGATGCTGGTGGAGTCTGGGGGAGGCTTAGTG AAGCCTGGAGGGTCCCTGAAACTCTCCTGTGCAGCCT CTGGATTCATTTTCAGTAGTTATGCCATGTCTTGGGTT CGCCAGAGTCCGGAGACGAGGCTGGAGTGGGTCGCA ACCATTAGTAGTGGTGGTAGTAACACCTACTCTCCAG ACAGTGTGAAGGGGCGATTCACCATCTCCAGAGACA ATGCCAAGAACACCCTGTACCTGCAAATGAGCAGTCT GAGGTCTGAGGACACGGCCATGTATTACTGTGCAAG ATATTATGGTTACTACTTTGACTTCTGGGGCCAAGGC ACCACTCTCACAGTCTCCTCA |
| SEQ ID NO: 50 (38E Chimeric full light chain aa) | DIHMTQSPASLSASVGETVTITCRASENIYSYLAWYQQK QGKSPQLLVYNAKTLAEGVPSRFSGSGSGTQFSLKINSL QPEDFGSYYCQHHYVTPLTFGAGTKLELKRTVAAPSVFI |

TABLE I-continued

Description of the antibody sequence of the invention

| Sequence No. | Sequence |
| --- | --- |
| | FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC |
| SEQ ID NO: 51 (38E Chimeric full light chain nt) | GACATCCACATGACCCAGAGCCCCGCCAGCCTGAGC GCCAGCGTGGGCGAGACCGTGACCATCACCTGCAGG GCCAGCGAGAACATCTACAGCTACCTGGCCTGGTACC AGCAGAAGCAGGGCAAGAGCCCCCAGCTGCTGGTGT ACAACGCCAAGACCCTGGCCGAGGGCGTGCCCAGCA GGTTCAGCGGCAGCGGCAGCGGCACCCAGTTCAGCC TGAAGATCAACAGCCTGCAGCCCGAGGACTTCGGCA GCTACTACTGCCAGCACCACTACGTGACCCCCCTGAC CTTCGGCGCCGGCACCAAGCTGGAGCTGAAGAGGAC CGTGGCCGCCCCCAGCGTGTTCATCTTCCCCCCCAGC GACGAGCAGCTGAAGAGCGGCACCGCCAGCGTGGTG TGCCTGCTGAACAACTTCTACCCCAGGGAGGCCAAGG TGCAGTGGAAGGTGGACAACGCCCTGCAGAGCGGCA ACAGCCAGGAGAGCGTGACCGAGCAGGACAGCAAGG ACAGCACCTACAGCCTGAGCAGCACCCTGACCCTGA GCAAGGCCGACTACGAGAAGCACAAGGTGTACGCCT GCGAGGTGACCCACCAGGGCCTGAGCAGCCCCGTGA CCAAGAGCTTCAACAGGGGCGAGTGC |
| SEQ ID NO: 52 (38E Chimeric full heavy chain aa) | EVMLVESGGGLVKPGGSLKLSCAASGFIFSSYAMSWVR QSPETRLEWVATISSGGGSNTYSPDSVKGRFTISRDNAKN TLYLQMSSLRSEDTAMYYCARYYGYYFDFWGQGTTLT VSSASTKGPSVFPLAPSSKSTSGGTAALGCLVKDYFPEP VTVSWNSGALTSGVHTFPAVLQSSGLYSLSSVVTVPSSS LGTQTYICNVNHKPSNTKVDKKVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 53 (38E Chimeric full heavy chain nt) | GAGGTGATGCTGGTGGAGAGCGGCGGCGGCCTGGTG AAGCCCGGCGGCAGCCTGAAGCTGAGCTGCGCCGCC AGCGGCTTCATCTTCAGCAGCTACGCCATGAGCTGGG TGAGGCAGAGCCCCGAGACCAGGCTGGAGTGGGTGG CCACCATCAGCAGCGGCGGCAGCAACACCTACAGCC CCGACAGCGTGAAGGGCAGGTTCACCATCAGCAGGG ACAACGCCAAGAACACCCTGTACCTGCAGATGAGCA GCCTGAGGAGCGAGGACACCGCCATGTACTACTGCG CCAGGTACTACGGCTACTACTTCGACTTCTGGGGCCA GGGCACCACCCTGACCGTGAGCAGCGCCAGCACCAA GGGCCCCAGCGTGTTCCCCCTGGCCCCCAGCAGCAAG AGCACCAGCGGCGGCACCGCCGCCCTGGGCTGCCTG GTGAAGGACTACTTCCCCGAGCCCGTGACCGTGAGCT GGAACAGCGGCGCCCTGACCAGCGGCGTGCACACCT TCCCCGCCGTGCTGCAGAGCAGCGGCCTGTACAGCCT GAGCAGCGTGGTGACCGTGCCCAGCAGCAGCCTGGG CACCCAGACCTACATCTGCAACGTGAACCACAAGCCC AGCAACACCAAGGTGGACAAGAAGGTGGAGCCCAAG AGCTGCGACAAGACCCACACCTGCCCCCCCTGCCCCG CCCCCGAGCTGCTGGGCGGCCCCAGCGTGTTCCTGTT CCCCCCCAAGCCCAAGGACACCCTGATGATCAGCAG GACCCCCGAGGTGACCTGCGTGGTGGTGGACGTGAG CCACGAGGACCCCGAGGTGAAGTTCAACTGGTACGT GGACGGCGTGGAGGTGCACAACGCCAAGACCAAGCC CAGGGAGGAGCAGTACAACAGCACCTACAGGGTGGT GAGCGTGCTGACCGTGCTGCACCAGGACTGGCTGAA CGGCAAGGAGTACAAGTGCAAGGTGAGCAACAAGGC CCTGCCCGCCCCCATCGAGAAGACCATCAGCAAGGC CAAGGGCCAGCCCAGGGAGCCCCAGGTGTACACCCT GCCCCCCAGCAGGGAGGAGATGACCAAGAACCAGGT GAGCCTGACCTGCCTGGTGAAGGGCTTCTACCCCAGC GACATCGCCGTGGAGTGGGAGAGCAACGGCCAGCCC GAGAACAACTACAAGACCACCCCCCCCGTGCTGGAC AGCGACGGCAGCTTCTTCCTGTACAGCAAGCTGACCG TGGACAAGAGCAGGTGGCAGCAGGGCAACGTGTTCA GCTGCAGCGTGATGCACGAGGCCCTGCACAACCACT ACACCCAGAAGAGCCTGAGCCTGAGCCCCGGCAAG |
| SEQ ID NO: 54 (P36-033 full light chain aa) | DIVMTQSHKFMSTSVGDRVSITCKASQDVSNAVAWYQ QKPGQSPRLLIYWASFRHTGVPDRFTGSGSGTEYTLTIS |

TABLE I-continued

Description of the antibody sequence of the invention

| Sequence No. | Sequence |
|---|---|
| | RVQAEDLALYYCQQHYNTPYTFGGGTRLEIKRADAAPT VSIFPPSSEQLTSGGASVVCFLNNFYPKDINVKWKIDGSE RQNGVLNSWTDQDSKDSTYSMSSTLTLTKDEYERHNS YTCEATHKTSTSPIVKSFNRNEC |
| SEQ ID NO: 55 (P36-033 full light chain nt) | GACATCGTGATGACCCAGTCCCACAAGTTCATGAGCA CCAGCGTGGGCGATCGGGTGTCCATCACCTGTAAGGC CTCCCAGGACGTGAGCAACGCCGTGGCCTGGTATCAG CAGAAGCCTGGCCAGTCCCCTCGGCTGCTGATCTATT GGGCTTCCTTCAGGCACACCGGCGTGCCCGATCGGTT CACCGGCTCCGGATCCGGCACCGAGTATACCCTGACC ATCTCCCGGGTGCAGGCCGAGGATCTGGCTCTGTATT ATTGTCAGCAGCACTACAATACCCCCTACACCTTCGG CGGCGGCACCAGGCTGGAGATCAAGAGAGCTGATGC TGCCCCCACCGTGAGCATCTTCCCTCCCTCCAGCGAG CAGCTGACCTCCGGCGGAGCCTCCGTGGTGTGCTTCC TGAACAACTTCTACCCCAAGGATATCAACGTGAAGTG GAAGATCGACGGCAGCGAGCGGCAGAATGGCGTGCT GAACTCCTGGACCGACCAGGACAGCAAGGACTCCAC CTATTCCATGTCCTCCACCCTGACCCTGACCAAGGAT GAGTACGAGCGGCACAACAGCTATACCTGTGAGGCC ACCCACAAGACCTCCACCTCCCCCATCGTGAAGTCCT TCAATAGGAATGAGTGC |
| SEQ ID NO: 56 (P36-033 full heavy chain aa) | EVMLVESGGGLVQPGGSRRLSCAASGFTFSSYPMFWVR QTPEKRMEWVAYISNGGDSTYYPDTVKGRFTVSRDNA KNTLYLQMSSLKSVDTAIYYCVRPSARYDEWFAYWGQ GTLVTVSAAKTTPPSVYPLAPGSAAQTNSMVTLGCLVK GYFPEPVTVTWNSGSLSSGVHTFPAVLQSDLYTLSSSVT VPSSTWPSETVTCNVAHPASSTKVDKKIVPRDCGCKPCI CTVPEVSSVFIFPPKPKDVLTITLTPKVTCVVVDISKDDP EVQFSWFVDDVEVHTAQTQPREEQFNSTFRSVSELPIMH QDWLNGKEFKCRVNSAAFPAPIEKTISKTKGRPKAPQV YTIPPPKEQMAKDKVSLTCMITDFFPEDITVEWQWNGQ PAENYKNTQPIMDTDGSYFVYSKLNVQKSNWEAGNTF TCSVLHEGLHNHHTEKSLSHSPGK |
| SEQ ID NO: 57 (P36-033 full heavy chain nt) | GAGGTGATGCTGGTGGAGAGCGGCGGCGGCCTGGTG CAGCCCGGCGGCAGCAGGAGGCTGAGCTGCGCCGCC AGCGGCTTCACCTTCAGCAGCTACCCCATGTTCTGGG TGAGGCAGACCCCCGAGAAGAGGATGGAGTGGGTGG CCTACATCAGCAACGGCGGCGACAGCACCTACTACCC CGACACCGTGAAGGGCAGGTTCACCGTGAGCAGGGA CAACGCCAAGAACACCCTGTACCTGCAGATGAGCAG CCTGAAGAGCGTGGACACCGCCATCTACTACTGCGTG AGGCCCAGCGCCAGGTACGACGAGTGGTTCGCCTACT GGGGCCAGGGCACCCTGGTGACCGTGAGCAGCGCCA AGACCACCCCCCCCAGCGTGTACCCCCTGGCCCCCGG CAGCGCCGCCCAGACCAACAGCATGGTGACCCTGGG CTGCCTGGTGAAGGGCTACTTCCCCGAGCCCGTGACC GTGACCTGGAACAGCGGCAGCCTGAGCAGCGGCGTG CACACCTTCCCCGCCGTGCTGCAGAGCGACCTGTACA CCCTGAGCAGCAGCGTGACCGTGCCCAGCAGCACCT GGCCCAGCGAGACCGTGACCTGCAACGTGGCCCACC CCGCCAGCAGCACCAAGGTGGACAAGAAGATCGTGC CCAGGGACTGCGGCTGCAAGCCCTGCATCTGCACCGT GCCCGAGGTGAGCAGCGTGTTCATCTTCCCCCCCAAG CCCAAGGACGTGCTGACCATCACCCTGACCCCCAAGG TGACCTGCGTGGTGGTGGACATCAGCAAGGACGACC CCGAGGTGCAGTTCAGCTGGTTCGTGGACGACGTGGA GGTGCACACCGCCCAGACCCAGCCCAGGGAGGAGCA GTTCAACAGCACCTTCAGGAGCGTGAGCGAGCTGCCC ATCATGCACCAGGACTGGCTGAACGGCAAGGAGTTC AAGTGCAGGGTGAACAGCGCCGCCTTCCCCGCCCCA TCGAGAAGACCATCAGCAAGACCAAGGGCAGGCCCA AGGCCCCCCAGGTGTACACCATCCCCCCCCCCAAGGA GCAGATGGCCAAGGACAAGGTGAGCCTGACCTGCAT GATCACCGACTTCTTCCCCGAGGACATCACCGTGGAG TGGCAGTGGAACGGCCAGCCCGCCGAGAACTACAAG AACACCCAGCCCATCATGGACACCGACGGCAGCTAC TTCGTGTACAGCAAGCTGAACGTGCAGAAGAGCAAC TGGGAGGCCGGCAACACCTTCACCTGCAGCGTGCTGC ACGAGGGCCTGCACAACCACCACACCGAGAAGAGCC TGAGCCACAGCCCCGGCAAG |

TABLE I-continued

Description of the antibody sequence of the invention

| Sequence No. | Sequence |
| --- | --- |
| SEQ ID NO: 58 (Human LIF aa) | MKVLAAGVVPLLLVLHWKHGAGSPLPITPVNATCAIRH PCHNNLMNQIRSQLAQLNGSANALFILYYTAQGEPFPN NLDKLCGPNVTDFPPFHANGTEKAKLVELYRIVVYLGT SLGNITRDQKILNPSALSLHSKLNATADILRGLLSNVLCR LCSKYHVGHVDVTYGPDTSGKDVFQKKKLGCQLLGKY KQIIAVLAQAF |
| SEQ ID NO: 59 (Mut3 aa) | MKVLAAGVVPLLLVLHWKHGAGSPLPITPVNATCAIRH PCHNNLMNQIRSQLAQLNGSANALFILYYTAQGEPFPN NLDKLCGPNVTDFPPFHANGTEKAKLVELYRIVVYLGT SLGNITRDQKILNPSALSLHSKLNATADILRGLLSNVLCR LCSKYHVGHVDVTYGPDTSGKDVFQKKKLGCQLLGTY KQVISVVVQAF |
| SEQ ID NO: 60 (Mut4 aa) | MKVLAAGVVPLLLVLHWKHGAGSPLPITPVNATCAIRH PCHNNLMNQIRSQLAQLNGSANALFILYYTAQGEPFPN NLDKLCGPNVTDFPPFHANGTEKAKLVELYRIVVYLGT SLGNITRDQKILNPSALSLHSKLNATADILRGLLSNVLCR LCSKYHVGHVDVPPVPDHSDKEAFQRKKLGCQLLGTY KQVISVVVQAF |
| SEQ ID NO: 61 | TYGPDTSGKDVFQKK |
| SEQ ID NO: 62 (5D8 full heavy chain aa) | QVQLQESGGGLVKPGGSLRLSCAASGFTFSHAWMHWV RQAPGKGLEWVGQIKAKSDDYATYYAESVKGRFTISRD DSKNTLYLQMNSLKTEDTAVYYCTCWEWDLDFWGQG TMVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKGQ PREPQVYTLPPSREEMTKNQVSLTCLVKGFYPSDIAVEW ESNGQPENNYKTTPPVLDSDGSFFLYSKLTVDKSRWQQ GNVFSCSVMHEALHNHYTQKSLSLSPGK |
| SEQ ID NO: 63 (5D8 full heavy chain nt) | CAGGTGCAGCTGCAGGAGAGCGGCGGCGGCCTGGTG AAGCCCGGCGGCAGCCTGAGGCTGAGCTGCGCCGCC AGCGGCTTCACCTTCAGCCACGCCTGGATGCACTGGG TGAGGCAGGCCCCCGGCAAGGGCCTGGAGTGGGTGG GCCAGATCAAGGCCAAGAGCGACGACTACGCCACCT ACTACGCCGAGAGCGTGAAGGGCAGGTTCACCATCA GCAGGGACGACAGCAAGAACACCCTGTACCTGCAGA TGAACAGCCTGAAGACCGAGGACACCGCCGTGTACT ACTGCACCTGCTGGGAGTGGGACCTGGACTTCTGGGG CCAGGGCACCATGGTGACCGTGAGCAGCGCCAGCAC CAAGGGCCCCAGCGTGTTCCCCCTGGCCCCCAGCAGC AAGAGCACCAGCGGCGGCACCGCCGCCCTGGGCTGC CTGGTGAAGGACTACTTCCCCGAGCCCGTGACCGTGA GCTGGAACAGCGGCGCCCTGACCAGCGGCGTGCACA CCTTCCCCGCCGTGCTGCAGAGCAGCGGCCTGTACAG CCTGAGCAGCGTGGTGACCGTGCCCAGCAGCAGCCT GGGCACCCAGACCTACATCTGCAACGTGAACCACAA GCCCAGCAACACCAAGGTGGACAAGAGGGTGGAGCC CAAGAGCTGCGACAAGACCCACACCTGCCCCCCCTGC CCCGCCCCCGAGCTGCTGGGCGGCCCCAGCGTGTTCC TGTTCCCCCCCAAGCCCAAGGACACCCTGATGATCAG CAGGACCCCCGAGGTGACCTGCGTGGTGGTGGACGT GAGCCACGAGGACCCCGAGGTGAAGTTCAACTGGTA CGTGGACGGCGTGGAGGTGCACAACGCCAAGACCAA GCCCAGGGAGGAGCAGTACAACAGCACCTACAGGGT GGTGAGCGTGCTGACCGTGCTGCACCAGGACTGGCTG AACGGCAAGGAGTACAAGTGCAAGGTGAGCAACAAG GCCCTGCCCGCCCCCATCGAGAAGACCATCAGCAAG GCCAAGGGCCAGCCCAGGGAGCCCCAGGTGTACACC CTGCCCCCCAGCAGGGAGGAGATGACCAAGAACCAG GTGAGCCTGACCTGCCTGGTGAAGGGCTTCTACCCCA GCGACATCGCCGTGGAGTGGGAGAGCAACGGCCAGC CCGAGAACAACTACAAGACCACCCCCCCCGTGCTGG ACAGCGACGGCAGCTTCTTCCTGTACAGCAAGCTGAC CGTGGACAAGAGCAGGTGGCAGCAGGGCAACGTGTT CAGCTGCAGCGTGATGCACGAGGGCCCTGCACAACCA CTACACCCAGAAGAGCCTGAGCCTGAGCCCCGGCAA G |

TABLE I-continued

Description of the antibody sequence of the invention

| Sequence No. | Sequence |
| --- | --- |
| SEQ ID NO: 64<br>(5D8 full light chain aa) | DIVMTQTPLSSPVTLGQPASISCRSSQSLLDSDGHTYLN<br>WLQQRPGQPPRLLIYSVSNLESGVPDRFSGSGAGTDFTL<br>KISRVEAEDVGVYYCMQATHAPPYTFGQGTKLEIKRTV<br>AAPSVFIFPPSDEQLKSGTASVVCLLNNFYPREAKVQWK<br>VDNALQSGNSQESVTEQDSKDSTYSLSSTLTLSKADYE<br>KHKVYACEVTHQGLSSPVTKSFNRGEC |
| SEQ ID NO: 65<br>(5D8 full light chain nt) | GACATCGTGATGACCCAGACCCCCCTGAGCAGCCCCG<br>TGACCCTGGGCCAGCCCGCCAGCATCAGCTGCAGGA<br>GCAGCCAGAGCCTGCTGGACAGCGACGGCCACACCT<br>ACCTGAACTGGCTGCAGCAGAGGCCCGGCCAGCCCC<br>CCAGGCTGCTGATCTACAGCGTGAGCAACCTGGAGA<br>GCGGCGTGCCCGACAGGTTCAGCGGCAGCGGCGCCG<br>GCACCGACTTCACCCTGAAGATCAGCAGGGTGGAGG<br>CCGAGGACGTGGGCGTGTACTACTGCATGCAGGCCA<br>CCCACGCCCCCCCTACACCTTCGGCCAGGGCACCAA<br>GCTGGAGATCAAGAGGACCGTGGCCGCCCCCAGCGT<br>GTTCATCTTCCCCCCCAGCGACGAGCAGCTGAAGAGC<br>GGCACCGCCAGCGTGGTGTGCCTGCTGAACAACTTCT<br>ACCCCAGGGAGGCCAAGGTGCAGTGGAAGGTGGACA<br>ACGCCCTGCAGAGCGGCAACAGCCAGGAGAGCGTGA<br>CCGAGCAGGACAGCAAGGACAGCACCTACAGCCTGA<br>GCAGCACCCTGACCCTGAGCAAGGCCGACTACGAGA<br>AGCACAAGGTGTACGCCTGCGAGGTGACCCACCAGG<br>GCCTGAGCAGCCCCGTGACCAAGAGCTTCAACAGGG<br>GCGAGTGC |
| SEQ ID NO: 66<br>(P36-033 LCDR1 aa) | KASQDVSNAVA |
| SEQ ID NO: 67<br>(P36-033 LCDR2 aa) | WASFRHT |
| SEQ ID NO: 68<br>(P36-033 LCDR3 aa) | QQHYNTPYT |
| SEQ ID NO: 69<br>(P36-033 HCDR1 aa) | SYPMF |
| SEQ ID NO: 70<br>(P36-033 HCDR2 aa) | YISNGGDSTYYPDTVKG |
| SEQ ID NO: 71<br>(P36-033 HCDR3 aa) | PSARYDEWFAY |
| SEQ ID NO: 72<br>(P36-033 VL nt) | GACATCGTGATGACCCAGTCCCACAAGTTCATGAGCA<br>CCAGCGTGGGCGATCGGGTGTCCATCACCTGTAAGGC<br>CTCCCAGGACGTGAGCAACGCCGTGGCCTGGTATCAG<br>CAGAAGCCTGGCCAGTCCCCTCGGCTGCTGATCTATT<br>GGGCTTCCTTCAGGCACACCGGCGTGCCCGATCGGTT<br>CACCGGCTCCGGATCCGGCACCGAGTATACCCTGACC<br>ATCTCCCGGGTGCAGGCCGAGGATCTGGCTCTGTATT<br>ATTGTCAGCAGCACTACAATACCCCCTACACCTTCGG<br>CGGCGGCACCAGGCTGGAGATCAAG |
| SEQ ID NO: 73<br>(P36-033 VH nt) | GAGGTGATGCTGGTGGAGAGCGGCGGCGGCCTGGTG<br>CAGCCTGGAGGATCTCGGAGGCTGAGCTGTGCCGCC<br>AGCGGCTTCACCTTCTCCTCCTATCCCATGTTCTGGGT<br>GAGGCAGACCCCCGAGAAGCGGATGGAGTGGGTGGC<br>CTATATCTCCAATGGCGGCGATTCACCTATTATCCT<br>GACACCGTGAAGGGCCGGTTCACCGTGAGCCGGGAT<br>AACGCCAAGAATACCCTGTACCTGCAGATGAGCAGC<br>CTGAAGTCCGTGGACACCGCTATCTACTATTGCGTGA<br>GGCCCTCCGCTCGGTACGACGAGTGGTTCGCCTATTG<br>GGGCCAGGGCACCCTGGTGACAGTGAGCGCT |
| SEQ ID NO: 74<br>(38E10E1C11 VL aa) | DIHMTQSPASLSASVGETVTITCRASENIYSYLAWYQQK<br>QGKSPQLLVYNAKTLAEGVPSRFSGSGSGTQFSLKINSL<br>QPEDFGSYYCQHHYVTPLTFGAGTKLELKRA |
| SEQ ID NO: 75<br>(38E10E1C11 VH aa) | EVMLVESGGGLVKPGGSLKLSCAASGFIFSSYAMSWVR<br>QSPETRLEWVATISSGGSNTYSPDSVKGRFTISRDNAKN<br>TLYLQMSSLRSEDTAMYYCARYYGYYFDFWGQGTTLT<br>VSS |

TABLE I-continued

Description of the antibody sequence of the invention

| Sequence No. | Sequence |
| --- | --- |
| SEQ ID NO: 76 (38E10E1C11 VL nt) | GACATCCACATGACTCAGTCTCCAGCCTCCCTATCTG CATCTGTGGGAGAAACTGTCACCATCACATGTCGAGC AAGTGAGAATATTTACAGTTATTTAGCATGGTATCAG CAGAAACAGGGAAAATCTCCTCAGCTCCTGGTCTATA ATGCAAAAACCTTAGCAGAAGGTGTGCCATCAAGGT TCAGTGGCAGTGGATCAGGCACACAGTTTTCTCTGAA GATCAACAGCCTGCAGCCTGAAGATTTTGGGAGTTAT TACTGTCAACATCATTATGTTACTCCGCTCACGTTCGG TGCTGGGACCAAGCTGGAGCTGAAACGGGCT |
| SEQ ID NO: 77 (38E10E1C11 VH nt) | GAAGTGATGCTGGTGGAGTCTGGGGGAGGCTTAGTG AAGCCTGGAGGGTCCCTGAAACTCTCCTGTGCAGCCT CTGGATTCATTTTCAGTAGTTATGCCATGTCTTGGGTT CGCCAGAGTCCGGAGACGAGGCTGGAGTGGGTCGCA ACCATTAGTAGTGGTGGTAGTAACACCTACTCTCCAG ACAGTGTGAAGGGGCGATTCACCATCTCCAGAGACA ATGCCAAGAACACCCTGTACCTGCAAATGAGCAGTCT GAGGTCTGAGGACACGGCCATGTATTACTGTGCAAG ATATTATGGTTACTACTTTGACTTCTGGGGCCAAGGC ACCACTCTCACAGTCTCCTCA |
| SEQ ID NO: 78 (5D8 VH aa) | QVQLQESGGGLVKPGGSLRLSCAASGFTFSHAWMHWV RQAPGKGLEWVGQIKAKSDDYATYYAESVKGRFTISRD DSKNTLYLQMNSLKTEDTAVYYCTCWEWDLDFWGQG TMVTVSS |
| SEQ ID NO: 79 (5D8 VL aa) | DIVMTQTPLSSPVTLGQPASISCRSSQSLLDSDGHTYLN WLQQRPGQPPRLLIYSVSNLESGVPDRFSGSGAGTDFTL KISRVEAEDVGVYYCMQATHAPPYTFGQGTKLEIKRTV |
| SEQ ID NO: 80 (5D8 VH nt) | CAGGTGCAGCTGCAGGAGAGCGGCGGCGGCCTGGTG AAGCCCGGCGGCAGCCTGAGGCTGAGCTGCGCCGCC AGCGGCTTCACCTTCAGCCACGCCTGGATGCACTGGG TGAGGCAGGCCCCCGGCAAGGGCCTGGAGTGGGTGG GCCAGATCAAGGCCAAGAGCGACGACTACGCCACCT ACTACGCCGAGAGCGTGAAGGGCAGGTTCACCATCA GCAGGGACGACAGCAAGAACACCCTGTACCTGCAGA TGAACAGCCTGAAGACCGAGGACACCGCCGTGTACT ACTGCACCTGCTGGGAGTGGGACCTGGACTTCTGGGG CCAGGGCACCATGGTGACCGTGAGCAGC |
| SEQ ID NO: 81 (5D8 VL nt) | GACATCGTGATGACCCAGACCCCCCTGAGCAGCCCCG TGACCCTGGGCCAGCCCGCCAGCATCAGCTGCAGGA GCAGCCAGAGCCTGCTGGACAGCGACGGCCACACCT ACCTGAACTGGCTGCAGCAGAGGCCCGGCCAGCCCC CCAGGCTGCTGATCTACAGCGTGAGCAACCTGGAGA GCGGCGTGCCCGACAGGTTCAGCGGCAGCGGCGCCG GCACCGACTTCACCCTGAAGATCAGCAGGGTGGAGG CCGAGGACGTGGGCGTGTACTACTGCATGCAGGCCA CCCACGCCCCCCCCTACACCTTCGGCCAGGGCACCAA GCTGGAGATCAAGAGGACCGTG |
| SEQ ID NO: 82 (P36-033 VL aa) | DIVMTQSHKFMSTSVGDRVSITCKASQDVSNAVAWYQ QKPGQSPRLLIYWASFRHTGVPDRFTGSGSGTEYTLTIS RVQAEDLALYYCQQHYNTPYTFGGGTRLEIK |
| SEQ ID NO: 83 (P36-033 VH aa) | EVMLVESGGGLVQPGGSRRLSCAASGFTFSSYPMFWVR QTPEKRMEWVAYISNGGDSTYYPDTVKGRFTVSRDNA KNTLYLQMSSLKSVDTAIYYCVRPSARYDEWFAYWGQ GTLVTVSA |

Notes:
All amino acid numbers of CDRs and framework regions are annotated according to the EU index of the Kabat system (Kabat, E. A., et al. (1991) Sequences of Proteins of Immunological Interest, 5th Edition, U.S. Department of Health and Human Services, NIH Publication No. 91-3242). All sequences do not include Signal peptide. aa: amino acid, nt: nucleotide.

Notes: All amino acid numbers of CDRs and framework regions are annotated according to the EU index of the Kabat system (Kabat, E. A., et al. (1991) Sequences of Proteins of Immunological Interest, 5th Edition, U.S. Department of Health and Human Services, NIH Publication No. 91-3242). All sequences do not include Signal peptide. aa: amino acid, nt: nucleotide.

Figure 9:
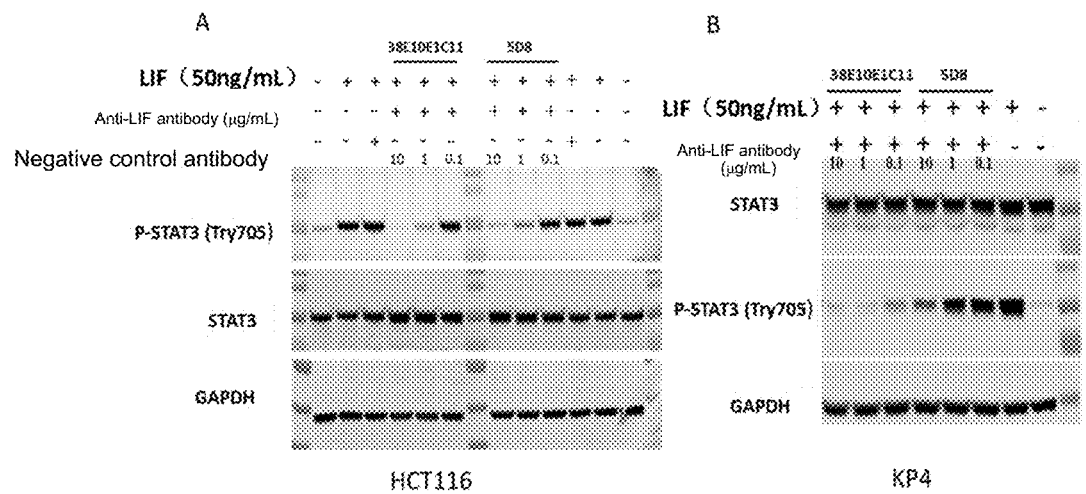
Figure 10:
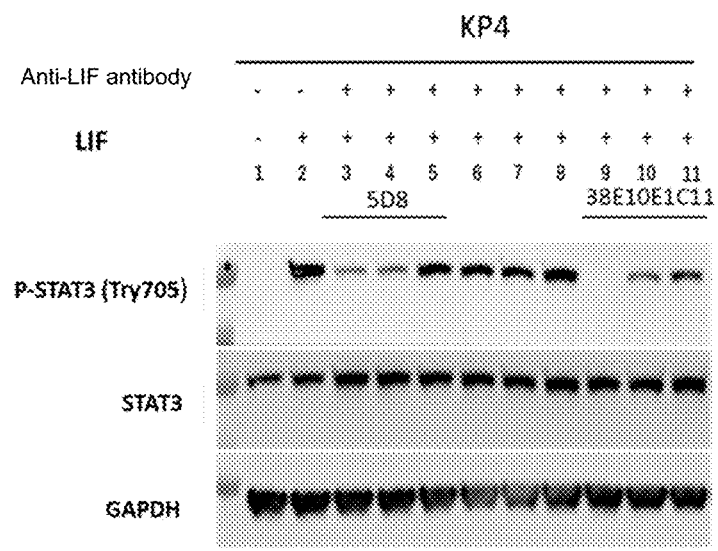
Figure 11:
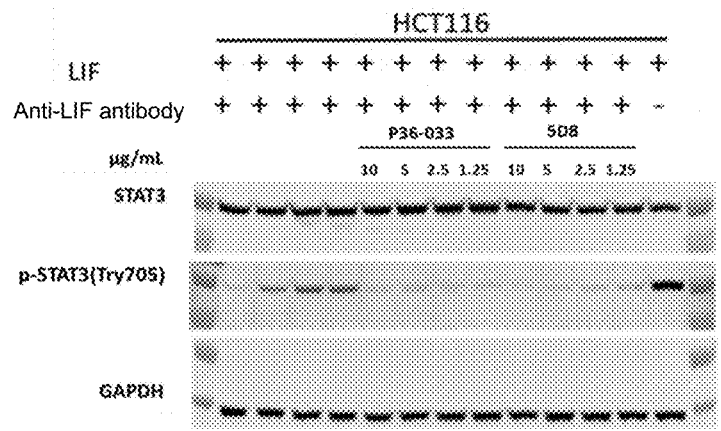
Figure 12:
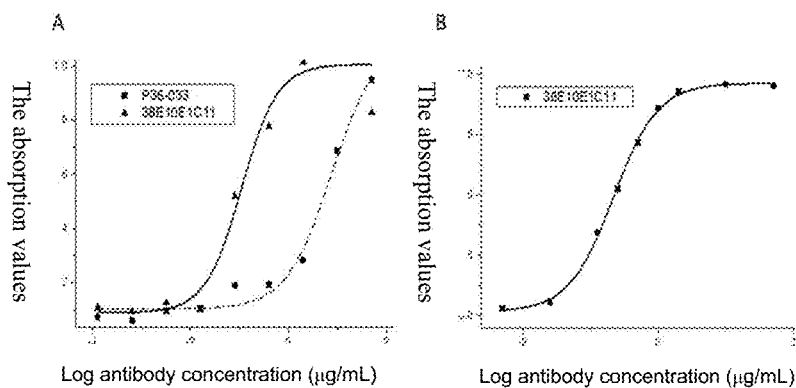
Figure 13:
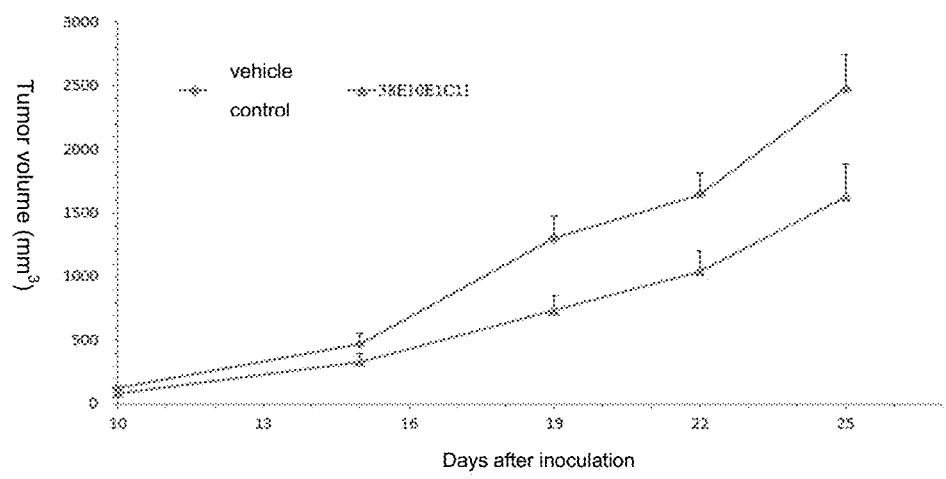
Figure 14:
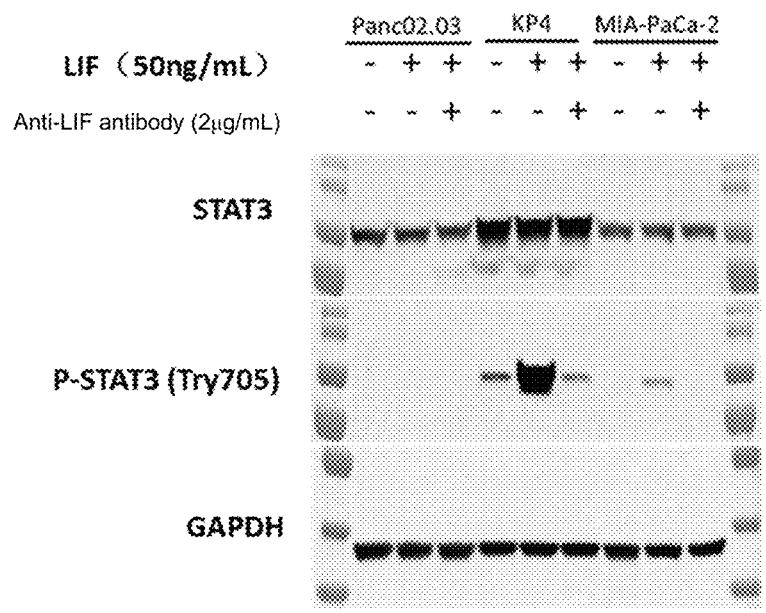
Figure 15:
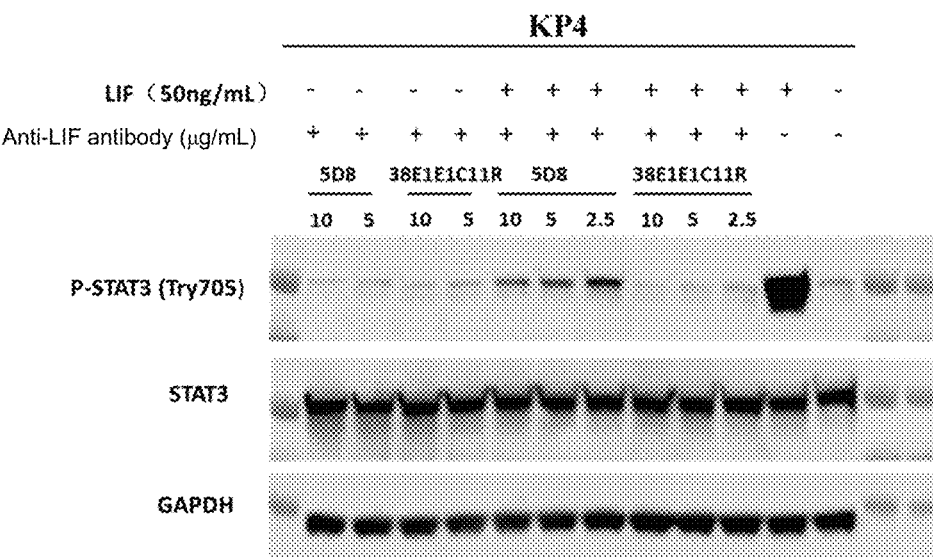
Figure 16:
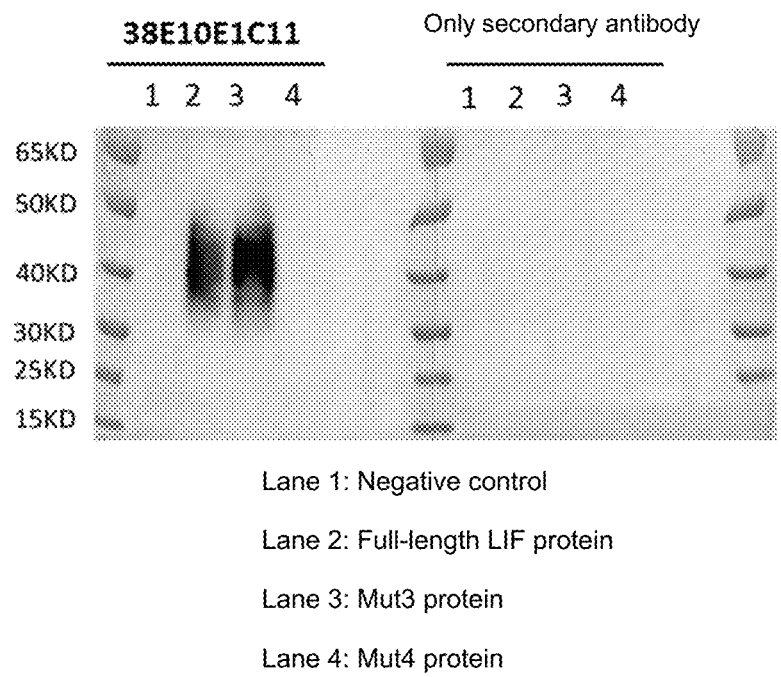
Figure 16:
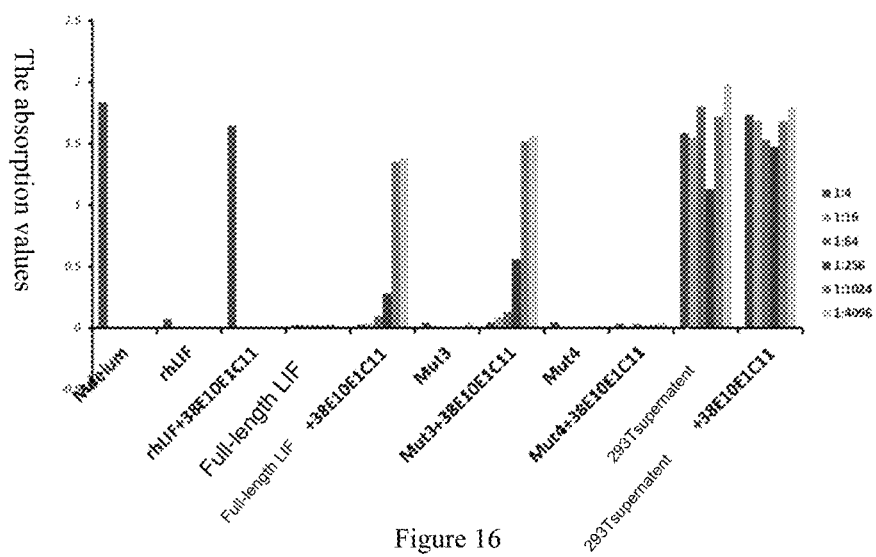
Figure 18:
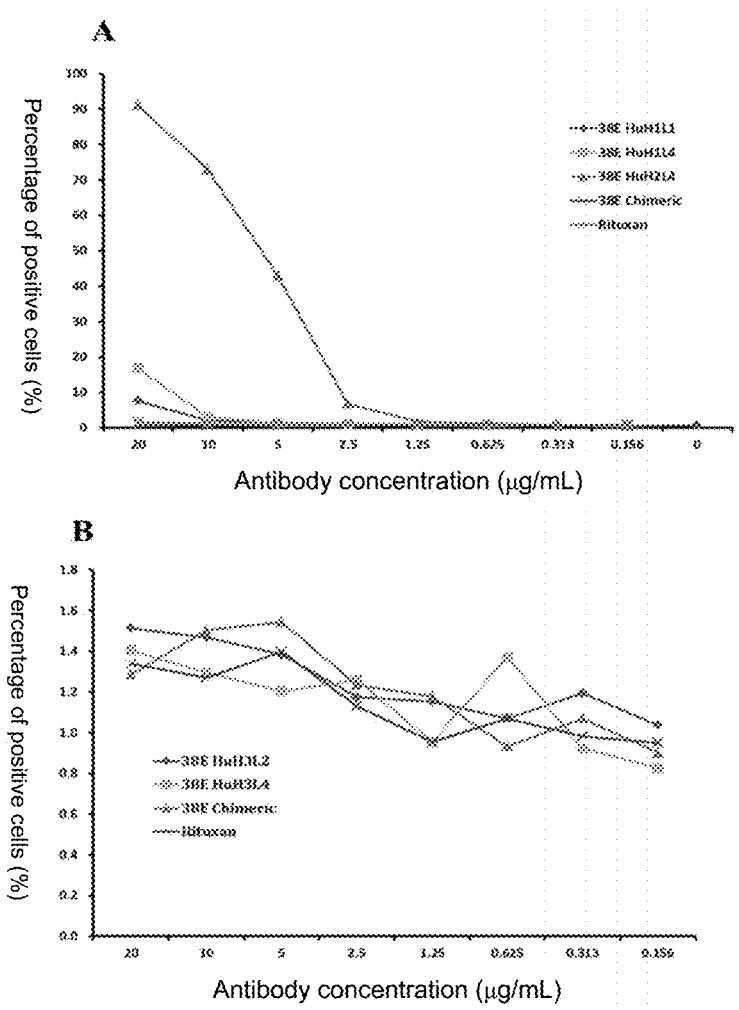
Figure 19:
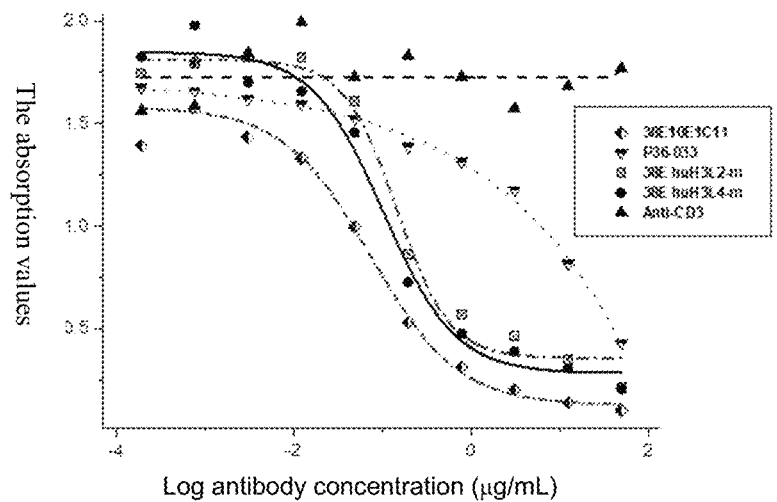
Figure 20:
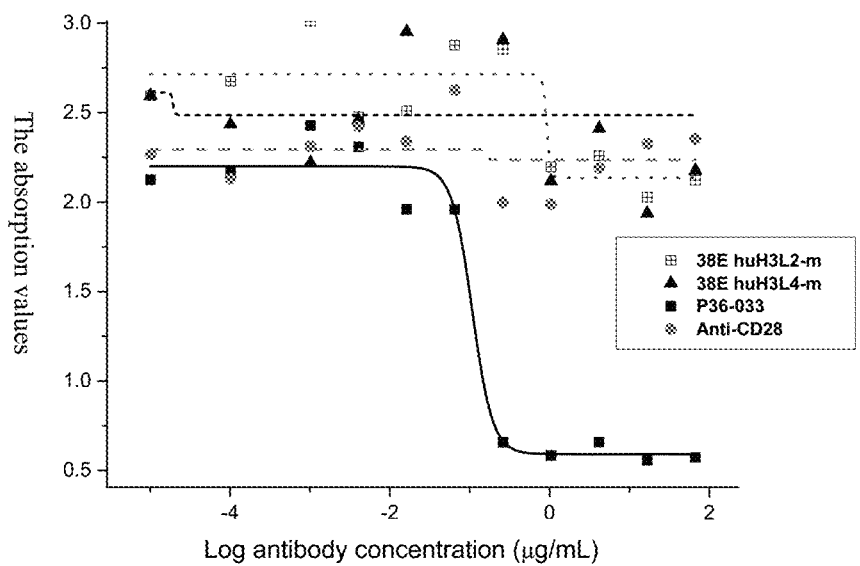
Figure 21:
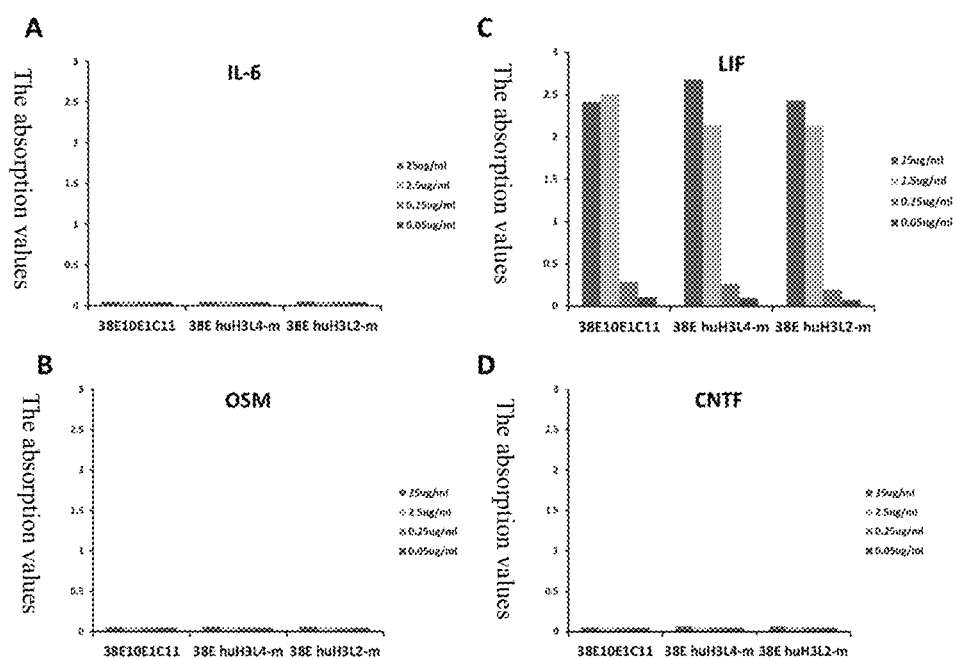
Figure 22:
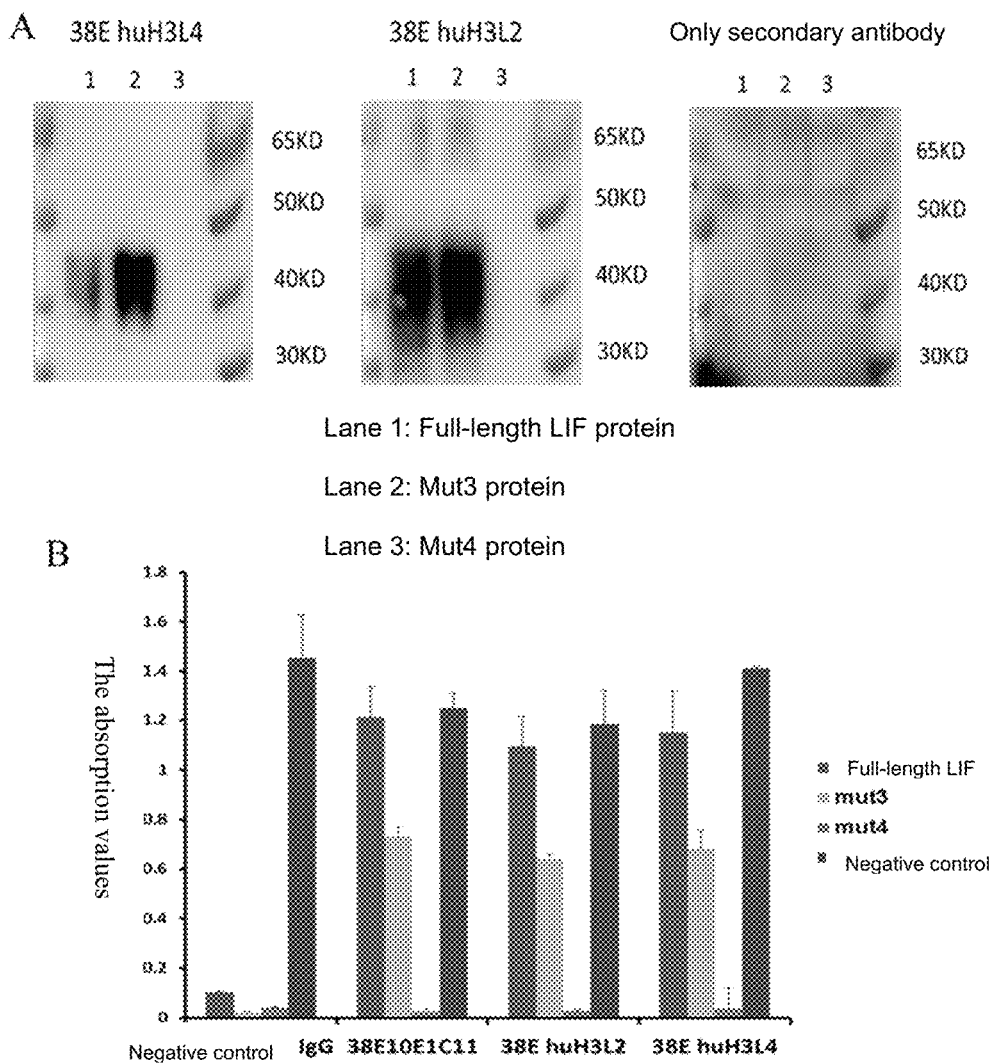
Figure 23:
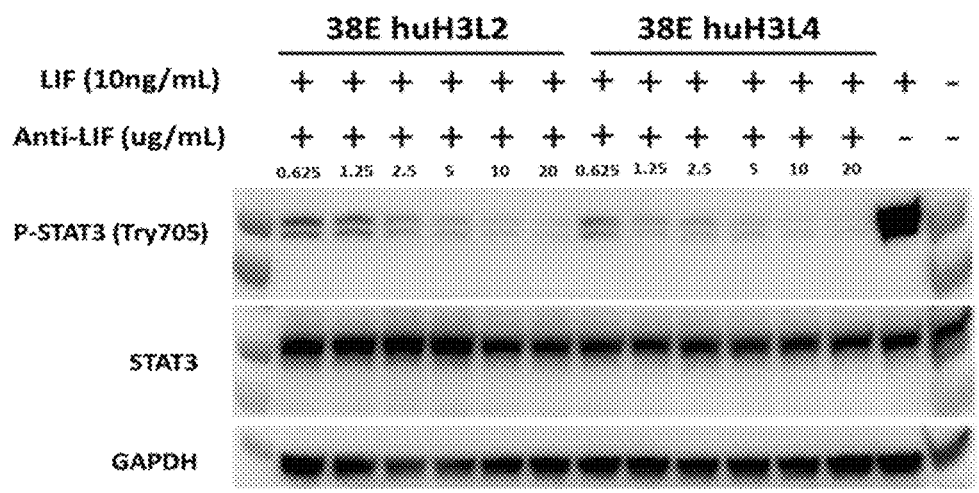
Figure 24:
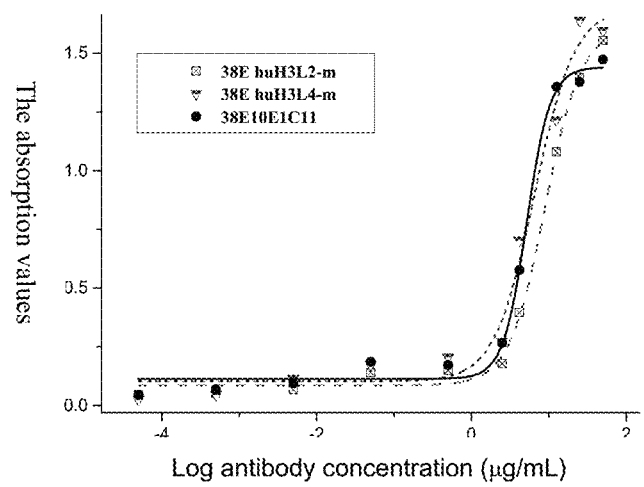

Subfigure A in FIG. 9 depicts that the 38E10E1C11 antibody of the invention inhibits the phosphorylation of colon cancer cells (HCT116) induced by human LIF protein; Subfigure B in FIG. 9 depicts that the 38E10E1C11 antibody of the invention inhibits the phosphorylation of STAT3 in pancreatic cancer cells (KP4) induced by human LIF protein;

FIG. 10 depicts that the 38E10E1C11 antibody of the invention blocks the activation of STAT3 in pancreatic cancer cells KP4 by human LIF secreted by CT26-hLIF cells;

FIG. 11 depicts that the P36-033 antibody of the invention inhibits the phosphorylation of STAT3 in colon cancer cells (HCT116) induced by human LIF protein;

FIG. 12 depicts that the 38E1E1C11 and P36-033 antibodies of the invention reverse the proliferation inhibition of M1 cells caused by LIF;

FIG. 13 depicts that the 38E1E1C11 antibody of the invention inhibits the growth of CT26-hLIF cells in BABL/c mice;

FIG. 14 depicts the sensitivity of three human pancreatic cancer cell lines to stimulation by human LIF protein;

FIG. 15 depicts that the 38E10E1C11R antibody of the invention inhibits the phosphorylation of STAT3 in KP4 cells stimulated by LIF protein;

Subfigure A in FIG. 16 depicts the experimental result of the recognition of full-length human LIF protein as well as heterozygous LIF protein by the 38E10E1C11 antibody of the invention, and Subfigure B in FIG. 16 depicts the experimental result that 38E10E1C11 antibody of the invention can reverse M1 cell proliferation inhibition caused by full-length human LIF protein and heterozygous LIF protein;

FIGS. 17A-FIG. 17D depict the experimental result of the antigen binding properties of the humanized anti-LIF antibody of the invention;

FIG. 18 depicts the experimental result of the non-specific binding affinity of the humanized anti-LIF antibody of the invention;

FIG. 19 depicts the experimental result of the humanized anti-LIF antibody of the invention competing with LIFR for binding human LIF protein;

FIG. 20 depicts the experimental result of the humanized anti-LIF antibody of the invention competing with GP130 to bind human LIF protein;

FIG. 21 depicts the experimental result of the humanized anti-LIF antibody of the invention recognizing antigen specificity;

Subfigure A in FIG. 22 depicts the experimental result of the humanized anti-LIF antibody of the present invention recognizing full-length human LIF proteins and heterozygous LIF proteins; and Subfigure B in FIG. 22 depicts the experimental result of the humanized anti-LIF antibody of the invention blocking the inhibition of M1 cells proliferation by full-length LIF protein and hybrid protein;

FIG. 23 depicts the experimental result of humanized anti-LIF antibody of the invention inhibiting the phosphorylation of STAT3 induced by LIF protein;

FIG. 24 depicts the experimental result that the humanized anti-LIF antibody of the invention can reverse the inhibition of M1 cell proliferation by human LIF protein.

Figure 25:
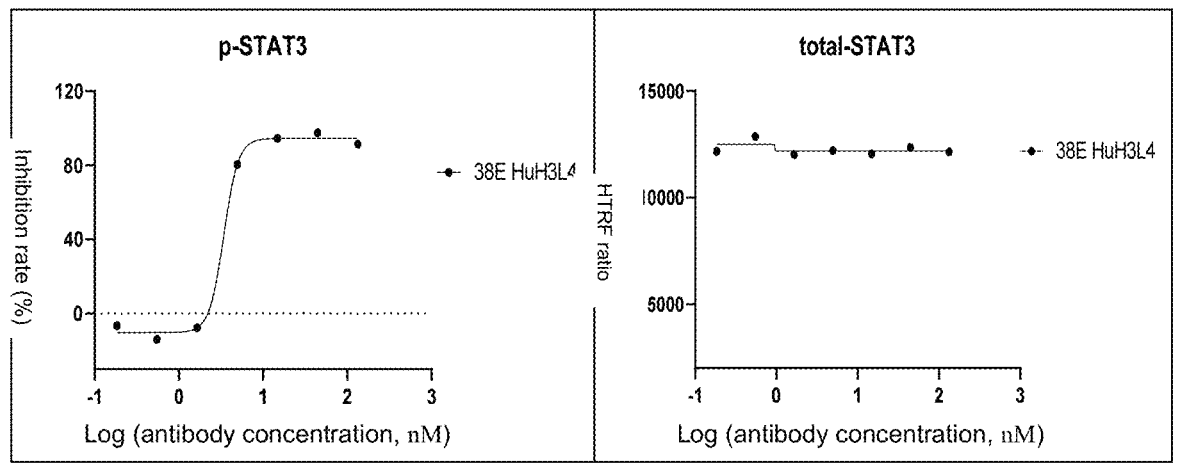

FIG. 25 depicts LIF protein-induced phosphorylation level of STAT3 inhibited by humanized anti-LIF antibody and total STAT3 level, detected by HTFR method.

Figure 26:
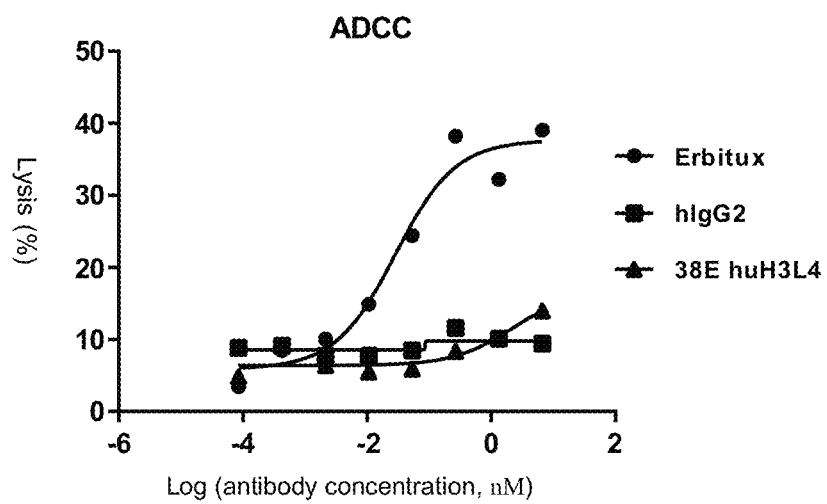

FIG. 26 depicts ADCC effect of humanized anti-LIF antibody.

DETAILED DESCRIPTION

Definitions

In order that the present description may be more readily understood, certain terms are first defined. Additional definitions are set forth throughout the detailed description.

The term "LIF" as used herein refers to leukemia inhibitory factor. The amino acid sequence of LIF is encoded by the nucleic acid sequence as shown in SEQ ID NO: 84 (which is publicly available through Ref Seq NM_001257135). In some embodiments, LIF can be human LIF, mouse LIF encoded by the nucleic acid sequence as shown in SEQ ID NO: 85 (which is publicly available through Ref Seq NM_001039537.2), or machin LIF encoded by the nucleic acid sequence as shown in SEQ ID NO: 86 (which is publicly available through XM_015457518.1). As described elsewhere herein, LIF can be recombinant and/or glycosylated or non-glycosylated.

The term "antibody" as used herein may include whole antibodies and any antigen binding fragments (i.e., "antigen-binding portions") or single chains thereof. An "antibody" refers, in one embodiment, to a glycoprotein or an antigen binding portion thereof comprising at least two heavy (H) chains and two light (L) chains inter-connected by disulfide bonds. Each heavy chain is comprised of a heavy chain variable region (abbreviated herein as VH) and a heavy chain constant region. In some naturally occurring IgG, IgD and IgA antibodies, the heavy chain constant region is comprised of three domains, CH1, CH2 and CH3. In some naturally occurring antibodies, each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), and regions that are more conserved, termed framework regions (FR), both of which are intermingled arrangement. Herein, the CDRs of the VH region are abbreviated as HCDR, that is, the three CDRs of the VH region can be abbreviated as HCDR1, HCDR2, and HCDR3; the CDRs of the VL region are abbreviated as LCDR, that is, the three CDRs of the VL region can be abbreviated as LCDR1, LCDR2. LCDR3. Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system (Clq).

The heavy chain of an antibody may or may not contain a terminal lysine (K), or a terminal glycine and lysine (GK). Thus, any of the heavy chain sequences and heavy chain constant region sequences provided herein can end in either GK or K, or lack K or GK, regardless of what the last amino acid of the sequence provides. This is because the terminal lysine and sometimes glycine and lysine are cleaved during expression of the antibody.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate binding nonspecifically. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% or greater sequence identity to the sequence of the given antigen.

An immunoglobulin may be from any of the commonly known isotypes, including but not limited to IgA, secretory IgA, IgG and IgM. The IgG isotype is divided in subclasses in some species: IgG1, IgG2, IgG3 and IgG4 in humans, and IgG1, IgG2a, IgG2b and IgG3 in mice. In certain embodiments, the anti-LIF antibodies described herein are of the human IgG1 or IgG2 subtype. Immunoglobulins, e.g., human IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody or "antigen-binding fragment" of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody, e.g., an anti-LIF antibody described herein, include (i) a Fab fragment, which is a monovalent fragment consisting of the VL, VH, CL and CH1 domains; (ii) a F(ab')2 fragment, which is a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) or (vii) a combination of two or more isolated CDRs which may optionally be linked by a synthetic linker. Furthermore, although the two domains of the Fv fragment, VL and VH, are encoded for by different genes, they can be linked, using recombinant methods, by a synthetic linker that enables them to be made as a single protein chain in which the VL and VH regions pair to form monovalent molecules known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These and other potential constructs are described at Chan & Carter (2010) Nat. Rev. Immunol. 10:301. These antibody fragments are obtained using conventional techniques known to those with skill in the art, and the fragments are screened for utility in the same manner as intact antibodies. Antigen-binding portions can be produced by recombinant DNA techniques, or by enzymatic or chemical cleavage of intact immunoglobulins.

The term "amino acid sequence of conservative modifications form" refers to the amino acid modifications that do not significantly affect or alter the binding characteristics of the antibody containing the amino acid sequence, and the modifications include amino acid substitutions, additions and deletions. Modifications can be introduced into an antibody of the invention by standard techniques, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein. Preferably, the conservative modifications are no more than one or two in number.

Modification of the amino acid sequences described herein is desirable in the invention, especially those human heavy chain constant regions to adapt the sequence to the desired allotype, such as those found in Asian populations.

For example, one or more CDRs or CDR groups of an antibody can be grafted into a framework (such as a human framework) to provide an antibody molecule. The framework regions can be human germline or non-germline gene sequences. In this way the framework can be germline, where one or more residues in the framework can be exchanged to match the residues in the most similar human germline framework at a comparable position. In this way, the binding member of the invention may be an isolated VH domain having a HCDR group within a human germline framework, for example, a human germline IgG VH framework. The binding member may also have a VL domain containing the LCDR group, such as in the human germline IgG VL framework.

The VH and/or VL scaffold residues can be modified as discussed, as exemplified herein, such as using site-directed mutagenesis. The VH or VL domains, or binding members of the invention include such VL domains.

Changes can be made in one or more framework regions and/or one or more CDRs, the changes usually do not result in a loss of function, so a binding member comprising such changed amino acid sequence should maintain the ability to bind and/or neutralize LIF. It can maintain the same number of binding and/or neutralizing capabilities as the binding members that have not changed, as measured by the analytical method described herein. A binding member comprising such changed amino acid sequence may have an improved ability to bind and/or neutralize LIF.

Changes can include the replacement of one or more amino acid residues with non-naturally occurring or non-standard amino acids, modifying one or more amino acid residues into a non-naturally occurring or non-standard form, or inserting one or more non-naturally occurring or non-standard amino acids into the sequence. Examples of the location and number of changes in the sequence of the invention are described elsewhere herein. Naturally occurring amino acids include the 20 "standard" L-amino acids identified as G, A, V, L, I, M, P, F, W, S, T, N, Q, Y, C, K, R, H, D, E by their standard one-letter codes. Non-standard amino acids include any other residues that can be incorporated into the polypeptide backbone or modified from existing amino acid residues. Non-standard amino acids can be naturally occurring or non-naturally occurring. Several naturally occurring non-standard amino acids are known in the art, such as 4-hydroxyproline, 5-hydroxylysine, 3-methylhistidine, N-ethylserine, etc. (Voet & Voet, 1995, Biochemistry, 2nd Edition, (Wiley)). Those amino acid residues derivatized at their N-α position will only be positioned at the N-terminus of the amino acid sequence. Generally, the amino acid in the invention is an L-amino acid, but it may be a D-amino acid. Therefore changes may include modification with L-amino acids or replacement of L-amino acids with D-amino acids. The formylated, acetylated and/or phosphorylated forms of amino acids are known, and the amino acids of the invention can be modified as such.

The amino acid sequences in the binding members and antibody domains of the invention may include the unnatural or non-standard amino acids described above. Non-standard amino acids (such as D-amino acids) can be incorporated into the amino acid sequence during synthesis, or by modification or substitution of "original" standard amino acids after amino acid synthesis.

The use of non-standard and/or non-naturally occurring amino acids improves the diversity of structure and function, and can increase the potential to achieve the desired LIF binding and neutralizing properties in the binding members of the invention. In addition, compared with standard L-amino acids, D-amino acids and their analogs have been shown to have better pharmacokinetic properties due to the degradation of polypeptides with L-amino acids in vivo after administration to animals such as humans.

The generation of the new VH or VL region with CDR-derived sequences of the invention can use one or more random mutagenesis selected from VH and/or VL genes to generate mutants in all the variant regions. Such technique is described in Gram et al. (Gram et al., 1992, Proc. Natl. Acad. Sci., USA, 89: 3576-3580), which uses error-prone PCR. In some embodiments, one or more amino acid substitutions are made in all variant regions or CDR groups.

Another method that can be used is targeted mutagenesis of the CDR regions of VH or VL genes. Such method is published by Barbas et al. (Barbas et al., 1994, Proc. Natl Acad. Sci., USA, 91: 3809-3813) and Schier et al. (Schier et al., 1996, J. Mol. Biol. 263: 551-567).

All the methods described above are known in the art, and those skilled in the art will be able to use such methods and adopt conventional methods in the art to provide binding members of the invention.

Any VH and VL domain amino acid sequence variants with the specific sequences disclosed herein can be used in accordance with the invention, as discussed. Specific variants may include one or more amino acid sequence changes (additions, deletions, substitutions and/or insertions of amino acid residues). In some embodiments, the variant has less than about 17, less than 9, or less than 5 such changes.

As shown above, the CDR amino acid sequence substantially as described herein can be carried as a CDR in a human antibody variant structure region or most of it. The HCDR3 sequence substantially as described herein represents an embodiment of the invention, each of these can be carried as a CDR in a human antibody variant region or most of it, optionally in combination with HCDR1, HCDR2, LCDR1, LCDR2, and LCDR3 of the invention.

The term "monoclonal antibody," as used herein, refers to an antibody that displays a single binding specificity and affinity for a specific epitope or a composition of antibodies in which all antibodies display a single binding specificity and affinity for a specific epitope. Typically such monoclonal antibodies will be derived from a single antibody encoding cell or nucleic acid, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell derived from a transgenic or transchromosomal non-human animal (e.g., a transgenic mouse having a genome comprising a human heavy chain transgene and a light chain transgene), with an immortalized cell. The term "mAb" refers to monoclonal antibodies.

The term "recombinant human antibody," as used herein, includes all human antibodies that are prepared, expressed, produced or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, produced or isolated by any other means that involve splicing of human immunoglobulin gene sequences to other DNA sequences. Such recombinant human antibodies comprise variable and constant regions that utilize specific human germline immunoglobulin sequences and are encoded by the germline genes, but include subsequent rearrangements and mutations that occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for a exogenous antigen. In addition to rearrangement, the variable region can be further modified by multiple single amino acid changes (referred to as somatic mutation or hypermutation) to increase the affinity of the antibody to the exogenous antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of an antibody in humanized form, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a specific antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The functional antibody fragments of the invention include any functional fragments whose half-life period is increased by chemical modification such as by PEGylation or incorporation into liposomes.

The antibodies of the invention include bispecific antibodies. Bispecific or bifunctional antibodies form second-generation monoclonal antibodies, in which two different variant regions are combined into the same molecule (Holliger and Bohlen, 1999 Cancer and metastasis rev. 18: 411-419). For their ability to recruit new effector functions or to target some molecules on the surface of tumor cells, their applications in the field of diagnosis and treatment have been elucidated. When bispecific antibodies are used, for example, hybridomas that are chemically prepared or derived from hybrid, can be conventional bispecific antibodies, which can be manufactured in various ways (HolligerP. & Winter G. Current Opinion Biotechnol. 4, 446-449: 1993), or can be any of the bispecific antibody fragments mentioned above. These antibodies can be obtained by chemical methods or somatic methods, but equally and preferably genetic engineering methods, which allow heterodimerization to be carried out, and facilitates the purification process of the obtained antibodies. Examples of bispecific antibodies include those of the BiTETM method, in which the binding domains of two antibodies with different specificities can be used and linked directly by a short flexible peptide. This combines two antibodies on a short single polypeptide chain. The diabody and scFc are constructed without the Fc region, only variant region is used, which potentially reducing the effect of the anti-idiotypic response.

Bispecific antibodies can be constructed as full IgG, bispecific (Fab')2, (Fab')PEG, diabody or other bispecific scFv. Furthermore, two bispecific antibodies can be linked to form a tetravalent antibody using conventional methods known in the art.

Compared with bispecific whole antibodies, bispecific diabodies are also particularly useful because they can be easily constructed and expressed in *E. coli*. Using a phage display library (WO1994/13804), diabodies (and many other polypeptides, such as antibody fragments) with appropriate binding specificity can be easily selected. If one arm of the diabody is kept constant, then a library is prepared, in which the other arms are mutated, and antibodies of appropriate specificity are selected. Bispecific whole antibodies can be prepared by different engineering methods, which are described in Ridgeway et al. (Ridgeway, J. B. B. et al., Protein Eng. 9, 616-621, 1996) or WO1996/27011, WO1998/50431 and WO2006/028936.

A "modified heavy chain constant region" refers to a heavy chain constant region comprising the constant domains CH1, hinge, CH2, and CH3, wherein one or more of the constant domains are from a different isotype (e.g. IgG1, IgG2, IgG3, IgG4). In some embodiments, the modified constant region includes a human IgG2 CH1 domain and a human IgG2 hinge fused to a human IgG1 CH2 domain and a human IgG1 CH3 domain. In certain embodiments, such modified constant regions also include amino acid modifications within one or more of the domains relative to the wildtype amino acid sequence.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants in a specific isotype group, which variants differ in a few amino acids (see, e.g., Jefferis et al. (2009) mAbs 1: 1). Antibodies described herein may be of any allotype.

Unless specified otherwise herein, all amino acid numbers are according to the EU index of the Kabat system (Kabat, E. A., et al. (1991) Sequences of Proteins of Immunological Interest, Fifth Edition, U.S. Department of Health and Human Services, NIH Publication No. 91-3242).

The terms "an antibody recognizing an antigen" and "an antibody specific for an antigen" are used interchangeably herein with the term "an antibody which binds specifically to an antigen."

The term "an isolated antibody," as used herein, is intended to refer to an antibody that is substantially free of other antibodies having different antigenic specificities (e.g., an isolated antibody that specifically binds to LIF is substantially free of antibodies that specifically bind antigens other than LIF). An isolated antibody that specifically binds to an epitope of LIF may, however, have cross-reactivity to other LIF proteins from different species.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated hagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating receptors (FcγRI, FcγRIII, and FcγRIV in mice; FcγRIA, FcγRIIA, and FcγRIIIA in humans) and one inhibitory receptor (FcγRIIB). Various properties of human FcγRs are summarized in Table A. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but does not express the inhibitory FcγRIIB in mice and humans. Human IgG1 binds to most human Fc receptors and is considered that the types of activating Fc receptors which it binds to are equivalent to murine IgG2a.

plary CH1 domains include CH1 domains with mutations that change a biological activity of an antibody, such as ADCC, CDC or half-life period.

The term "CH2 domain" refers to the heavy chain constant region linking the hinge in a heavy chain constant domain to the CH3 domain. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants thereof having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that change a biological activity of an antibody, such as ADCC, CDC or half-life period.

The term "CH3 domain" refers to the heavy chain constant region that is C-terminal to the CH2 domain in a heavy chain constant domain. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants thereof having 1, 2, 3, 4, 5, 1-3, 1-5, 3-5 and/or at most 5, 4, 3, 2, or 1 mutations, e.g., substitutions, deletions or additions. Exemplary CH3

TABLE A

Properties of human FcγRs

| Fcγ | Allelic variants | Affinity for human IgG | Isotype preference | Cellular distribution |
|---|---|---|---|---|
| FcγRI | None described | High (KD ~10 nM) | IgG1 = 3 > 4 >> 2 | Monocytes, macrophages, activated neutrophils, dentritic cells |
| FcγRIIA | H131 | Low to medium | IgG1 > 3 > 2 > 4 | Neutrophils, monocytes, macrophages, eosinophils, |
|  | R131 | Low | IgG1 > 3 > 4 > 2 | dentritic cells, platelets |
| FcγRIIIA | V158 | Medium | IgG1 = 3 >> 4 > 2 | NK cell, monocytes, |
|  | F158 | Low | IgG1 = 3 >> 4 > 2 | macrophages, mast cells, eosinophils, dentritic cell |
| FcγRIIB | I232 | Low | IgG1 = 3 = 4 > 2 | B cells, monocytes, |
|  | T232 | Low | IgG1 = 3 = 4 > 2 | macrophages, dentritic cells, mast cells |

A "hinge", "hinge domain" or "hinge region" or "antibody hinge region" refers to the domain of a heavy chain constant region that links the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions.

The term "hinge" includes wildtype hinges, as well as variants thereof (e.g., non-naturally-occurring hinges or modified hinges). For example, the term "IgG2 hinge" includes wildtype IgG2 hinge, and variants having 1, 2, 3, 4, 5, 1-3, 1-5, 3-5 and/or at most 5, 4, 3, 2, or 1 mutations, e.g., substitutions, deletions or additions.

The term "CH1 domain" refers to the heavy chain constant region linking the variable domain to the hinge in a heavy chain constant domain. The term "CH1 domain" includes wildtype CH1 domains, as well as variants thereof (e.g., non-naturally-occurring CH1 domains or modified CH1 domains). For example, the term "CH1 domain" includes wildtype CH1 domains and variants thereof having 1, 2, 3, 4, 5, 1-3, 1-5, 3-5 and/or at most 5, 4, 3, 2, or 1 mutations, e.g., substitutions, deletions or additions. Exemdomains include CH3 domains with mutations that change a biological activity of an antibody, such as ADCC, CDC or half-life period.

A "CL domain" refers to the constant domain of a light chain. The term "CL domain" includes wildtype CL domains and variants thereof.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al. (2009) mAbs 1: 1).

The term "epitope" or "antigenic determinant" refers to a site on an antigen (e.g., LIF) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained when exposing to denaturing solvents, whereas epitopes formed by tertiary folding are typically lost when treating with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation analysis, wherein overlapping or contiguous peptides (e.g., from LIF) are tested for reactivity with a given antibody (e.g., anti-LIF antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

Antibodies that "compete with another antibody for binding to a target" refer to antibodies that inhibit (partially or completely inhibit) the binding of another antibody to the target. Whether the two antibodies compete with each other for binding to a target, i.e., whether and to what extent one antibody inhibits the binding of another antibody to a target, may be determined using known competition experiments, such as those described in the Examples. In certain embodiments, an antibody competes with another antibody, and inhibits at least 10%, 20%, 30%, 40%, 50%, 60%, 70%, 80%, 90% or 100% of the binding. The extent of inhibition or competition may be different depending on which antibody is the "blocking antibody" (i.e., the cold antibody that is incubated first with the target). Competition assays can be conducted as described, for example, in Ed Harlow and David Lane, Cold Spring Harb Pro toe; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, the overlapping epitope or to the adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich analysis (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

The term "Kassoc" or "Ka", as used herein, is intended to refer to the association rate constant of a specific antibody-antigen interaction, whereas the term "Kdis" or "Kd" as used herein, is intended to refer to the dissociation rate constant of a specific antibody-antigen interaction. The term "$K_D$", as used herein, is intended to refer to the equilibrium dissociation constant, which is obtained from the ratio of Kd to Ka (i.e,. Kd/Ka) and is expressed as a molar concentration (M). $K_D$ values of antibodies can be determined using methods well established in the art. A preferred method for determining the $K_D$ of an antibody is to analyze by using surface plasmon resonance, preferably using a biosensor system such as a Biacore® surface plasmon resonance system or flow cytometry and Scatchard.

The term "EC50" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "IC50", in functional analysis, IC50 is the concentration of the binding member that can reduce the biological response to 50% of its maximum value, taking nM as the unit. In ligand-binding studies, IC50 is the concentration that reduces receptor binding to 50% of the maximum specific binding level. The IC50 can be calculated by plotting the percentage of the maximum biological activity response as a function of the log of the binding member concentration, and using a software program such as Origin (OriginLab Software Company, Northampton, Massachusetts, USA) to fit the S function to the data to generate the IC50 value. The potency is determined or measured using one or more analytical methods known to those skilled in the art and/or described or referenced herein. The neutralizing potency of the binding members can be expressed as the geomean.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be a single chain or a double chain, and may be cDNA. Also provided are "conservative sequence modifications" of the sequences set forth in SEQ ID NOs described herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial identity exists when the segments will hybridize under selective hybridization conditions, to the complement of the chain.

For polypeptides, the term "substantial identity" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The identity % between two sequences is a function of the number of identical positions shared by the sequences when the sequences are optimally aligned (i.e., identity %=number of identical positions/total number of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgap-dna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. (48):444-453 (1970)) which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform searches against public databases to, for example, identify related sequences. Such searches can be performed with the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences identical to the nucleic acid molecules described herein. BLAST protein searches can be performed with the XBLAST program, score=50, wordlength=3 to obtain amino acid sequences identical to the protein molecules described herein. To obtain gapped alignments for comparison purposes, Gapped BLAST can be used as described in Altschul et al., (1997) Nucleic Acids Res. 25(17):3389-3402. When using BLAST and Gapped BLAST programs, the default parameters of the respective programs (e.g., XBLAST and NBLAST) can be used. See ncbi.nlm.nih.gov.

These nucleic acids may be present in whole cells, in a cell lysate, or in a partially purified or substantially pure form. The nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For encoding sequences, these mutations may affect amino acid sequence as desired. Specifically, DNA sequences substantially identical to or derived from native V, D, J, constant, switches and other such sequences described herein are contemplated.

The term "vector," as used herein, is intended to refer to a nucleic acid molecule capable of transporting another nucleic acid to which it has been linked. One type of vector is "plasmid," which refers to a circular double chains DNA loop into which other DNA segments may be linked. Another type of vector is a viral vector, wherein other DNA segments may be linked into the viral genome. Some vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell when introduced into the host cell, and thereby are replicated along with the host genome. Moreover, some vectors are capable of directing the expression of genes to which they are operatively linked. Such vectors are referred to herein as "recombinant expression vectors" (or simply, "expression vectors"). In general, expression vectors used in recombinant DNA techniques are often in the form of plasmids. In the present description, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the specific subject cell but to the progeny of such a cell. Since certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be LIF or a fragment thereof.

As used herein, the terms "inhibition" or "blocking" (e.g., referring to inhibition/blocking of LIF binding or activity) are used interchangeably and encompass both partial and complete inhibition/blocking.

As used herein, "cancer" refers a broad group of diseases characterized by the uncontrolled growth of abnormal cells in the body. Since unregulated cell division may result in the formation of malignant tumors or cells, they would invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering from a recurrence of disease, inhibits the development or recurrence of the disease. The ability of a therapeutic or prophylactic agent to promote disease regression or inhibit the development or recurrence of the disease can be evaluated using a variety of methods known to those skilled in the art, such as in human subjects during clinical trials, in animal model systems predictive of efficacy in humans, or by assaying the activity of the agent in in-vitro assays.

The terms "patient" and "subject" refer to any human or non-human animal that receives either prophylactic or therapeutic treatment. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

EXAMPLES

Example 1 Screening and Identification of Anti-Human LIF Monoclonal Antibody 1.1 Preparation of Anti-Human LIF Monoclonal Antibody 38E10E1C11 by Hybridoma Method According to the monoclonal antibody preparation method (Kohler and Milstein (1975) Nature 256: 495), recombinant human LIF protein (purchased from Sino Biological) was used for immunizing BABL/c mice. 25 µg recombinant human LIF protein with an equal volume of Freund's complete adjuvant was used for the initial immunization by multiple subcutaneous injections of the back. After four weeks, Freund's incomplete adjuvant plus 25 µg of recombinant human LIF protein was used for the second immunization. Indirect ELISA method was used to detect the titer of antibody 20 days later. After 2-3 weeks interval, 50 µg of recombinant human LIF protein was injected intraperitoneally to strengthen the immunization. After 3 days, the animals were sacrificed and spleen cells were taken for fusion.

The mouse myeloma cells SP2/0 in logarithmic growth phase were taken for counting, and the spleen cell suspension of the immunized mouse was prepared. The spleen cells were fused with SP2/0 cells using 50% PEG according to conventional methods. The fused cells were added to a 96-well plate of trophoblast cells (six-week-old BABL/c mouse peritoneal macrophages), and were screened and cultured in DMEM with 1% HAT and 20% fetal bovine serum. When the clone was grown to ⅓ of the bottom of the plate, the culture supernatant was collected. ELISA plates were coated by recombinant human LIF protein, and indirect ELISA method was used for detecting of anti-LIF antibody in culture supernatant and screening clones secreting anti-human LIF antibody. Furthermore, a cell line stably secreting a high affinitive anti-human LIF monoclonal antibody was obtained by monoclonal antibodyization using limiting dilution, and the secreting antibody is labeled as 38E10E1C11. The full-length gene sequences encoding the light and heavy chains of the 38E10E1C11 antibody were determined as shown in SEQ ID NO:42 and SEQ ID NO:44, respectively, and the corresponding full-length amino acid sequences of the light and heavy chains of the 38E10E1C11 antibody were shown in SEQ ID NO:41 and SEQ ID NO:43, respectively; the gene sequences encoding the variable region of the light and heavy chains of the 38E10E1C11 antibody were shown in SEQ ID NO:76 and SEQ ID NO:77, respectively; and the corresponding amino acid sequences of the variable regions of the light and heavy chains of the 38E10E1C11 antibody are shown in SEQ ID NO:74 and SEQ ID NO:75. According to the Kabat system, the amino acid sequence of LCDR1 of 38E10E1C11 antibody was shown in SEQ ID NO: 1, the amino acid sequence of LCDR2 was shown in SEQ ID NO:2, the amino acid sequence of LCDR3 was shown in SEQ ID NO:3, the amino acid sequence of HCDR1 was shown in SEQ ID NO:4, and the amino acid sequence of HCDR2 was shown in SEQ ID NO:45, and the amino acid sequence of HCDR3 was shown in SEQ ID NO:6. The immunoglobulin type and subtype of the 38E10E1C11 antibody were identified (the result is IgG1 subtype, K type light chain).

After obtaining a hybridoma cell line capable of stably secreting antibodies, the cell was domesticated by the CD Hybridoma serum-free medium of thermo fisher and adapted to the serum-free suspension shake culture, and then the antibody was expressed and purified using the serum-free medium.

1.2 Preparation of Anti-Human LIF Monoclonal Antibody P36-033 by Phage Display Technology Recombinant human LIF protein was used for immunizing BABL/c mice. 25 µg recombinant human LIF protein with an equal volume of Freund's complete adjuvant was used for the initial immunization by multiple subcutaneous injections of the back. After four weeks, Freund's incomplete adjuvant plus 25 µg of recombinant human LIF protein is used for the second immunization. Indirect ELISA method was used to detect the titer of antibody 20 days later. After 2-3 weeks interval, 50 µg of recombinant human LIF protein was injected intraperitoneally to strengthen the immunization. After 3 days, the animals were sacrificed and spleen cells were taken for fusion. Total RNA from spleen cells was extracted using TRIZOL Reagent from Invitrogen Company and reverse transcribed to cDNA using Invitrogen cDNA Reverse Transcription Kit. The antibody gene was amplified by the degenerate primers of mouse light and heavy chain variable region and constructed into a phage display vector, and a phage antibody library was constructed. Thermo-automatic magnetic bead sorting system was used to elimination and selection of the phage antibody library, and the phage ELISA was used to select an *E. coli* clone capable of binding the recombinant human LIF protein, and the sequence of the antibody was determined. Furthermore, the P36-033 antibody was obtained by ELISA and cell viability identification. The full-length gene sequences of the P36-033 light chain and heavy chain are shown in SEQ ID NO:55 and SEQ ID NO:57, respectively, and the corresponding full-length amino acid sequences of the light chain and heavy chain of the P36-033 antibody are shown in SEQ ID NO:54 and SEQ ID NO:56, respectively; the gene sequence encoding the variable region of light chain and heavy chain of the P36-033 antibody are shown in SEQ ID NO:72 and SEQ ID NO:73, respectively, and the corresponding amino acid sequences of the variable region of the light and heavy chains of the P36-033 antibody are shown in SEQ ID NO: 82 and SEQ ID NO:83. According to Kabat system, the amino acid sequence of LCDR1 of the P36-033 antibody is shown in SEQ ID NO:66, the amino acid sequence of LCDR2 is shown in SEQ ID NO:67, the amino acid sequence of LCDR3 is shown in SEQ ID NO:68, the amino acid sequence of HCDR1 is shown in SEQ ID NO:69, the amino acid sequence of HCDR2 is shown in SEQ ID NO:70, the amino acid sequence of HCDR3 is shown in SEQ ID NO:71.

1.3 Expression and Purification of Positive Control Antibody 5D8

According to the report of the patent document of WO 2018/115960 A1, the antibody 5D8 is an antibody that inhibits the binding of LIF protein and GP130. According to the patent document, multiple gene sequences of the invention were synthesized, and different light and heavy chains are paired in different combinations to construct the full-length antibodies in the form of Human IgG1, and one of them with the best binding to LIF protein was found eventually, and meanwhile it was capable of blocking the recombinant human LIF protein binding with human GP130 and blocking the STAT3's phosphorylation in HCT116 cells by the recombinant human LIF protein through cell viability identification, therefore, the invention named it 5D8 as a positive control antibody in a follow-up trial. The full-length gene sequences encoding the heavy chain and light chain of the 5D8 antibody were determined as shown in SEQ ID NO:63 and SEQ ID NO:65, respectively, and the corresponding full-length amino acid sequences of the heavy chain and light chain of the 5D8 antibody were shown in SEQ ID NO:62 and SEQ ID NO:64, respectively; the gene sequences encoding the variable region of the 5D8 antibody were determined as shown in SEQ ID NO:80 and SEQ ID NO:81, respectively, and the corresponding amino acid sequences of the variable region of the heavy chain and the light chain of the 5D8 antibody are shown in SEQ ID NO: 78 and SEQ ID NO: 79, respectively.

Figure 1:
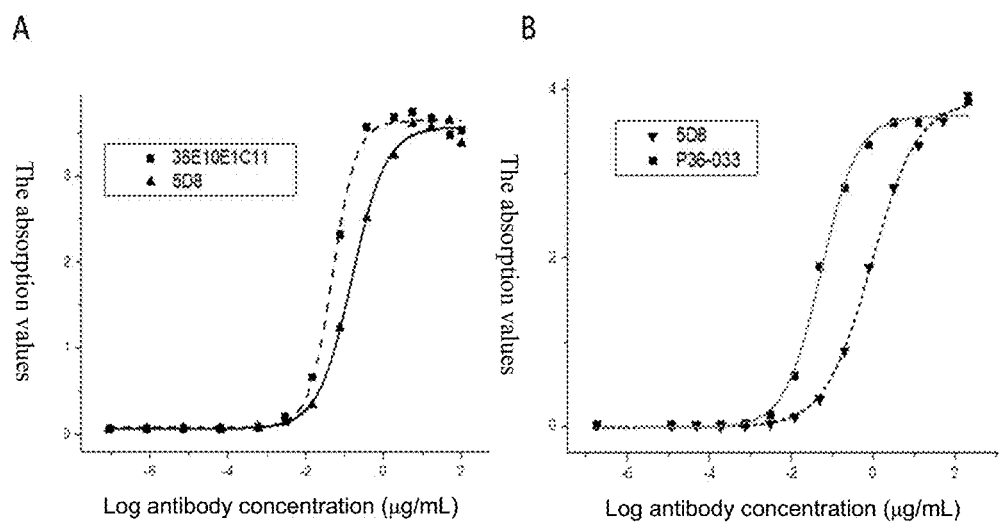
FIG. 1 depicts the binding ability of the LIF antibody of the invention to human LIF protein.

Example 2 The Binding Experiment of the Anti-Human LIF Antibody to Human LIF Protein The recombinant human LIF protein was diluted to 1 µg/mL, was coated on the enzyme label plate, 100 µL of the protein was added into every well, and incubated overnight in 4° C. The enzyme label plates were taken out next day, and the liquid was discarded, and were washed with PBST three times and blocked with 2% BSA in PBS for 1 h at room temperature, then washed with PBST three times, and added anti-human LIF antibodies 38E10E1C11, 5D8 and P36-033 at different concentrations and incubated for 1 h at room temperature. The liquid was discarded, and the plates were washed with PBST four times. The plates were added with HRP-labeled goat anti-mouse Fab antibody or goat anti-human FC antibody and incubated for 1 h at room temperature. Then the liquid was discarded, and the plates were washed four times with PBST and incubated with TMB colored solution in 10 minutes at room temperature. Stop color development by adding 2 mol/L $H_2SO_4$, and the absorption value at 450 nm is quantitated using an automated plate photometer, and the results were shown in FIG. 1. The results show that the binding of the 38E10E1C11 antibody and the P36-033 antibody to human LIF protein is stronger than the binding of the 5D8 antibody to human LIF protein.

Figure 2:
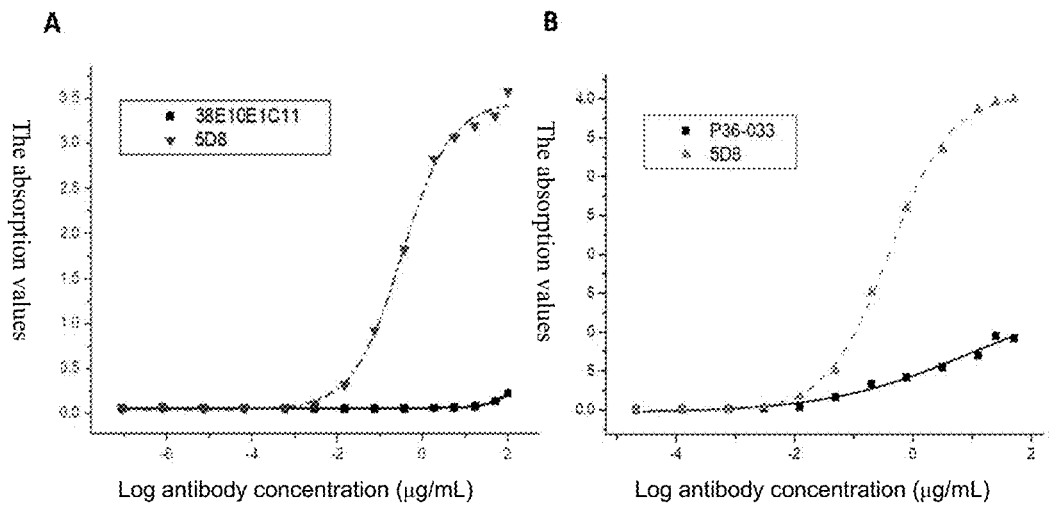
FIG. 2 depicts the binding ability of the LIF antibody of the invention to mouse LIF protein.

Example 3 The Binding Experiment of the Anti-Human LIF Antibody to Mouse LIF Protein The recombinant mouse LIF protein (purchased from ACRO Biosystems) was diluted to 1 µg/mL, and was coated on the enzyme label plate, 100 µL of protein was added into every well, and incubated overnight in 4° C. The enzyme label plates were taken out next day, and the liquid was discarded, and were washed with PBST three times and blocked with 2% BSA in PBS for 1 h at room temperature, then washed with PBST three times, and added anti-human LIF antibodies 38E10E1C11, 5D8 and P36-033 at different concentrations and incubated for 1 h at room temperature. The liquid was discarded, and the plates were washed with PBST four times. The plates were added with HRP-labeled goat anti-mouse Fab antibody or goat anti-human FC antibody and incubated for 1 h at room temperature. Then the liquid was discarded, and the plates were washed four times with PBST and incubated with TMB colored solution in 10 minutes at room temperature. Stop color development by adding 2 mol/L $H_2SO_4$, and the absorption value at 450 nm is quantitated using an automated plate photometer, and the results were shown in FIG. 2. The results show that the 38E10E1C11 antibody has no binding activity to the mouse LIF protein, and the P36-033 antibody has binding activity to the mouse LIF protein which is less than the 5D8 antibody.

Figure 3:
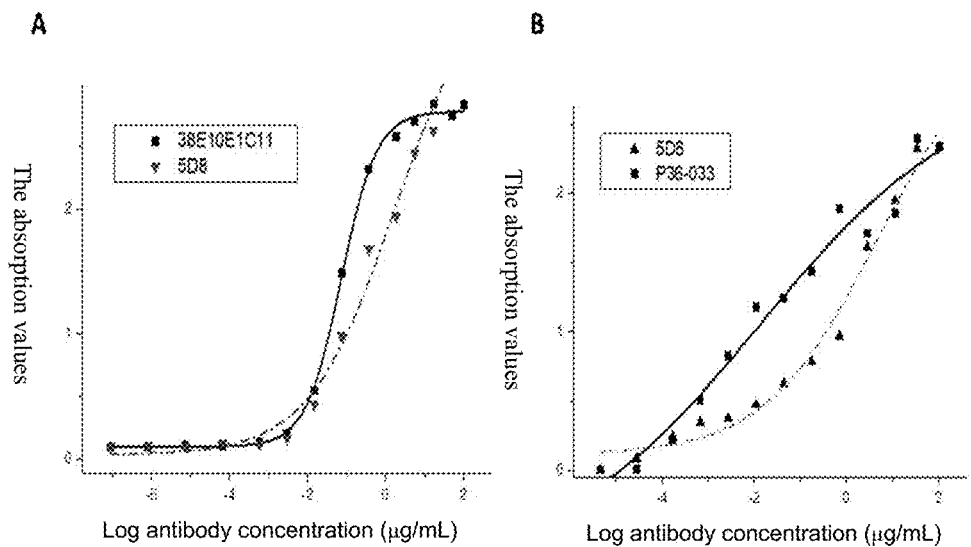
FIG. 3 depicts the binding ability of the LIF antibody of the invention to machin LIF protein.

Example 4 The Binding Experiment of the Anti-Human LIF Antibody to Machin LIF Protein The recombinant machin LIF protein (purchased from Sino biological) was diluted to 0.5 µg/mL, and was coated on the enzyme label plate, 100 µL of protein was added into every well, and incubated overnight in 4° C. The enzyme label plates were taken out next day, and the liquid was discarded, and were washed with PBST three times and blocked with 2% BSA in PBS for 1 h at room temperature, then washed with PBST three times, and added anti-human LIF antibodies 38E10E1C11, 5D8 and P36-033 at different concentrations and incubated for 1 h at room temperature. The liquid was discarded, and the plates were washed with PBST four times. The plates were added with HRP-labeled goat anti-mouse Fab antibody or goat anti-human FC antibody and incubated for 1 h at room temperature. Then the liquid was discarded, and the plates were washed with PBST four times and incubated with TMB colored solution in 10 minutes at room temperature. Stop color development by adding 2 mol/L $H_2SO_4$, and the absorption value at 450 nm is quantitated using an automated plate photometer, and the results were shown in FIG. 3. The results show that the binding activities of the 38E10E1C11 and the P36-033 are better than the binding activity of the 5D8.

Example 5 the Affinity Assay of the Anti-Human LIF Antibodies

Figure 4:
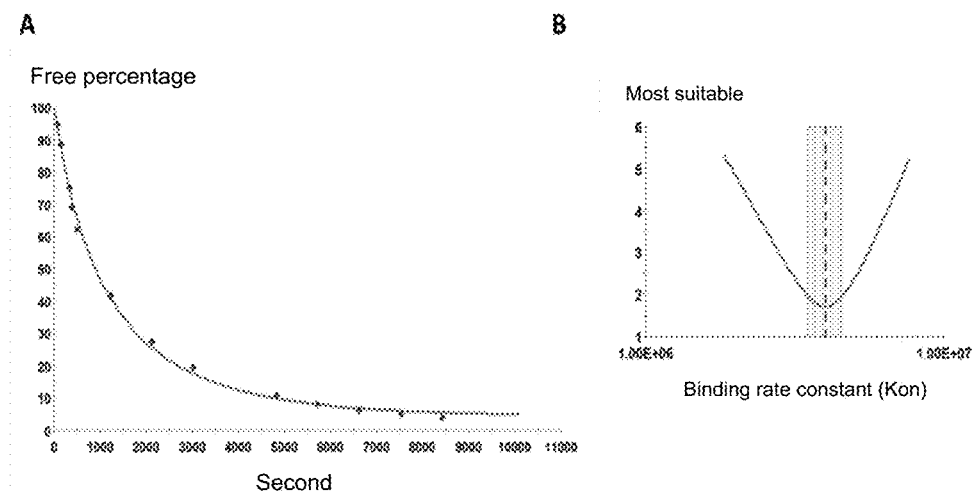
FIG. 4 depicts the affinity of the 38E10E1C11 antibody of the invention binding to the antigen.

The affinity of the purified monoclonal antibodies to the recombinant human LIF protein was determined by KinExA 4000. 200 mg PMMA hard beads were added with 30 µg of the 38E10E1C11 antibody and additional adding coating solution to 1 mL. The buffer composition is 1×PBS, pH 7.4, 0.02% NaN3. And make sure that the beads were completely suspended in the solution, and rotated for 2 h at room temperature. The beads were naturally settled or quickly centrifuged at low speed. The supernatant was removed and the beads were blocked with PBS containing 1% BSA. 15 mL of 300 pM antigen solution and 15 mL of 240 pM Ab2 (38E10E1C11) solution were prepared. 0.6 mL of 300 pM antigen and 0.6 mL of 240 pM antibody Ab2 (38E10E1C11) were put into different sample tubes separately. The samples in the two tubes were well mixed and put together into one tube, the concentration of the antigen was 150 pM and the concentration of antibody Ab2 (38E10E1C11) was 120 pM at this time, and the solution was placed in the corresponding position in the tube holder. 16 groups were prepared, and the incubation time of each group was different. Each group was added with 1 µg/Ll Streptavidin Protein, DyLight 650 Solution, and was detected on machine set to incubate for 24 hours. In the KinExatm Pro software, the equilibrium dissociation constant (Kd) for n-curve analysis was calculated by the unknown ligand model, and the results are shown in FIG. 4. The results show that the affinity of the 38E10E1C11 mAb to human LIF protein is $4.52 \times 10^{-12}$M.

Figure 5:
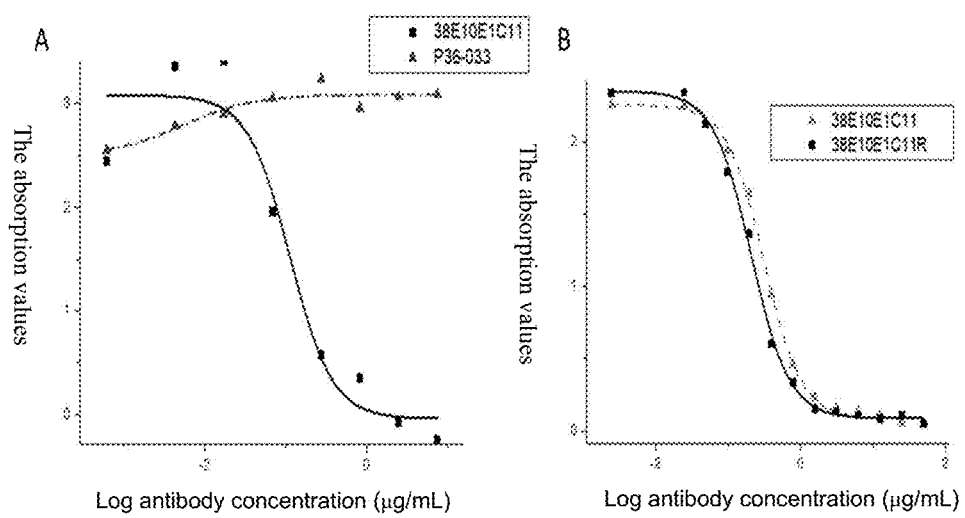
FIG. 5 depicts the ability of the 38E10E1C11 antibody of the invention competing with LIFR for binding to human LIF protein.

Example 6 the P36-033 mAB and the 38E10E1C11 mAb Compete with LIFR for Binding to Human LIF Protein The recombinant human LIF protein was coated on the enzyme label plate at a concentration of 1 µg/mL, LIFR protein (expressed fusedly with human FC) at a concentration of 0.6125 µg/mL was added (50 µL/well), and the anti-human LIF antibodies 38E10E1C11, P36-033 and 38E10E1C11R which is recombinantly expressed by CHO cells (SEQ ID NOs: 41 and 43) at different concentrations simultaneously were added separately (50 µL/well) and incubated for 2 h at room temperature. After washed four times with PBST, incubated with HRP-labeled goat anti-mouse FC secondary antibody for 1 h at room temperature. Then the plates were washed four times with PBST and added with TMB coloured solution in for 10 minutes. The absorption value at 450 nm is quantitated using an enzyme-labelling measuring instrument, and the data was analyzed and plotted using Origin pro 9 software. The results were shown in FIG. 5. The results show that the 38E10E1C11 mAb and 38E10E1C11 can inhibit the binding of human LIF to human LIFR, while the P36-033 mAb can't inhibit the binding of human LIF to human LIFR.

Figure 6:
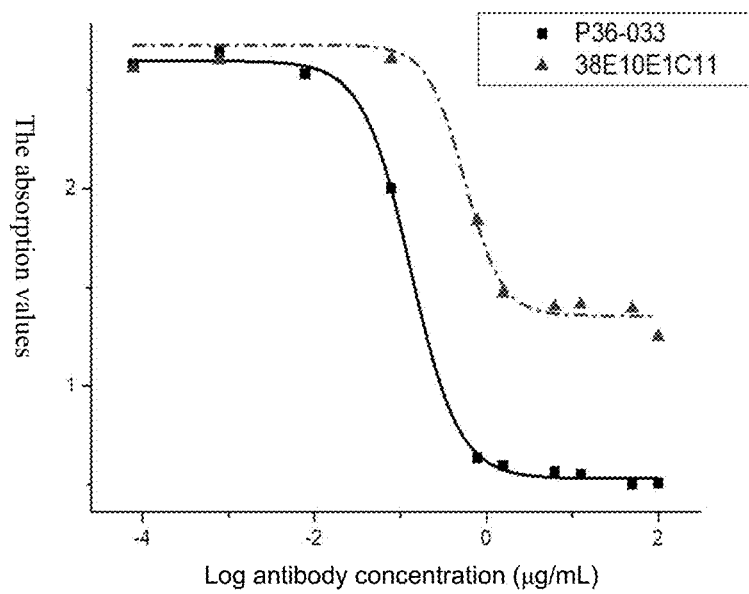
FIG. 6 depicts the ability of the P36-033 antibody competing with GP130 receptor for binding to human LIF protein.

Example 7 the P36-033 mAB and the 38E10E1C11 mAb Compete with GP130 for Binding to Human LIF Protein The recombinant human LIF protein was coated on the enzyme label plates at a concentration of 1 µg/mL, GP130 protein (expressed fusedly with human FC) at a concentration of 20 µg/mL was added (50 µL/well), and the anti-human LIF antibodies P36-033 and 38E10E1C11 at different concentrations simultaneously were added separately (50 µL/well), and incubated for 2 h at room temperature. At the same time, the control wells added with antibodies and without GP130 protein were set. Incubated for 2 h at room temperature. After washed four times with PBST, incubated with HRP-labeled goat anti-mouse FC secondary antibody for 1 h at room temperature. Then the plates were washed four times with PBST and added with TMB coloured solutionin for 10 minutes. The absorption value at 450 nm is quantitated using an enzyme-labelling measuring instrument, and the data was analyzed and plotted using Origin pro 9 software. The results were shown in FIG. 6. The results show that the P36-033 and the 38E10E1C11 can inhibit the binding of human LIF to human GP130 protein.

Example 8 Detection of the Specificity of 38E10E1C11 mAb

Figure 7:
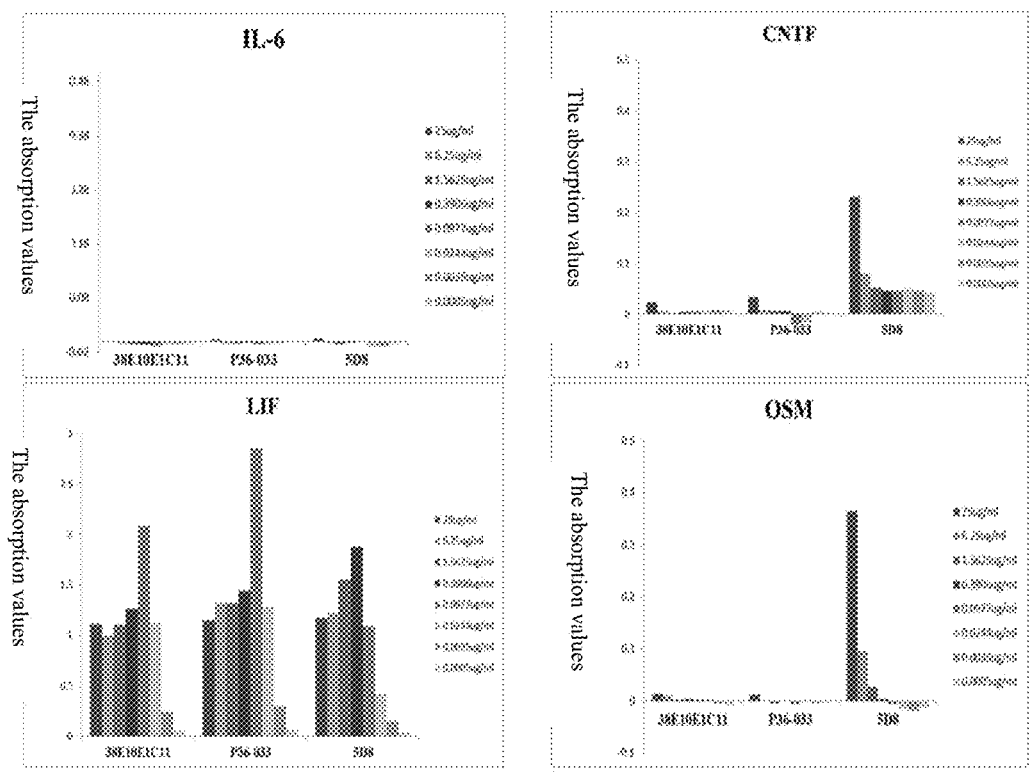
FIG. 7 depicts the cross-reaction of the 38E10E1C11 antibody and the P36-033 antibody of the invention with the IL-6 family protein.

The human LIF, human IL-6, human OSM, human CNTF (purchased from Sino biological) were coated on the enzyme label plate at a concentration of 1 µg/mL separately, and the anti-human LIF antibodies 38E10E1C11, P36-033 and 5D8 at different concentrations were added separately and incubated for 1 h at room temperature. Then the plates were washed four times with PBST and incubated with HRP-labeled goat anti-mouse FC secondary antibody for 1 h at room temperature. Then the plates were washed four times with PBST and added with TMB colored solution for color development at room temperature for 10 minutes. The absorption value at 450 nm is quantitated by the enzyme-labeling measuring instrument, and the data was analyzed and plotted using Origin pro 9 software. The results were shown in FIG. 7. The results show that the 38E10E1C11 mAb and the P36-033 mAb only bound to human LIF protein and didn't bind to human IL-6, human OSM and human CNTF, while the 5D8 antibody bound to human OSM and human CNTF protein.

Figure 8:
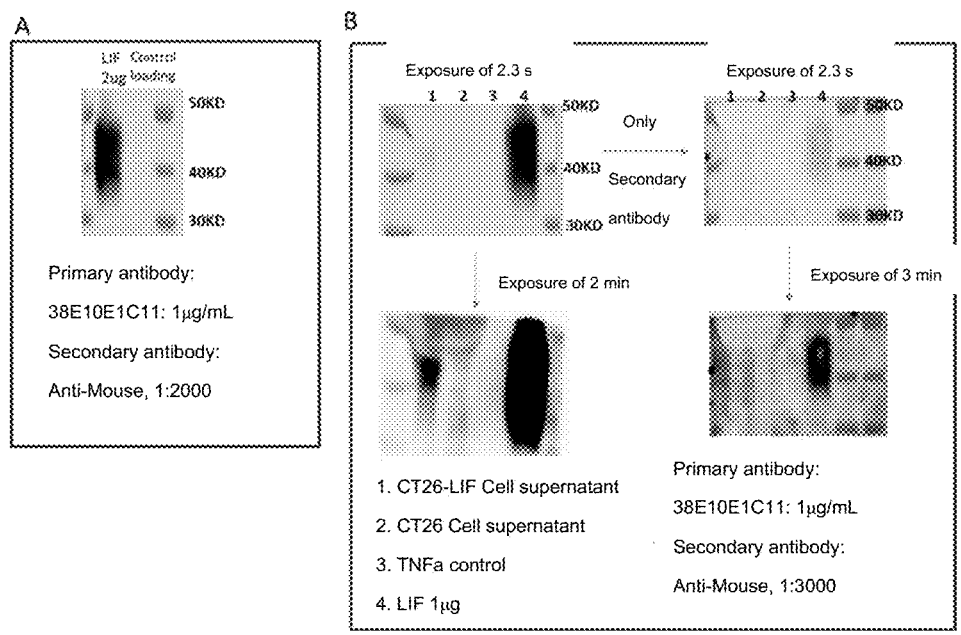
FIG. 8 depicts that the 38E10E1C11R antibody of the invention recognizes denatured human LIF protein.

Example 9 the Western Blot Detection that 38E10E1C11 mAb can be Used for Human LIF Protein The recombinant human LIF protein was diluted to the concentration shown in FIG. 8,. the cell supernatant of CT26 and C26-hLIF cells cultured for three days with 5XSDS-PAGE loading buffer was boiled for 10 minutes. 10 µL sample was taken for SDS-PAGE electrophoresis, and then the electrophoresis band was transferred to PVDF membrane for western blot detection, the primary antibody used for detection is 38E10E1C11 antibody at the concentration of 1 µg/mL, incubated for 2 h at room temperature, and washed three times by TBST buffer. Then adding 1:3000 diluted HRP-labeled goat anti-mouse secondary antibody, and incubated for 2 h at room temperature, incubated for 2 h at room temperature, and washed three times by TBST buffer. Then incubated with enhanced chemiluminescence solution (Perice), and detected and photographed by the Amersham Imager 600 ultra-sensitive multi-function imager. The results were shown in FIG. 8. The results show that the 38E10E1C11 mAb can be used for western blot detection of human LIF protein.

Example 10 Anti-Human LIF Antibody Cell Activity Assay 10.1 Detection of Inhibiting STAT3 Activation in HCT116 Cells HCT116 cells were digested and centrifuged, then the cells were resuspended and plated at 12-well plate in a volume of 1 mL with $5 \times 10^5$ cells/well. Then the cells were incubated at 37° ° C., 5% $CO_2$ overnight. The original medium was discarded next day, and the cell culture medium containing 100 ng/ml of recombinant human LIF protein and anti-LIF antibodies in different concentrations were added and incubated for 30 minutes at 37° ° C., and at the same time the control wells containing no recombinant human LIF protein and only recombinant human LIF protein without antibodies were set. The medium was then removed and 100 μL 1× lysate was added to each well of the 12-well plate, and the cells were lysed on ice for 30 min. The lysate was transferred to a 1.5 mL centrifuge tube, and the tube with lysate was centrifuged at 13,000 rpm for 10 min, and the supernatant was collected. The supernatant was taken for western blot detection of the phosphorylation of STAT3. The results were shown in Subfigure A in FIG. 9 and FIG. 11. From the results, it was revealed that the 38E10E1C11 antibody and the P36-033 antibody can inhibit the phosphorylation of STAT3 in HCT116 cells induced by human LIF protein.

10.2 Detection of the Activity of the Anti-Human LIF Antibodies Through the Test of Inhibiting STAT3 Activation in KP4 Cells KP4 cells were digested and centrifuged, and the cells were resuspended and plate at 12-well plate in a volume of 1 mL with $5 \times 10^5$ cells/well. Then the cells were incubated at 37° C., 5% $CO_2$ overnight. The original medium was discarded next day, and the cell culture medium containing 50 ng/mL of recombinant human LIF protein and anti-LIF antibodies in different concentrations were added and incubated for 30 minutes at 37° C., and at the same time the control wells containing no recombinant human LIF protein and only recombinant human LIF protein without antibodies were set. The medium was then removed and 100 μL 1× lysate was added to each well of the 12-well plate, and the cells were lysed on ice for 30 min. The lysate was transferred to a 1.5 mL centrifuge tube, and the tube with lysate was centrifuged at 13,000 rpm for 10 min, and the supernatant was collected. The supernatant was taken for western blot detection of the phosphorylation of STAT3. The results were shown in Subfigure B in FIG. 9, it shows that the 38E10E1C11 antibody can inhibit the phosphorylation of STAT3 in KP4 cells induced by human LIF protein.

10.3 Detection of the Activity of the Anti-Human LIF Antibodies Through the Test of Inhibiting STAT3 Activation in KP4 Cells KP4 cells were digested and centrifuged, and the cells were resuspended and plate at 12-well plate in a volume of 1 mL with $5 \times 10^5$ cells/well. Then the cells were incubated at 37° C., 5% $CO_2$ overnight. The original medium was discarded next day, and the anti-LIF antibodies in different concentrations and the cell culture medium of CT26-hLIF cells in a volume ratio of 1:1 was added and incubated for 30 minutes at 37° C., and at the same time the control wells containing the culture supernatant of CT26 were set. The medium was then removed and 100 μL 1× lysate was added into the cells, and the cells were lysed on ice for 30 min. The lysate was transferred to a 1.5 mL centrifuge tube, and the tube with lysate was centrifuged at 13,000 rpm for 10 min, and the supernatant was collected. The supernatant was taken for western blot detection of the phosphorylation of STAT3. FIG. 10 shows that the 38E10E1C11 antibody can inhibit the phosphorylation of STAT3 in KP4 cells induced by human LIF protein secreted by the CT26-hLIF cells.

10.4 Detection of LIF Antibody Activity Through the Test of M1 Cell Proliferation M1 cells were centrifuged and washed twice by RPMI1640 medium, the M1 cells were plated into 96-well plate in a volume of 100 μL cell per well at a density of $2 \times 10^5$ cells/mL. The cell culture medium containing 10 ng/ml of recombinant human LIF protein and anti-LIF antibodies in different concentrations were added until the volume of every well reached 200 μL finally and incubated for 72 h at 37° C. in the incubator. At the same time, the control wells without human LIF protein were set. CCK-8 was added to measure cell proliferation. The results were shown in FIG. 12, and the results show that both the mAb38E10E1C11 mAb and the P36-033 mAb can reverse the inhibition induced by human LIF protein of the proliferation of M1 cells,.

Example 11 Detection of Anti-Tumor Activity of Anti-Human LIF Antibody In Vivo

The 38E10E1C11 antibody did not cross-react with the mouse LIF protein by ELISA assay. In order to carry out the activity evaluation in vivo, CT26 cell line overexpressing human LIF protein needed to be constructed. According to the literature, human LIF protein is able to bind to the LIFR and GP130 on the surface of mouse cells, thereby activating the downstream signal. Therefore, it was speculated that human LIF protein secreted by CT26 cells which expressed human LIF protein highly can inhibit the immune system of mice, and the anti LIF protein can release the inhibitory effect and thus exert an anti-tumor effect.

11.1 Establishment of CT26 Cell Line Overexpressing Human LIF—

The mouse colon cancer cell line CT26 was infected with the constructed lentivirus containing human LIF gene. The expression of LIF protein was detected after 48 h. The cell line was cloned by limiting dilution method, and the medium with puromycin in the final concentration of 1 μg/mL was added for pressurized screening. Finally CT26 cell line stably and highly expressing human LIF protein was obtained.

11.2 Anti-Tumor Activity of Anti-Human LIF Antibody Detected by CT26-hLIF BABL/C Subcutaneous Implantation Model CT26-hLIF cells were cultured in RPMI-1640 medium containing 10% fetal bovine serum, collecting the cells in the logarithmic growth phase, resuspended in PBS to $10^7$ cells/mL, and inoculate BABL/c mice subcutaneously. One day after the inoculation, the mice were divided into groups and injected with vehicle control, anti-human LIF antibody respectively, the administration concentration is 15 mg/kg body weight, twice a week, for 4 consecutive weeks, the tumor volume is measured twice a week, the tumor growth curve is drawn, and the tumor inhibition rate is calculated. The results were shown in FIG. 13. The results show that the 38E10E1C11 mAb can inhibit CT26-hLIF cells proliferate in BABL/c mice.

11.3 Measurement of the Sensitivity of Different Pancreatic Cancer Cell Lines to the Stimulation of LIF Protein The human pancreatic cancer cell lines Panc02.03, KP4, MIA paca2 were inoculated into 6-well plate with a density of $10^6$ cell/well separately. The medium was replaced with the fresh medium after overnight incubated, and 50 ng/ml recombinant human LIF protein and the 38E10E1C11 antibody were added, meanwhile the control wells without LIF protein were set. The treatment wells and the control wells were incubated at 37° C. for 30 minutes. The medium was then removed and 200 μL 1× lysate was added to the cells of 200 μL for each well, and the cells were lysed on ice for 30 min. The lysate was transferred to a 1.5 mL centrifuge tube, and the tube with lysate was centrifuged at 13,000 rpm for 10 min, and the supernatant was collected. The supernatant was taken for western blot detection of the phosphorylation of STAT3. The results were shown in FIG. 14. The results show that KP4 cell line is most sensitive to the stimulation of human LIF protein.

Example 12 Recombinant Expression and Verification of the 38E10E1C11 mAb Antibody and the P36-033 mAb The light chain gene and the heavy chain gene of the 38E10E1C11 mAB and the P36-033 mAb were constructed into the eukaryotic expression vector PCDNA3.1+ by identical recombination technique. The recombinant antibodies were expressed by Thermo's ExpiCHO expression system, and the recombinant antibodies were purified by Protein G affinity chromatography. Endotoxin removal of the purified antibodies is carried out using Endotoxin Removal Beads produced by Smart-lifesciences company. The specific experimental method referred to Example 10.2. FIG. 15 shows that the 38E10E1C11 antibody (labeled as 38E10E1C11R) recombinantly expressed by CHO cells was capable of inhibiting phosphorylation of STAT3 in KP4 cells induced by human LIF protein.

Example 13 Identification of Epitope Recognized by 38E10E1C11 Antibody

It was confirmed by the preliminary experiments that the 38E10E1C11 antibody (SEQ ID NOs: 41 and 43) recognized the linear epitope on the surface of human LIF protein (SEQ ID NO: 58). The antibody could not recognize mouse LIF protein, and could block the binding of human LIF protein and human LIFR protein. According to these three points, combined with the analysis of a variety of online protein linear epitope prediction software, it was speculated that the recognition epitope of the antibody was located in the 160-202amino acid sequence of LIF protein, so the invention synthesized the following heterozygous LIF protein. Mut3(SEQ ID NO: 59) is to replace the 182-202 amino acid sequence of human LIF protein with that of mouse LIF protein, mut4 (SEQ ID NO: 60) is to replace the166-202 amino acid sequence of human LIF protein with that of mouse LIF protein. The plasmids containing mut3, mut4 and full-length human LIF protein were transfected into 293T cells. After three days of culture, the culture supernatant of 293T cells was taken for SDS-PAGE electrophoresis and western blot. The culture supernatant of 293T cells was used as negative control, 38E10E1C11 as primary antibody and HRP labeled Goat anti-mouse Fab as secondary antibody. At the same time, the M1 cell proliferation experiment was used to detect the activity of the hybrid protein and verify the neutralizing activity of 38E10E1C11 to the hybrid protein. Set up multiple groups of control wells at the same time, control wells adding human recombinant LIF protein (rhLIF, purchased from Yiqiao Shenzhou, the product number is: 14890-HNAH), control wells adding rhLIF and 38E10E1C11, and control wells without adding rhLIF and LIF antibody. The results showed that the 38E10E1C11 antibody could recognize the denatured full-length LIF protein and mut3 protein, but could not recognize mut4 protein (Subfigure A in FIG. 16). The M1 cell proliferation experiment shows that 38E10E1C11 antibody can reverse the inhibition of the full-length LIF protein and Mut3 protein on the proliferation of M1 cells but cannot reverse the inhibitory effect of the Mut4 protein (Subfigure B in FIG. 16). In summary, the recognition epitope of 38E10E1C11 antibody was located in the167-181 amino acid sequence of human LIF protein, that is, the amino acids TYGPDTSGKDVFQKK (SEQ ID NO:61).

Example 14 Design and Expression Purification of Humanized LIF Antibody

Monoclonal antibody 38E10E1C11 obtained from mouse immunization was humanized. Humanization was performed by standard CDR grafting method. The heavy and light chain regions were cloned from 38E10E1C11 hybridoma by standard molecular cloning techniques and sequenced by Sanger method. BLAST searches were then performed on the human heavy and light chain variable sequences and three or four sequences were selected as the receptor frames for humanization. The heavy and light chain CDR1, CDR2 and CDR3 of 38E10E1C11 were cloned into three different heavy chain receptor frames (H1-H3) and four different light chain frames (L1-L4), while the HCDR2 of 38E10E1C11 (amino acid sequence before mutation as shown in SEQ ID NO:45) was point mutated (the mutated amino acid sequence as shown in SEQ ID NO:5), the human IgG1 isoform was selected for the heavy chain constant region and the human kappa chain was selected for the light chain constant region. 293S cells were co-transfected with expression vectors containing the gene of the humanized antibody heavy chain and the humanized antibody light chain. The gene sequences of the heavy and light chain variable region, the amino acid sequence of the variable region, the full-length gene sequence and the full-length amino acid sequence were shown in Table 1. The expression levels, antigen binding ability and thermal stability of the twelve different antibodies combinations in 293S cells were then examined. The 38E10E1C11 chimeric antibody (Chimeric) was used as a positive control, and all 38E10E1C11 chimeric antibodies were abbreviated as 38E chimeric antibody or 38E Chimeric (SEQ ID NO: 52 and SEQ ID NO:50) in subsequent assays. The medium was collected and the expression levels of IgG therein were quantified on a Gator (similar to Octet) and corrected by ELISA. The antigen binding ability of the different combinations was compared by ELISA (Table 2, Table 3)

Enzyme Linked Immunosorbent Assay (ELISA):

Each well was coated with 100 µL of 0.5 µg/ml antigen and incubate overnight at 4° C., and the plates were washed three times with 300 µL of Wash Buffer. The plates were closed with 200 µL of Closure Buffer (2% bovine serum albumin) for 60 min at room temperature. The plates were washed three times with 300 µL of Wash Buffer. 100 µL of diluted anti-LIF antibody at different concentrations was added to each well and incubate for 1 hour at room temperature. The plates were washed 4 times with 300 µL of Wash Buffer. 100 µL of HRP-labeled goat anti-human Fc secondary antibody at a dilution of 1:5000 was added and incubate for 1 hour at room temperature. The plates were washed 6 times with 300 µL of Wash Buffer. 100 µL of $H_2O_2$-Amplx Color Development Solution was added for developing the color for 10 min at room temperature under dark conditions. The OD 450 value was read by an enzyme marker. Heat treatment: the expression medium was heated on the PCR machine at 70° C. for 5 min and then rapidly cooled to room temperature. Perform subsequent ELISA assays as above.

TABLE 1

Expression levels of different combinations of humanized light and heavy chains in 293S cells

| No. | | Gene sequence of variable region of humanized antibody | Amino acid sequence of variable region of humanized antibody | Full length gene sequence of humanized antibody | Full length amino acid sequence of humanized antibody | antibody concentration in culture supernatant (μg/ml) |
|---|---|---|---|---|---|---|
| H1L1 | heavy chain | SEQ ID NO: 24 (VH1,nt) | SEQ ID NO: 23 (VH1,aa) | SEQ ID NO: 26 (full heavy chain 1,nt) | SEQ ID NO: 25 (full heavy chain 1,aa) | 95.5 |
| | light chain | SEQ ID NO: 8 (VL1,nt) | SEQ ID NO: 7 (VL1,aa) | SEQ ID NO: 10 (full light chain 1,nt) | SEQ ID NO: 9 (full light chain 1,aa) | |
| H2L1 | heavy chain | SEQ ID NO: 28 (VH2,nt) | SEQ ID NO: 27 (VH2,aa) | SEE ID NO: 30 (full heavy chain 2,nt) | SEQ ID NO: 29 (full heavy chain 2,aa) | 120 |
| | light chain | SEQ ID NO: 8 (VL1,nt) | SEQ ID NO: 7 (VL1,aa) | SEQ ID NO: 10 (full light chain 1,nt) | SEQ ID NO: 9 (full light chain 1,aa) | |
| H3L1 | heavy chain | SEQ ID NO: 32 (VH3,nt) | SEQ ID NO: 31 (VH3,aa) | SEQ ID NO: 34 (full heavy chain 3,nt) | SEQ ID NO: 33 (full heavy chain 3,aa) | 108 |
| | light chain | SEQ ID NO: 8 (VL1,nt) | SEQ ID NO: 7 (VL1,aa) | SEQ ID NO: 10 (full light chain 1,nt) | SEQ ID NO: 9 (full light chain 1,aa) | |
| H1L2 | heavy chain | SEQ ID NO: 24 (VH1,nt) | SEQ ID NO: 23 (VH1, aa) | SEQ ID NO: 26 (full heavy chain 1,nt) | SEQ ID NO: 25 (full heavy chain 1,aa) | 110 |
| | light chain | SEQ ID NO: 12 (VL2,nt) | SEQ ID NO: 11 (VL2,aa) | SEQ ID NO: 14 (full light chain 2,nt) | SEQ ID NO: 13 (full light chain 2,aa) | |
| H2L2 | heavy chain | SEQ ID NO: 28 (VH2,nt) | SEQ ID NO: 27 (VH2,aa) | SEQ ID NO: 30 (full heavy chain 2,nt) | SEQ ID NO: 29 (full heavy chain 2,aa) | 89.4 |
| | light chain | SEQ ID NO: 12 (VL2,nt) | SEQ ID NO: 11 (VL2,aa) | SEQ ID NO: 14 (full light chain 2,nt) | SEQ ID NO: 13 (full light chain 2,aa) | |
| H3L2 | heavy chain | SEQ ID NO: 32 (VH3,nt) | SEQ ID NO: 31 (VH3,aa) | SEQ ID NO: 34 (full heavy chain 3,nt) | SEQ ID NO: 33 (full heavy chain 3,aa) | 95.3 |
| | light chain | SEQ ID NO: 12 (VL2,nt) | SEQ ID NO: 11 (VL2,aa) | SEQ ID NO: 14 (full light chain 2,nt) | SEQ ID NO: 13 (full light chain 2,aa) | |
| H1L3 | heavy chain | SEQ ID NO: 24 (VH1,nt) | SEQ ID NO: 23 (VH1, aa) | SEQ ID NO: 26 (full heavy chain 1,nt) | SEQ ID NO: 25 (full heavy chain 1,aa) | 115 |
| | light chain | SEQ ID NO: 16 (VL3,nt) | SEQ ID NO: 15 (VL3,aa) | SEQ ID NO: 18 (full light chain 3,nt) | SEQ ID NO: 17 (full light chain 3,aa) | |
| H2L3 | heavy chain | SEQ ID NO: 28 (VH2,nt) | SEQ ID NO: 27 (VH2,aa) | SEQ ID NO: 30 (full heavy chain 2,nt) | SEQ ID NO: 29 (full heavy chain 2,aa) | 123 |
| | light chain | SEQ ID NO: 16 (VL3,nt) | SEQ ID NO: 15 (VL3,aa) | SEQ ID NO: 18 (full light chain 3,nt) | SEQ ID NO: 17 (full light chain 3,aa) | |
| H3L3 | heavy chain | SEQ ID NO: 32 (VH3,nt) | SEQ ID NO: 31 (VH3,aa) | SEQ ID NO: 34 (full heavy chain 3,nt) | SEQ ID NO: 33 (full heavy chain 3,aa) | 97.6 |
| | light chain | SEQ ID NO: 16 | SEQ ID NO: 15 | SEQ ID NO: 18 | SEQ ID NO: 17 | |

TABLE 1-continued

Expression levels of different combinations of humanized light and heavy chains in 293S cells

| No. | | Gene sequence of variable region of humanized antibody | Amino acid sequence of variable region of humanized antibody | Full length gene sequence of humanized antibody | Full length amino acid sequence of humanized antibody | antibody concentration in culture supernatant (µg/ml) |
|---|---|---|---|---|---|---|
| H1L4 | heavy chain | SEQ ID NO: 24 (VH1,nt) | SEQ ID NO: 23 (VH1, aa) | SEQ ID NO: 26 (full heavy chain 1,nt) | SEQ ID NO: 25 (full heavy chain 1,aa) | 183 |
|  | light chain | SEQ ID NO: 20 (VL4,nt) | SEQ ID NO: 19 (VL4,aa) | SEQ ID NO: 22 (full light chain 4,nt) | SEQ ID NO: 21 (full light chain 4,aa) |  |
| H2L4 | heavy chain | SEQ ID NO: 28 (VH2,nt) | SEQ ID NO: 27 (VH2,aa) | SEQ ID NO: 30 (full heavy chain 2,nt) | SEQ ID NO: 29 (full heavy chain 2,aa) | 155 |
|  | light chain | SEQ ID NO: 20 (VL4,nt) | SEQ ID NO: 19 (VL4,aa) | SEQ ID NO: 22 (full light chain 4,nt) | SEQ ID NO: 21 (full light chain 4,aa) |  |
| H3L4 | heavy chain | SEQ ID NO: 32 (VH3,nt) | SEQ ID NO: 31 (VH3,aa) | SEQ ID NO: 34 (full heavy chain 3,nt) | SEQ ID NO: 33 (full heavy chain 3,aa) | 172 |
|  | light chain | SEQ ID NO: 20 (VL4,nt) | SEQ ID NO: 19 (VL4,aa) | SEQ ID NO: 22 (full light chain 4,nt) | SEQ ID NO: 21 (full light chain 4,aa) |  |
| 38E Chimeric | heavy chain | SEQ ID NO: 49 (38E Chimeric VH,nt) | SEQ ID NO: 48 (38E Chimeric VH, aa) | SEQ ID NO: 53 (38E Chimericfull heavy chain, nt) | SEQ ID NO: 52 (38E Chimeric full heavy chain,aa) | 97.4 |
|  | light chain | SEQ ID NO: 47 (38E Chimeric VL,nt) | SEQ ID NO: 46 (38E Chimeric VL, aa) | SEQ ID NO: 51 (38E Chimericfull light chain, nt) | SEQ ID NO: 50 (38E Chimeric full light chain,aa) |  |

TABLE 2

ELISA results of different combinations of humanized light and heavy chains via 293S cell expression supernatant (non-heated)

| Clone No./ non-heated | Antibody concentration (µg/mL) | | | |
|---|---|---|---|---|
|  | 1 | 0.2 | 0.04 | 0 |
| H1L1 | 11840 | 10574 | 6849 | 2134 |
| H2L1 | 11953 | 10737 | 6369 |  |
| H3L1 | 11367 | 10041 | 6222 |  |
| H1L2 | 12118 | 11246 | 6682 |  |
| H2L2 | 11699 | 10321 | 6517 |  |
| H3L2 | 11266 | 10575 | 6599 |  |
| H1L3 | 11846 | 10790 | 6435 |  |
| H2L3 | 11967 | 11286 | 6266 |  |
| H3L3 | 11280 | 10978 | 6755 |  |
| H1L4 | 11929 | 10931 | 7321 |  |
| H2L4 | 11821 | 10859 | 6877 |  |
| H3L4 | 11918 | 11226 | 7055 |  |
| 38E Chimeric | 11353 | 10414 | 6783 |  |

TABLE 3

ELISA results of different combinations of humanized light and heavy chains via 293S cell expression supernatant (heated)

| Clone No/heated | Antibody concentration (µg/mL) | | | |
|---|---|---|---|---|
|  | 1 | 0.2 | 0.04 | 0 |
| H1L1 | 9796 | 9007 | 5970 | 27.7 |
| H2L1 | 9647 | 8560 | 5442 |  |
| H3L1 | 9131 | 7903 | 5192 |  |
| H1L2 | 9833 | 8925 | 5493 |  |
| H2L2 | 9779 | 8716 | 5259 |  |
| H3L2 | 9448 | 8775 | 5065 |  |
| H1L3 | 9627 | 8748 | 4978 |  |
| H2L3 | 9731 | 9153 | 4866 |  |
| H3L3 | 9543 | 8898 | 5393 |  |
| H1L4 | 10526 | 9705 | 5670 |  |
| H2L4 | 10572 | 9234 | 5702 |  |
| H3L4 | 9948 | 9061 | 5299 |  |
| 38E Chimeric | 10567 | 8845 | 4727 |  |

Figure 17A:
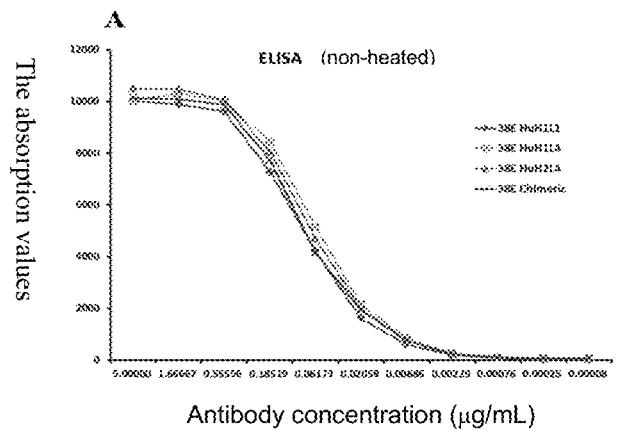
Figure 17B:
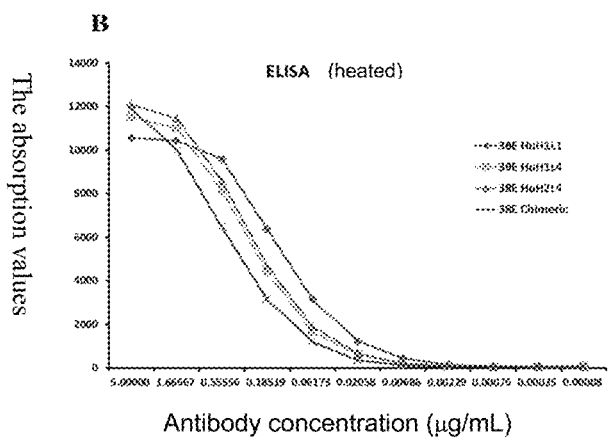
Figure 17C:
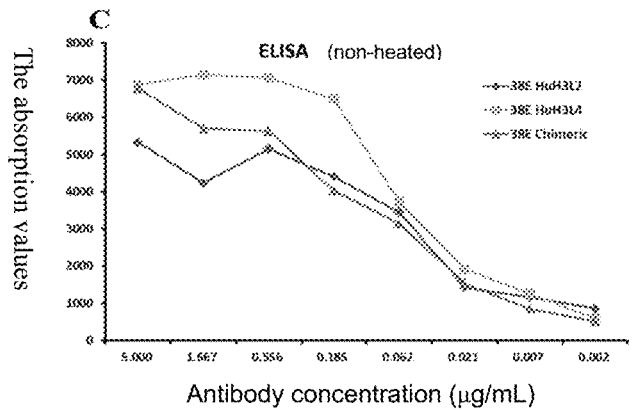
Figure 17D:
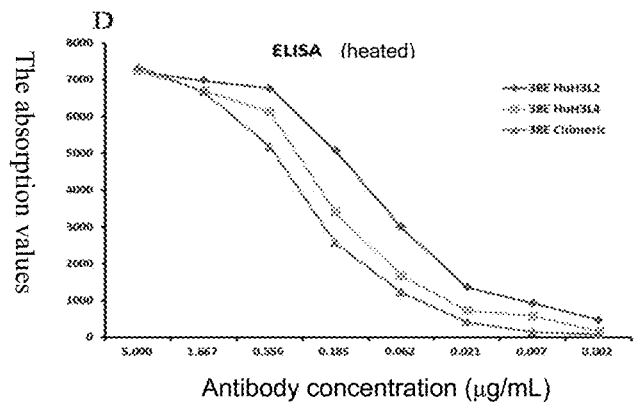

Example 15 Characterization of the Selected Humanized Candidate Antibodies with Purified IgG Samples Based on the binding affinity, percentage of humanization, antibody expression level and thermal stability data, the following five candidate antibodies were selected for the next characterization step: H1L1, H1L4, H2L4, H3L2, H3L4, and the five candidate antibodies were renumbered as 38E HuH1L1 (SEQ ID NOs: 25 and 9), 38E HuH1L4 (SEQ ID NOs: 25 and 21), 38E HuH2L4 (SEQ ID NOs: 29 and 21), 38E HuH3L2 (SEQ ID NOs: 33 and 13), and 38E HuH3L4 (SEQ ID NOs: 33 and 21). Then the selected VH/VL plasmids were co-transfected with 293S cells, the cell culture supernatant was harvested, and the antibody was purified by protein A affinity chromatography. The purified antibody was used for binding ELISA analysis to compare the specific binding ability of the humanized antibodies to the 38E chimeric antibody. The invention also underwent some preliminary analyses to compare their thermal stability and non-specific binding. The results showed that the candidate antibodies being purified and the 38E chimeric antibody had very similar antigen-binding properties (FIG. 17A, 17C). After treatment at 70° C. for 5 min, all five humanized antibodies showed similar binding ability with the chimeric antibodies (FIG. 17B, 17D).

Example 16 Evaluation of Non-Specific Binding of Humanized Candidate Antibodies LIF-negative HEK293 cells FACS was used for preliminary assay to assess the risk of potential non-specific binding of the antibody.

HEK293 cells were digested with trypsin, washed twice with PBS containing 1% FBS, resuspended, adjusted to a cell density of $1.5-2\times10^6$ cells/mL, and added to a 96-well U-shaped plate. The concentration of antibody to be detected was adjusted to 20 μg/mL, and then 3-times gradient dilution was performed for a total of 8 concentrations, and a blank control and a negative control (Rituxan) were set up. The diluted antibody and blank control were added to the cells in 96-well plates, and 100 μL of antibody was added to each well. The cells were incubated at 4° C. for 1 hour, centrifuged at 1000 rpm for 5 minutes, the supernatant was carefully discarded and washed twice with PBS containing 1% FBS, and finally resuspended with 200 μL of PBS containing 1% FBS, finally, resuspend the cells with 200 μL of PBS containing 1% FBS, and flow cytometric analysis was performed. In the non-specific binding FACS assay of HEK293 cell, 38E HuH1L1, 38E HuH3L2, 38E HuH3L4, 38E HuH1L4, 38E chimeric antibody and negative control (Rituxan) had similar non-specific binding affinity for HEK293 cells, while 38E HuH2L4 had a higher non-specific binding affinity for HEK293 cells (Subfigure A and B in FIG. 18).

Example 17 CE-SDS Analysis of Antibody Purity

The working concentration of CE-SDS analysis was 1 mg/mL, the antibody samples were diluted to the specified concentration with the loading buffer.

Preparation of non-reduced CE-SDS electrophoresis samples: 95 μL of diluted sample solution was taken, 5 μL of 0.8M ammonium iodoacetate aqueous solution and 5 μL of internal reference were added, vortexed and mixed well. 95 μL of blank control was taken, 5 μL of 0.8M ammonium iodoacetate aqueous solution and 5 μL of internal reference were added, vortexed and mixed well for non-reduced blank control. Then heated in metal bath at 70° C. for 5 minutes, cooled to room temperature, and centrifuged at 6000 rpm for 1 minute.

Preparation of the reduced sample solution: 95 μL of diluted sample solution was taken, 5 μL of 2-mercaptoethanol solution and 5 μL of internal reference were added, vortexed and mixed well. 95 μL of blank control was taken, and 5 μL of 2-mercaptoethanol solution and 5 μL of internal reference were added, vortexed and mixed well for reduced blank control. Then heated in metal bath at 70° C. for 15 minutes, cooled to room temperature, and centrifuged at 6000 rpm for 1 minute.

Sample analysis: 75 μL of sample was added to the test tube, and the test tube was placed into the test cup. The test cup was carefully inserted into the injection tray, and the test program was run with a reduced sample injection duration of 30 seconds and a non-reduced sample injection duration of 40 seconds, capillary temperature of 20° C., sample temperature of 20° C., focusing voltage of 15 KV, focusing time of 40 minutes, and data were collected with a PDA detector at 214 nm. CE results are shown in Table 4, Table 5.

TABLE 4

Results of the reduced CE-SDS

|  | Peak# | Size (KDa) | Peak Area (%) | Peak ID |
|---|---|---|---|---|
| 38E chimeric | 1 | 27.77 | 35.5 | LC |
|  | 2 | 62.43 | 64.5 | HC |
| 38E HuH1L1 | 1 | 25.6 | 0.57 | LMC |
|  | 2 | 27.85 | 32.02 | LC |
|  | 3 | 36.03 | 1.41 | LMC |
|  | 4 | 61.41 | 66 | HC |
| 38E HuH3L2 | 1 | 27.41 | 31.7 | LC |
|  | 2 | 33.84 | 0.35 | LMC |
|  | 3 | 62.49 | 67.95 | HC |
| 38E HuH3L4 | 1 | 27 | 34.93 | LC |
|  | 2 | 62.06 | 65.07 | HC |

TABLE 5

Results of the non-reduced CE-SDS

|  | Size (KDa) | Peak Area (%) | Peak ID |
|---|---|---|---|
| 38E chimeric | 166.39 | >99 | intact AB |
| 38E HuH1L1 | 165.93 | 92.46 | intact AB |
| 38E HuH3L2 | 167.63 | 93.01 | intact AB |
| 38E HuH3L4 | 166.37 | 98.82 | intact AB |

Example 18 Thermal Stability Analysis by Differential Scanning Fluorescence (DSF)/Static Light Scattering (SLS) Technique Samples were submitted to UNcle Systems (Unchained Labs) for analysis. The temperature range of 25° C. to 95° C. was monitored for DSF and SLS at 1° C./min. UNcle measured SLS at 266 nm and 473 nm. Tm and Tagg were calculated and analyzed using UNcle analysis software.

IgG is with multiple structural domains, each has its own melting temperature (Tm.) The CH2 structural domain typically has a Tm of about 70° C. in PBS, and CH3 is more stable with a Tm of about 80° C. Fabs have a larger range of Tm of about 50-85° C. due to their more variable sequences. Therefore, the Tm values measured by various analytical techniques are usually the "apparent" transition temperatures, rather than the true Tm values of each structural domain. It is clear that even this DSF analysis can produce more than one Tm value, only Tm1 is used to evaluate the thermal stability of therapeutic antibodies. Tagg is the temperature at which SLS starts to detect aggregation. Tagg266 measures SLS at 266 nm, which is more sensitive and more suitable for detecting smaller aggregated particles. Tagg473 measures SLS at 473 nm, which is more suitable for detecting larger particles.

As shown in Table 6, all three humanized candidate antibodies have higher melting temperature (Tm1) and less aggregation risk than the 38E chimeric antibody.

TABLE 6

Results of Differential Scanning Fluorescence (DSF)/Static Light Scattering (SLS) analysis

| Sample | DSF (° C.) | | | SLS (° C.) | |
|---|---|---|---|---|---|
| | Tm1 | Tm2 | Tm3 | Tagg 266 | Tagg 473 |
| 38E chimeric | 69.3 | | | 68.5 | 69.8 |
| 38E HuH1L1 | 72.7 | 82.8 | | 72.5 | 73.6 |
| 38E HuH3L2 | 72 | 82.4 | | 73.3 | 73.7 |
| 38E HuH3L4 | 71.5 | 82.1 | | 69.8 | 70.9 |

Example 19 Analysis of Aggregation Tendency of Antibodies Using Dynamic Light Scattering Technique (DLS)

DLS was performed on the UNcle system (Unchained Labs). DLS was measured at 25° C. Data were calculated and analyzed using UNcle analysis software. Dynamic Light Scattering (DLS) is used to detect the aggregation in antibody samples. The "mode diameter" refers to the diameter of the protein particle, and the "mass percentage" refers to the percentage of each particle size fraction. The "PDI" refers to the polydispersity index, the higher the index, the more polydispersed the sample is. If the PDI is not greater than 0.25, the sample can be considered as mono-disperse. As shown in Table 7, all four antibody samples had a main "peak" (mass fraction over 99%), with 38E HuH3L4 having a better PDI than the chimeric antibody, 38E HuH3L2 being similar to the chimeric antibody, and 38E HuH1L1 having a worse PDI than the chimeric antibody.

TABLE 7

Results of Dynamic light scattering technique (DLS) analysis

| | Peak1 | | | Peak2 | |
|---|---|---|---|---|---|
| Sample | mode diameter (nm) | mass percentage (%) | PDI | mode diameter (nm) | mass percentage (%) |
| 38E chimeric | 10.41 | 99.90 | 0.229 | | |
| 38E HuH1L1 | 9.68 | 99.15 | 0.383 | 101.16 | 0.96 |
| 38E HuH3L2 | 10.41 | 99.62 | 0.28 | 99.18 | 0.38 |
| 38E HuH3L4 | 10.41 | 100.00 | 0.043 | | |

Example 20 Antibody Affinity Assay

The affinity of anti-LIF antibody to human LIF protein was determined using Gator. The anti-human LIF antibody was first diluted to 5 μg/mL with PBS and then added to A-F wells in second column of the 96-well plate (200 μL per well). The human LIF protein concentrations were gradient diluted with PBS to 100, 50, 25, 12.5 and 6.25 μg/mL, respectively, and the diluted LIF protein was added to wells A-E wells in the fourth column of the 96-well plate (100 μL per well) and PBS was added to F well as blank control. PBS was added to A-F wells in the first and third columns (200 μL per well). The 96-well plates were placed into the instrument and detected with anti-human Fc biosensor. The results were shown in Table 8, which showed that the affinity of the three humanized antibodies was close to that of the chimeric antibodies.

TABLE 8

Humanized anti-LIF antibody affinity assay

| Sample | Koff (1/s) | Kon (1/Ms) | KD (M) |
|---|---|---|---|
| 38E HuH1L1 | 4.65E−05 | 5.69E+05 | 8.17E−11 |
| 38E HuH3L2 | 3.39E−05 | 6.31E+05 | 5.38E−11 |
| 38E HuH3L4 | 4.44E−05 | 5.79E+05 | 7.66E−11 |
| 38E chimeric | 1.57E−05 | 6.77E+05 | 2.33E−11 |

Example 21 Expression Purification of Humanized Antibodies and 38E10E1C11 Antibodies The variable regions of the light and heavy chains of the humanized antibodies 38E HuH3L2 and 38E HuH3L4 were linked with the constant regions of the mouse antibodies (the constant region of the heavy chain was mouse IgG1, the constant region of the light chain was kappa chain) and cloned into the PCDNA.3.4 vector, respectively, named 38E HuH3L2-m (the full-length gene sequences encoding the heavy and light chains of the 38E HuH3L2-m antibodies are shown in SEQ ID NO:36 and SEQ ID NO:38, respectively; and the corresponding full-length amino acid sequences of the heavy and light chains of the 38E HuH3L2-m antibody are shown in SEQ ID NO:35 and SEQ ID NO:37, respectively) and 38E HuH3L4-m (the full-length gene sequences of the heavy and light chains are shown in SEQ ID NO:36 and SEQ ID NO:40, respectively, and the corresponding full-length amino acid sequences of the heavy and light chains of the 38E HuH3L4-m antibodies are shown in SEQ ID NO:35 and SEQ ID NO:39, respectively). Gene transfection and antibody expression were performed using the Expi CHO Expression Kit from thermo fisher. Cell culture supernatant was collected and the antibody was purified using a protein G affinity chromatography column. The purified antibody was concentrated and exchanged by ultrafiltration using Amicon® Ultra ultrafiltration tubes, and the antibody was finally dissolved in PBS of pH 7.4. The 38E10E1C11 antibody was also expressed and purified in the same manner.

Example 22 Humanized Anti-LIF Antibody Competes with LIFR for Binding to Human LIF Protein The recombinant human LIF protein is coated at a concentration of 1 μg/mL in enzyme labeled plates, and 50 μL/well of recombinant human LIFR protein at a concentration of 0.6125 μg/mL (fusion expressed with human Fc, purchased from ACRO, item number: LIR-H4252) is added, meanwhile 100 μL/well of different LIF antibodies 38E HuH3L2-m (SEQ ID NOs: 35 and 37), 38E HuH3L4-m (SEQ ID NOs: 35 and 39), 38E10E1C11 (SEQ ID NOs: 41 and 43), P36-033 (SEQ ID NOs: 54 and 56) at different concentrations were added. Anti-CD3 antibody was used as negative control (purchased from BioLegend, No. 317326).

The plates were incubated for 2 h at room temperature and washed four times with PBST, HRP-labeled goat anti-human Fc antibodies were added, and the plates were incubated for 1 h at room temperature and washed four times with PBST. TMB colored solution was added and color developing for 10 min at room temperature. The absorption value at 450 nm was read by an enzyme marker. The data were analyzed and plotted using Origin pro 9 software. The results were detailed in FIG. 19. The results showed that 38E10E1C11, 38E HuH3L2-m, 38E HuH3L4-m were able to inhibit the binding of recombinant human LIF to human LIFR with IC50 of 0.074 µg/ml, 0.145 µg/ml and 0.103 µg/ml, respectively. P36-033 had a weak inhibitory effect and the negative control anti-CD3 antibody could not inhibit the binding of recombinant human LIF to human LIFR.

Example 23 Humanized Anti-LIF Antibody does not Compete with GP130 to Bind Human LIF Protein The recombinant human LIF protein was coated at a concentration of 1 µg/mL in the enzyme labeled plate, and 50 µL/well of recombinant human GP130 protein at a concentration of 12 µg/mL (fusion expressed with human Fc, purchased from Yijiao Shenzhou, item number: 10974-H03H) was added, meanwhile 100 µL/well of LIF antibodies 38E HuH3L2-m ((SEQ ID NOs: 35 and 37), 38E HuH3L4-m (SEQ ID NOs: 35 and 39) and P36-033 (SEQ ID NOs: 56 and 54) at different concentrations were added, anti-CD28 antibody was as a negative control (purchased from BioLegend, item no. 302914). The plates were incubated for 2 h at room temperature and washed with PBST four times. HRP-labeled goat anti-human Fc antibodies were added and incubated for 1 h at room temperature, and washed four times with PBST. TMB colored solution was added and color developing for 10 min at room temperature. The absorption value at 450 nm was read by an enzyme marker. The data were analyzed and plotted using Origin pro 9 software. The results were detailed in FIG. 20. The results showed that the humanized antibodies 38E HuH3L2-m, 38E HuH3L4-m and the negative control antibody of anti-CD28 antibody did not inhibit the binding of recombinant human LIF to human GP130 protein, and P36-033 could inhibit the binding of recombinant human LIF to human GP130 protein.

Example 24 Antigen Recognition Specificity Assay of Humanized Anti-LIF Antibody Human LIF, human IL-6, human OSM and human CNTF (all four proteins were purchased from Yijiao Shenzhou, item numbers 14890-HNAH; 10395-HNAE; 10452-HNAH; 11841-H07E, respectively) were coated at a concentration of 1 µg/mL in enzyme labeled plates, and different concentrations of LIF antibodies 38E10E1C11, 38E huH3L2-m, 38E huH3L4-m were incubated at room temperature for 1 h. After washed four times with PBST, HRP-labeled goat anti-mouse Fab secondary antibodies were added and incubated at room temperature for 1 h. After washed four times with PBST, TMB colored solution was added and color developing for 10 min at room temperature. The absorption value at 450 nm was read by the enzyme maker. The data were analyzed and plotted using Origin pro 9 software. The results were shown in FIG. 21, the result shows that 38E10E1C11, 38E huH3L2-m and 38E huH3L4-m antibodies only bind to human LIF protein but not to human IL-6, OSM and CNTF.

Example 25 Identification of Epitopes Recognized by Humanized Anti-LIF Antibody In the previous experiments, the invention found that the 38E10E1C11 antibody recognizes a linear epitope of LIF protein, so whether the 38E humanized antibody still recognizes the linear epitope of LIF protein firstly needed to be verified. The supernatant of 293T cells transfected with human LIF full-length gene sequence, Mut3 and Mut4 protein sequences after 3 days of culture, and the negative control of 293T cell culture supernatant were taken, 5×SDS-PAGE loading buffer was added, and boiled for 10 minutes. Then 10 µL of sample was taken for SDS-PAGE electrophoresis, and then the electrophoretic bands were transferred to PVDF membrane for western blot detection. The primary antibody for detection was 38E huH3L2 or 38E huH3L4 antibody at a concentration of 1 µg/mL, and was incubated for 2 hours at room temperature. Then washed three times in PBST buffer and diluted HRP-labeled sheep anti-human Fc secondary antibody at a dilution ration of 1:3000 was added, incubated with the secondary antibody for 2 hours at room temperature, washed three times in PBST buffer and enhanced Chemiluminescent solution (Perice, item no. 34079) was added and incubated. An Amersham Imager 600 ultra-sensitive multifunctional imager was used for detection and photograph. The results were shown in subfigure A in FIG. 22, the result shows that both humanized antibodies could recognize the denatured human LIF protein and Mut3 protein but not Mut4 protein. The same results were obtained in the M1 cell proliferation assay, and the results were detailed in subfigure B in FIG. 22. Therefore, the epitope sequences recognized by the 38E huH3L2 and 38E huH3L4 antibodies were determined to be TYGPDTSGKDVFQKK (SEQ ID NO: 61).

Example 26 STAT3 Activation Inhibition Assay of KP4 Cells to Detect Humanized Anti-LIF Antibody Activity After digestion and centrifugation of KP4 cells, cells were re-suspended and plated in 12-well plates at 1 mL, $5 \times 10^5$ cells/well. The plates were incubated at 37° C., 5% $CO_2$ overnight. The next day, the original medium was discarded, cell medium containing 50 ng/mL recombinant human LIF protein and different concentrations of anti-LIF humanized antibodies was added respectively. Control wells without recombinant human LIF protein and with only recombinant human LIF protein and without antibodies were set up, and the plates were incubated for 30 min at 37° C. incubator. Then the medium was removed, 100 µL of 1× cell lysis solution was added to each well, and the mixture was lysed for 30 min on ice. The lysate was transferred to a 1.5 mL centrifuge tube and centrifuged at 13,000 rpm for 10 min, and the supernatant was collected. The supernatant was taken for western blot detection to detect the phosphorylation of STAT3. The results showed that the humanized antibodies 38E huH3L4 and 38E huH3L2 were able to inhibit LIF protein-induced phosphorylation of STAT3 (FIG. 23).

Example 27 M1 Cell Proliferation Assay to Detect the Activity of Humanized Anti-LIF Antibody After centrifugation of M1, washed with RPMI1640 medium twice, and 96-well plates were inoculated at a density of $2.5 \times 10^5$ cells/mL. 80 µL of the cells were inoculated in each well, and medium containing 4 ng/ml of recombinant human LIF protein and different concentrations of anti-LIF antibodies were added to make the final volume of each well to 160 μL. While control wells without LIF were set up and incubated at 37° C. for 72 hours and proliferation was detected by adding CCK-8. The results were detailed in FIG. 24, the result shows that both humanized antibodies 38E huH3L4-m and 38E huH3L2-m were able to reverse the proliferation inhibition of M1 cells by human LIF protein with EC50 of 6.52 μg/mL and 8.93 μg/mL, respectively.

Example 28 Inhibition Effect of LIF-Induced STAT3 Phosphorylation by LIF Antibody 100,000 KP4 cells were inoculated in 96-well plates; and gradient diluted LIF antibody was incubated with 20-100 ng/ml of LIF protein at room temperature for 0.5-1 h to form LIF-Ab mixture. LIF-Ab mixture was added to cell wells and stimulated for 5-30 min at 37° C. Detecting P-STAT3 and Total-STAT3 protein expression levels according to P-STAT3(TYR705) KITS(Cisbio) and Total-STAT3 KITS (Cisbio) instructions. The emission signal ratio of the donor and acceptor for each well was calculated: Ratio=Signal 665 nm/Signal 620 nm*$10^4$. Prism software was used to generate data graphs and count the inhibition rate of LIF antibody. The results showed that the LIF antibody 38E HuH3L4 has inhibition effect of phosphorylation of STAT3 phosphorylation induced by LIF, as shown in FIG. 25, with an $IC_{50}$ of 3.415 nM.

Example 29 Detection of ADCC Activity of LIF Antibody

LIF binds to GP130 and LIFR, while humanized LIF antibody blocks LIF binding to LIFR, but not LIF binding to GP130. Detecting whether humanized LIF antibody binds to the cell surface mediated by LIF and thus ADCC works. Antibodies Erbitux (Epiduo®, Merck Serono, positive control) and Human IgG2 (Cat #HG2K, Sino, negative control) were sequentially diluted with ADCC buffer (RPMI-1640+ 1% FBS); and the 38E huH3L4 antibody was then diluted in triplicate and eight gradients with ADCC buffer containing LIF protein, and set aside. DLD-1 cells were digested with trypsin (Cat #25200072, GIBCO), and after the reaction was terminated, the cells were blown apart and collected into a centrifuge tube, centrifuged at 1500 rpm for 3 min. The supernatant was discarded, and the cells were re-suspended with ADCC buffer and counted. The cell concentration was adjusted and set aside. PBMC cells (Cat #SLB-HP010B, Shanghai SAILYBIO Ltd.) were resuscitated, and 10 mL of ADCC buffer was added, centrifuged at 2000 rpm for 10 min, and the supernatant was discarded. The PBMC cells were re-suspend in ADCC buffer and counted. The cell concentration was adjusted and set aside; and take out the 96-well U-bottom cell culture plate, 50 μl of target cells DLD-1, 50 μl of antibody, and 50 μl of PBMC effector cells were added in turn. The ratio of PBMC effector cells and target cells was 30:1. The reaction was carried out in a 5% $CO_2$ incubator at 37° C. for 6 h. LDH was detected by Cyto Tox96 Non-Radioactive Cytotoxicity Assay Kit (Cat #G1780, Promega) and the absorbance values were measured at 490 nm using an enzyme marker.

The mean absorbance values of each parallel well were calculated so that the average absorbance values of all experimental wells, target cell LDH spontaneous release wells (TCR), and effector cell LDH spontaneous release wells (ECR) were subtracted from the average absorbance values of blank medium (CMB). The average absorbance value of the target cell LDH maximum release wells (TCM) was subtracted from the average absorbance value of the volume corrected control wells (VCC). Cytotoxicity (%) from each concentration of antibody was calculated using the above corrected values according to the following formula.

Cytotoxicity (%)=(A−B−C)/(D−C)×100%

A: average absorbance value after correction of experimental wells
B: average absorbance value of the corrected effector cell LDH spontaneous release wells
C: average absorbance value of the corrected target cell LDH spontaneous release wells
D: average absorbance value of the corrected LDH maximal release pore of the target cell As shown in FIG. 26, 38E huH3L4 antibody had no ADCC activity.

REFERENCES

1. Nicola N A, Babon J J. Leukemia inhibitory factor (LIF). Cytokine Growth Factor Rev. 2015: 26(5):533-44.
2. Pastuschek J, Poetzsch J, Morales-Prieto D M, Schleußner E, Markert U R, Georgiev G. Stimulation of the JAK/STAT pathway by LIF and OSM in the human granulosa cell line COV434. J Reprod Immunol. 2015; 108:48-55.
3. Liu S C, Tsang N M, Chiang W C, Chang K P, Hsueh C, Liang Y, Juang J L, Chow K P, Chang Y S. Leukemia inhibitory factor promotes nasopharyngeal carcinoma progression and radioresistance. J Clin Invest. 2013: 123(12):5269-83.
4. Shi Y, Gao W, Lytle N K, Huang P, Yuan X, Dann A M, et al. Targeting LIF-mediated paracrine interaction for pancreatic cancer therapy and monitoring. Nature. 2019; 569(7754): 131-135.
5. Cartwright P, McLean C, Sheppard A, RivettD, Jones K, Dalton S. LIF/STAT3 controls ES cell self-renewal and pluripotency by a Myc-dependent mechanism. Development 2005; 132:885-96.
6. Kuphal S, Wallner S, Bosserhoff A K. Impact of LIF (leukemia inhibitory factor) expression in malignant melanoma. Exp Mol Pathol 2013: 95:156-65.
7. Liu B, Lu Y, Li J, Liu Y, Liu J, WangW. Leukemia inhibitory factor promotes tumor growth and metastasis inhuman osteosarcoma via activating STAT3. APMIS 2015:123:837-46.
8. Morton S D, Cadamuro M, Brivio S, Vismara M, Stecca T, Massani M, et al. Leukemia inhibitory factor protects cholangiocarcinoma cells from drug induced apoptosis via a PI3K/AKT-dependent Mcl-1 activation. Oncotarget. 2015:6:26052-64.
9. Kamohara H, Ogawa M, Ishiko T, Sakamoto K, Baba H. Leukemia inhibitory factor functions as a growth factor in pancreas carcinoma cells: involvement of regulation of LIF and its receptor expression. Int J Oncol. 2007:30: 977-83.
10. Shin J E, Park S H, Jang Y K. Epigenetic up-regulation of leukemia inhibitory factor (LIF) gene during the progression to breast cancer. Mol Cells 2011: 31:181-9.
11. Li X, Yang Q, Yu H, Wu L, Zhao Y, Zhang C, Yue X, Liu Z, Wu H, Haffty B G, Feng Z, Hu W. LIF promotes tumorigenesis and metastasis of breast cancer through the AKT-mTOR pathway. Oncotarget. 2014: 5(3):788-801.

12. Liu S C, Hsu T, Chang Y S, Chung A K, Jiang S S, OuYang C N, Yuh C H, Hsueh C, Liu Y P, Tsang N M. Cytoplasmic LIF reprograms invasive mode to enhance NPC dissemination through modulating YAPI-FAK/PXN signaling. Nat Commun. 2018: 9(1):5105.

13. Viswanadhapalli S. Luo Y. Sareddy G R. Santhamma B. Zhou M. et al. EC359: A First-in-Class Small-Molecule Inhibitor for Targeting Oncogenic LIFR Signaling in Triple-Negative Breast Cancer. Mol Cancer Ther. 2019: 18(8): 1341-1354.

What is claimed is:

1. An isolated anti-LIF (Leukemia Inhibitory Factor) monoclonal antibody or antigen-binding fragment thereof, comprising:
   (a) LCDR1 comprising the amino acid sequence of SEQ ID NO: 1;
   (b) LCDR2 comprising the amino acid sequence of SEQ ID NO: 2;
   (c) LCDR3 comprising the amino acid sequence of SEQ ID NO: 3;
   (d) HCDR1 comprising the amino acid sequence of SEQ ID NO: 4;
   (e) HCDR2 comprising the amino acid sequence of SEQ ID NO: 5; and
   (f) HCDR3 comprising the amino acid sequence of SEQ ID NO: 6.

2. The monoclonal antibody or antigen-binding fragment thereof of claim 1, comprising:
   1) A light chain variable region (VL) that comprises an amino acid sequence with at least 85% identity to the amino acid sequence of SEQ ID NO: 7, and a heavy chain variable region (VH) that comprises an amino acid sequence with at least 85% identity to the amino acid sequence of SEQ ID NO: 23;
   2) A light chain variable region (VL) that comprises an amino acid sequence with at least 85% identity to the amino acid sequence of SEQ ID NO: 7, and a heavy chain variable region (VH) that comprises an amino acid sequence with at least 85% identity to the amino acid sequence of SEQ ID NO: 27;
   3) A light chain variable region (VL) that comprises an amino acid sequence with at least 85% identity to the amino acid sequence of SEQ ID NO: 7, and a heavy chain variable region (VH) that comprises an amino acid sequence with at least 85% identity to the amino acid sequence of SEQ ID NO: 31;
   4) A light chain variable region (VL) that comprises an amino acid sequence with at least 85% identity to the amino acid sequence of SEQ ID NO: 11, and a heavy chain variable region (VH) that comprises an amino acid sequence with at least 85% identity to the amino acid sequence of SEQ ID NO: 23;
   5) A light chain variable region (VL) that comprises an amino acid sequence with at least 85% identity to the amino acid sequence of SEQ ID NO: 11, and a heavy chain variable region (VH) that comprises an amino acid sequence with at least 85% identity to the amino acid sequence of SEQ ID NO: 27;
   6) A light chain variable region (VL) that comprises an amino acid sequence with at least 85% identity to the amino acid sequence of SEQ ID NO: 11, and a heavy chain variable region (VH) that comprises an amino acid sequence with at least 85% identity to the amino acid sequence of SEQ ID NO: 31;
   7) A light chain variable region (VL) that comprises an amino acid sequence with at least 85% identity to the amino acid sequence of SEQ ID NO: 15, and a heavy chain variable region (VH) that comprises an amino acid sequence with at least 85% identity to the amino acid sequence of SEQ ID NO: 23;
   8) A light chain variable region (VL) that comprises an amino acid sequence with at least 85% identity to the amino acid sequence of SEQ ID NO: 15, and a heavy chain variable region (VH) that comprises an amino acid sequence with at least 85% identity to the amino acid sequence of SEQ ID NO: 27;
   9) A light chain variable region (VL) that comprises an amino acid sequence with at least 85% identity to the amino acid sequence of SEQ ID NO: 15, and a heavy chain variable region (VH) that comprises an amino acid sequence with at least 85% identity to the amino acid sequence of SEQ ID NO: 31;
   10) A light chain variable region (VL) that comprises an amino acid sequence with at least 85% identity to the amino acid sequence of SEQ ID NO: 19, and a heavy chain variable region (VH) that comprises an amino acid sequence with at least 85% identity to the amino acid sequence of SEQ ID NO: 23;
   11) A light chain variable region (VL) that comprises an amino acid sequence with at least 85% identity to the amino acid sequence of SEQ ID NO: 19, and a heavy chain variable region (VH) that comprises an amino acid sequence with at least 85% identity to the amino acid sequence of SEQ ID NO: 27; or
   12) A light chain variable region (VL) that comprises an amino acid sequence with at least 85% identity to the amino acid sequence of SEQ ID NO: 19, and a heavy chain variable region (VH) that comprises an amino acid sequence with at least 85% identity to the amino acid sequence of SEQ ID NO: 31.

3. The monoclonal antibody or antigen-binding fragment thereof of claim 1, comprising:
   1) A light chain variable region (VL) that comprises the amino acid sequence of SEQ ID NO: 7, and a heavy chain variable region (VH) that comprises the amino acid sequence of SEQ ID NO: 23;
   2) A light chain variable region (VL) that comprises the amino acid sequence of SEQ ID NO: 7, and a heavy chain variable region (VH) that comprises the amino acid sequence of SEQ ID NO: 27;
   3) A light chain variable region (VL) that comprises the amino acid sequence of SEQ ID NO: 7, and a heavy chain variable region (VH) that comprises the amino acid sequence of SEQ ID NO: 31;
   4) A light chain variable region (VL) that comprises the amino acid sequence of SEQ ID NO: 11, and a heavy chain variable region (VH) that comprises the amino acid sequence of SEQ ID NO: 23;
   5) A light chain variable region (VL) that comprises the amino acid sequence of SEQ ID NO: 11, and a heavy chain variable region (VH) that comprises the amino acid sequence of SEQ ID NO: 27;
   6) A light chain variable region (VL) that comprises the amino acid sequence of SEQ ID NO: 11, and a heavy chain variable region (VH) that comprises the amino acid sequence of SEQ ID NO: 31;
   7) A light chain variable region (VL) that comprises the amino acid sequence of SEQ ID NO: 15, and a heavy chain variable region (VH) that comprises the amino acid sequence of SEQ ID NO: 23;
   8) A light chain variable region (VL) that comprises the amino acid sequence of SEQ ID NO: 15, and a heavy chain variable region (VH) that comprises the amino acid sequence of SEQ ID NO: 27;
   9) A light chain variable region (VL) that comprises the amino acid sequence of SEQ ID NO: 15, and a heavy chain variable region (VH) that comprises the amino acid sequence of SEQ ID NO: 31;
   10) A light chain variable region (VL) that comprises the amino acid sequence of SEQ ID NO: 19, and a heavy chain variable region (VH) that comprises the amino acid sequence of SEQ ID NO: 23;

11) A light chain variable region (VL) that comprises the amino acid sequence of SEQ ID NO: 19, and a heavy chain variable region (VH) that comprises the amino acid sequence of SEQ ID NO: 27; or 12) A light chain variable region (VL) that comprises the amino acid sequence of SEQ ID NO: 19, and a heavy chain variable region (VH) that comprises the amino acid sequence of SEQ ID NO: 31.

4. The monoclonal antibody or antigen-binding fragment thereof of claim 1, comprising:

1) A light chain that comprises an amino acid sequence with at least 85% identity to the amino acid sequence of SEQ ID NO: 9, and a heavy chain that comprises an amino acid sequence with at least 85% identity to the amino acid sequence of SEQ ID NO: 25;

2) A light chain that comprises an amino acid sequence with at least 85% identity to the amino acid sequence of SEQ ID NO: 9, and a heavy chain that comprises an amino acid sequence with at least 85% identity to the amino acid sequence of SEQ ID NO: 29;

3) A light chain that comprises an amino acid sequence with at least 85% identity to the amino acid sequence of SEQ ID NO: 9, and a heavy chain that comprises an amino acid sequence with at least 85% identity to the amino acid sequence of SEQ ID NO: 33;

4) A light chain that comprises an amino acid sequence with at least 85% identity to the amino acid sequence of SEQ ID NO: 13, and a heavy chain that comprises an amino acid sequence with at least 85% identity to the amino acid sequence of SEQ ID NO: 25;

5) A light chain that comprises an amino acid sequence with at least 85% identity to the amino acid sequence of SEQ ID NO: 13, and a heavy chain that comprises an amino acid sequence with at least 85% identity to the amino acid sequence of SEQ ID NO: 29;

6) A light chain that comprises an amino acid sequence with at least 85% identity to the amino acid sequence of SEQ ID NO: 13, and a heavy chain that comprises an amino acid sequence with at least 85% identity to the amino acid sequence of SEQ ID NO: 33;

7) A light chain that comprises an amino acid sequence with at least 85% identity to the amino acid sequence of SEQ ID NO: 17, and a heavy chain that comprises an amino acid sequence with at least 85% identity to the amino acid sequence of SEQ ID NO: 25;

8) A light chain that comprises an amino acid sequence with at least 85% identity to the amino acid sequence of SEQ ID NO: 17, and a heavy chain that comprises an amino acid sequence with at least 85% identity to the amino acid sequence of SEQ ID NO: 29;

9) A light chain that comprises an amino acid sequence with at least 85% identity to the amino acid sequence of SEQ ID NO: 17, and a heavy chain that comprises an amino acid sequence with at least 85% identity to the amino acid sequence of SEQ ID NO: 33;

10) A light chain that comprises an amino acid sequence with at least 85% identity to the amino acid sequence of SEQ ID NO: 21, and a heavy chain that comprises an amino acid sequence with at least 85% identity to the amino acid sequence of SEQ ID NO: 25;

11) A light chain that comprises an amino acid sequence with at least 85% identity to the amino acid sequence of SEQ ID NO: 21, and a heavy chain that comprises an amino acid sequence with at least 85% identity to the amino acid sequence of SEQ ID NO: 29; or 12) A light chain that comprises an amino acid sequence with at least 85% identity to the amino acid sequence of SEQ ID NO: 21, and a heavy chain that comprises an amino acid sequence with at least 85% identity to the amino acid sequence of SEQ ID NO: 33.

5. The monoclonal antibody or antigen-binding fragment thereof of claim 1, comprising:

1) A light chain that comprises the amino acid sequence of SEQ ID NO: 9, and a heavy chain that comprises the amino acid sequence of SEQ ID NO: 25;

2) A light chain that comprises the amino acid sequence of SEQ ID NO: 9, and a heavy chain that comprises the amino acid sequence of SEQ ID NO: 29;

3) A light chain that comprises the amino acid sequence of SEQ ID NO: 9, and a heavy chain that comprises the amino acid sequence of SEQ ID NO: 33;

4) A light chain that comprises the amino acid sequence of SEQ ID NO: 13, and a heavy chain that comprises the amino acid sequence of SEQ ID NO: 25;

5) A light chain that comprises the amino acid sequence of SEQ ID NO: 13, and a heavy chain that comprises the amino acid sequence of SEQ ID NO: 29;

6) A light chain that comprises the amino acid sequence of SEQ ID NO: 13, and a heavy chain that comprises the amino acid sequence of SEQ ID NO: 33;

7) A light chain that comprises the amino acid sequence of SEQ ID NO: 17, and a heavy chain that comprises the amino acid sequence of SEQ ID NO: 25;

8) A light chain that comprises the amino acid sequence of SEQ ID NO: 17, and a heavy chain that comprises the amino acid sequence of SEQ ID NO: 29;

9) A light chain that comprises the amino acid sequence of SEQ ID NO: 17, and a heavy chain that comprises the amino acid sequence of SEQ ID NO: 33;

10) A light chain that comprises the amino acid sequence of SEQ ID NO: 21, and a heavy chain that comprises the amino acid sequence of SEQ ID NO: 25;

11) A light chain that comprises the amino acid sequence of SEQ ID NO: 21, and a heavy chain that comprises the amino acid sequence of SEQ ID NO: 29; or 12) a light chain that comprises the amino acid sequence of SEQ ID NO: 21, and a heavy chain that comprises the amino acid sequence of SEQ ID NO: 33.

6. The monoclonal antibody or antigen-binding fragment thereof of claim 1, wherein the monoclonal antibody is an IgG.

7. The monoclonal antibody or antigen-binding fragment thereof of claim 6, wherein the monoclonal IgG antibody is an IgG1, IgG2 or IgG4.

8. The monoclonal antibody or antigen-binding fragment thereof of claim 1, which is a chimeric antibody, a humanized antibody, a bispecific antibody, Fv, an scFv, a Fab, a Fab', a Fab'-SH or a F(ab')$_2$.

9. A pharmaceutical composition comprising a therapeutically effective amount of the monoclonal antibody or antigen-binding fragment thereof of claim 1, and a pharmaceutical acceptable excipient.

* * * * *

```
                           SEQUENCE LISTING

<160> NUMBER OF SEQ ID NOS: 86

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 1

Arg Ala Ser Glu Asn Ile Tyr Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 2

Asn Ala Lys Thr Leu Ala Glu
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 3

Gln His His Tyr Val Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 4

Ser Tyr Ala Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 5

Thr Ile Ser Ser Gly Gly Ser Asn Thr Tyr Ser Pro Asp Thr Val Lys
1               5                   10                  15

Gly

<210> SEQ ID NO 6
<211> LENGTH: 8
```

```
<212> TYPE: PRT
<213> ORGANISM: Artificial Sequence
<220> FEATURE:
<223> OTHER INFORMATION: synthetic polypeptide

<400> SEQUENCE: 6

Tyr Tyr Gly Tyr Tyr Phe Asp Phe
1               5

<210> SEQ ID NO 7
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg
            100                 105

<210> SEQ ID NO 8
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 8
gacatccaga tgacccagag ccccagcagc ctgagcgcca gcgtgggcga cagggtgacc      60
atcacctgca gggccagcga gaacatctac agctacctgg cctggtacca gcagaagccc     120
ggcaagagcc ccaagctgct ggtgtacaac gccaagaccc tggccgaggg cgtgcccagc     180
aggttcagcg gcagcggcag cggcaccgac ttcaccctga ccatcagcag cctgcagccc     240
gaggacttcg ccacctacta ctgccagcac cactacgtga ccccccctgac cttcggccag    300 ggcaccaagc tggagatcaa gagg                                            324

<210> SEQ ID NO 9
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30
```

```
Leu Ala Trp Tyr Gln Gln Lys Pro Gly Lys Ser Pro Lys Leu Leu Val
            35                  40                  45

Tyr Asn Ala Lys Thr Leu Ala Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Val Thr Pro Leu
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 10
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 10

```
gacatccaga tgacccagag ccccagcagc ctgagcgcca gcgtgggcga cagggtgacc      60
atcacctgca gggccagcga gaacatctac agctacctgg cctggtacca gcagaagccc     120
ggcaagagcc ccaagctgct ggtgtacaac gccaagaccc tggccgaggg cgtgcccagc     180
aggttcagcg gcagcggcag cggcaccgac ttcaccctga ccatcagcag cctgcagccc     240
gaggacttcg ccacctacta ctgccagcac cactacgtga cccccctgac cttcggccag     300
ggcaccaagc tggagatcaa gaggaccgtg gccgccccca gcgtgttcat cttcccccc      360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag cacactgacc     540
ctgagcaagg ccgactacga gaagcacaag gtgtacgcct gcgaggtgac ccaccagggc     600
ctgagcagcc ccgtgaccaa gagcttcaac agggcgagt gc                        642
```

<210> SEQ ID NO 11
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 11

Asp Ile His Met Thr Gln Ser Pro Ser Ser Leu Ser Ala Ser Val Gly

```
1               5                   10                  15
Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ser Pro Lys Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg
            100                 105
```

<210> SEQ ID NO 12
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 12

```
gacatccaca tgacccagag ccccagcagc ctgagcgcca gcgtgggcga cagggtgacc      60
atcacctgca gggccagcga gaacatctac agctacctgg cctggtacca gcagaagccc     120
ggcaagagcc ccaagctgct ggtgtacaac gccaagaccc tggccgaggg cgtgcccagc     180
aggttcagcg gcagcggcag cggcaccgac ttcaccctga ccatcagcag cctgcagccc     240
gaggacttcg ccacctacta ctgccagcac cactacgtga ccccccctgac cttcggccag     300
ggcaccaagc tggagatcaa gagg                                            324
```

<210> SEQ ID NO 13
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 13

```
Asp Ile His Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ser Pro Lys Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 14
gacatccaca tgacccagag ccccagcagc ctgagcgcca gcgtgggcga cagggtgacc      60
atcacctgca gggccagcga gaacatctac agctacctgg cctggtacca gcagaagccc     120
ggcaagagcc ccaagctgct ggtgtacaac gccaagaccc tggccgaggg cgtgcccagc     180
aggttcagcg gcagcggcag cggcaccgac ttcaccctga ccatcagcag cctgcagccc     240
gaggacttcg ccacctacta ctgccagcac cactacgtga ccccccctgac cttcggccag     300 ggcaccaagc tggagatcaa gaggaccgtg gccgccccca gcgtgttcat cttccccccc     360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac agggcgagt gc                        642

<210> SEQ ID NO 15
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 15

Asp Ile His Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Val Thr Pro Leu
            85                  90                  95

Thr Phe Gly Gln Gly Thr Lys Leu Glu Ile Lys Arg
            100                 105

<210> SEQ ID NO 16
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 16

```
gacatccaca tgacccagag ccccagcagc ctgagcgcca gcgtgggcga cagggtgacc      60
atcacctgca gggccagcga gaacatctac agctacctgg cctggtacca gcagaagccc     120
ggcaagagcc cccagctgct ggtgtacaac gccaagaccc tggccgaggg cgtgcccagc     180
aggttcagcg gcagcggcag cggcacccag ttcacccctg accatcagca gcctgcagcc     240
gaggacttcg ccacctacta ctgccagcac cactacgtga ccccccctga cttcggccag     300
ggcaccaagc tggagatcaa gagg                                            324
```

<210> SEQ ID NO 17
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 17

Asp Ile His Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 642
<212> TYPE: DNA
<213> ORGANISM: Artificial Sequence
<220> FEATURE:

<223> OTHER INFORMATION: synthetic polynucleotide

<400> SEQUENCE: 18

```
gacatccaca tgacccagag ccccagcagc ctgagcgcca gcgtgggcga cagggtgacc      60
atcacctgca gggccagcga gaacatctac agctacctgg cctggtacca gcagaagccc     120
ggcaagagcc cccagctgct ggtgtacaac gccaagaccc tggccgaggg cgtgcccagc     180
aggttcagcg gcagcggcag cggcacccag ttcaccctga ccatcagcag cctgcagccc     240
gaggacttcg ccacctacta ctgccagcac cactacgtga ccccctgac cttcggccag      300
ggcaccaagc tggagatcaa ggaccgtg ccgccccca gcgtgttcat cttcccccc         360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac agggggcgagt gc                        642
```

<210> SEQ ID NO 19
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 19

```
Asp Ile His Met Thr Gln Ser Pro Ser Ser Leu Ser Ala Ser Val Gly
1               5                   10                  15
Asp Arg Val Thr Ile Thr Cys Arg Ala Ser Glu Asn Ile Tyr Ser Tyr
            20                  25                  30
Leu Ala Trp Tyr Gln Gln Lys Gln Gly Lys Ser Pro Gln Leu Leu Val
        35                  40                  45
Tyr Asn Ala Lys Thr Leu Ala Glu Gly Val Pro Ser Arg Phe Ser Gly
    50                  55                  60
Ser Gly Ser Gly Thr Gln Phe Thr Leu Lys Ile Asn Ser Leu Gln Pro
65                  70                  75                  80
Glu Asp Phe Ala Thr Tyr Tyr Cys Gln His His Tyr Val Thr Pro Leu
                85                  90                  95
Thr Phe Gly Gln Gly Thr Lys Leu Glu Ile Lys Arg
            100                 105
```

<210> SEQ ID NO 20
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 20

```
gacatccaca tgacccagag ccccagcagc ctgagcgcca gcgtgggcga cagggtgacc      60
atcacctgca gggccagcga gaacatctac agctacctgg cctggtacca gcagaagcag     120
ggcaagagcc cccagctgct ggtgtacaac gccaagaccc tggccgaggg cgtgcccagc     180
aggttcagcg gcagcggcag cggcacccag ttcaccctga agatcaacag cctgcagccc     240
gaggacttcg ccacctacta ctgccagcac cactacgtga ccccctgac cttcggccag      300
ggcaccaagc tggagatcaa gagg                                             324
```

<210> SEQ ID NO 21
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 21

```
Asp Ile His Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Lys Ile Asn Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 22
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 22

```
gacatccaca tgacccagag ccccagcagc ctgagcgcca gcgtgggcga caggggtgacc    60
atcacctgca gggccagcga gaacatctac agctacctgg cctggtacca gcagaagcag   120
ggcaagagcc cccagctgct ggtgtacaac gccaagaccc tggccgaggg cgtgcccagc   180
aggttcagcg gcagcggcag cggcacccag ttcaccctga agatcaacag cctgcagccc   240
gaggacttcg ccacctacta ctgccagcac cactacgtga ccccctgac cttcggccag   300
ggcaccaagc tggagatcaa gaggaccgtg gccgccccca gcgtgttcat cttcccccc    360
agcgacgagc agctgaagag cggcaccgcc agcgtggtgt gcctgctgaa caacttctac   420
cccagggagg ccaaggtgca gtggaaggtg gacaacgccc tgcagagcgg caacagccag   480
gagagcgtga ccgagcagga cagcaaggac agcacctaca gcctgagcag caccctgacc   540
```

```
ctgagcaagg ccgactacga gaagcacaag gtgtacgcct gcgaggtgac ccaccagggc    600
ctgagcagcc ccgtgaccaa gagcttcaac aggggcgagt gc                      642
```

<210> SEQ ID NO 23
<211> LENGTH: 117
<212> TYPE: PRT
<213> ORGANISM: Artificial Sequence
<220> FEATURE:
<223> OTHER INFORMATION: synthetic polypeptide

<400> SEQUENCE: 23

```
Glu Val Met Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Gly Thr Gly Leu Glu Trp Val
        35                  40                  45

Ala Thr Ile Ser Ser Gly Gly Ser Asn Thr Tyr Ser Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Tyr Tyr Phe Asp Phe Trp Gly Gln Gly Thr Leu
            100                 105                 110

Leu Thr Val Ser Ser
        115
```

<210> SEQ ID NO 24
<211> LENGTH: 351
<212> TYPE: DNA
<213> ORGANISM: Artificial Sequence
<220> FEATURE:
<223> OTHER INFORMATION: synthetic polynucleotide

<400> SEQUENCE: 24

```
gaggtgatgc tgctggagag cggcggcggc ctggtgcagc ccggcggcag cctgaggctg    60
agctgcgccg ccagcggctt catcttcagc agctacgcca tgagctgggt gaggcaggcc   120
cccggcaccg gcctggagtg ggtggccacc atcagcagcg gcggcagcaa cacctacagc   180
cccgacaccg tgaagggcag gttcaccatc agcagggaca acagcaagaa cacccctgtac   240 ctgcagatga acagcctgag ggccgaggac accgccgtgt actactgcgc caggtactac   300
ggctactact tcgacttctg gggccagggc accctgctga ccgtgagcag c            351
```

<210> SEQ ID NO 25
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 25

```
Glu Val Met Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Gly Thr Gly Leu Glu Trp Val
        35                  40                  45
```

```
Ala Thr Ile Ser Ser Gly Gly Ser Asn Thr Tyr Ser Pro Asp Thr Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Gly Tyr Tyr Phe Asp Phe Trp Gly Gln Gly Thr Leu
            100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 26
<211> LENGTH: 1341
```

```
<212> TYPE: DNA
<213> ORGANISM: Artificial Sequence
<220> FEATURE:
<223> OTHER INFORMATION: synthetic polynucleotide

<400> SEQUENCE: 26
gaggtgatgc tgctggagag cggcggcggc ctggtgcagc ccggcggcag cctgaggctg     60
agctgcgccg ccagcggctt catcttcagc agctacgcca tgagctgggt gaggcaggcc    120
cccggcaccg gcctggagtg ggtggccacc atcagcagcg gcggcagcaa cacctacagc    180
cccgacaccg tgaagggcag gttcaccatc agcagggaca cagcaagaa caccctgtac     240
ctgcagatga acagcctgag ggccgaggac accgccgtgt actactgcgc caggtactac    300
ggctactact tcgacttctg gggccagggc accctgctga ccgtgagcag cgccagcacc    360
aagggcccca gcgtgttccc cctggccccc agcagcaaga gcaccagcgg cggcaccgcc    420
gccctgggct gcctggtgaa ggactacttc cccgagcccg tgaccgtgag ctggaacagc    480
ggcgccctga ccagcggcgt gcacaccttc cccgccgtgc tgcagagcag cggcctgtac    540
agcctgagca gcgtggtgac cgtgcccagc agcagcctgg gcacccagac ctacatctgc    600
aacgtgaacc acaagcccag caacaccaag gtggacaaga aggtggagcc caagagctgc    660
gacaagaccc acacctgccc cccctgcccc gcccccgagc tgctgggcgg ccccagcgtg    720
ttcctgttcc cccccaagcc caaggacacc ctgatgatca gcaggacccc cgaggtgacc    780
tgcgtggtgg tggacgtgag ccacgaggac cccgaggtga agttcaactg gtacgtggac    840
ggcgtggagg tgcacaacgc caagaccaag cccagggagg agcagtacaa cagcacctac    900
agggtggtga gcgtgctgac cgtgctgcac caggactggc tgaacggcaa ggagtacaag    960
tgcaaggtga gcaacaaggc cctgcccgcc cccatcgaga agaccatcag caaggccaag   1020
ggccagcccc gggagcccca ggtgtacacc ctgccccca gcagggagga gatgaccaag    1080
aaccaggtga gcctgacctg cctggtgaag ggcttctacc ccagcgacat cgccgtggag   1140
tgggagagca acggccagcc cgagaacaac tacaagacca ccccccccgt gctggacagc   1200
gacggcagct tcttcctgta cagcaagctg accgtggaca gagcaggtg gcagcagggc    1260
aacgtgttca gctgcagcgt gatgcacgag gccctgcaca accactacac ccagaagagc   1320
ctgagcctga gccccggcaa g                                            1341

<210> SEQ ID NO 27
<211> LENGTH: 117
<212> TYPE: PRT
<213> ORGANISM: Artificial Sequence
<220> FEATURE:
<223> OTHER INFORMATION: synthetic polypeptide

<400> SEQUENCE: 27

Glu Val Met Leu Val Glu Ser Gly Gly Gly Leu Val Gln Pro Gly Gly
1               5                   10                  15
Ser Leu Arg Leu Ser Cys Ala Ala Ser Gly Phe Ile Phe Ser Ser Tyr
            20                  25                  30
Ala Met Ser Trp Val Arg Gln Ala Pro Gly Thr Gly Leu Glu Trp Val
        35                  40                  45
Ala Thr Ile Ser Ser Gly Gly Ser Asn Thr Tyr Ser Pro Asp Thr Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Met Tyr Tyr Cys
```

```
                     85                  90                  95
Ala Arg Tyr Tyr Gly Tyr Tyr Phe Asp Phe Trp Gly Gln Gly Thr Leu
                100                 105                 110

Leu Thr Val Ser Ser
        115

<210> SEQ ID NO 28
<211> LENGTH: 351
<212> TYPE: DNA
<213> ORGANISM: Artificial Sequence
<220> FEATURE:
<223> OTHER INFORMATION: synthetic polynucleotide

<400> SEQUENCE: 28
gaggtgatgc tggtggagag cggcggcggc ctggtgcagc ccggcggcag cctgaggctg        60
agctgcgccg ccagcggctt catcttcagc agctacgcca tgagctgggt gaggcaggcc       120
cccggcaccg gcctggagtg ggtggccacc atcagcagcg gcggcagcaa cacctacagc       180
cccgacaccg tgaagggcag gttcaccatc agcagggaca cagcaagaa cccctgtac        240 ctgcagatga acagcctgag ggccgaggac accgccatgt actactgcgc caggtactac       300
ggctactact tcgacttctg gggccagggc accctgctga ccgtgagcag c                351

<210> SEQ ID NO 29
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 29

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Gly Thr Gly Leu Glu Trp Val
        35                  40                  45

Ala Thr Ile Ser Ser Gly Gly Ser Asn Thr Tyr Ser Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Tyr Tyr Gly Tyr Tyr Phe Asp Phe Trp Gly Gln Gly Thr Leu
                100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

<210> SEQ ID NO 30
<211> LENGTH: 1341
<212> TYPE: DNA
<213> ORGANISM: Artificial Sequence
<220> FEATURE:
<223> OTHER INFORMATION: synthetic polynucleotide

<400> SEQUENCE: 30

```
gaggtgatgc tggtggagag cggcggcggc ctggtgcagc ccggcggcag cctgaggctg      60
agctgcgccg ccagcggctt catcttcagc agctacgcca tgagctgggt gaggcaggcc     120
cccggcaccg gcctggagtg ggtggccacc atcagcagcg gcggcagcaa cacctacagc     180
cccgacaccg tgaagggcag gttcaccatc agcagggaca cagcaagaa caccctgtac     240
ctgcagatga acagcctgag ggccgaggac accgccatgt actactgcgc caggtactac     300
ggctactact cgacttctg ggccagggc accctgctga ccgtgagcag cgccagcacc     360
aagggcccca gcgtgttccc cctggccccc agcagcaaga gcaccagcgg cggcaccgcc     420
gccctgggct gcctggtgaa ggactacttc cccgagcccg tgaccgtgag ctggaacagc     480
ggcgccctga ccagcggcgt gcacaccttc cccgccgtgc tgcagagcag cggcctgtac     540
agcctgagca gcgtggtgac cgtgcccagc agcagcctgg gcacccagac ctacatctgc     600
aacgtgaacc acaagcccag caacaccaag gtggacaaga aggtggagcc caagagctgc     660
gacaagaccc acacctgccc ccctgccccc gcccccgagc tgctgggcgg ccccagcgtg     720
```

| | |
|---|---|
| ttcctgttcc cccccaagcc caaggacacc ctgatgatca gcaggacccc cgaggtgacc | 780 |
| tgcgtggtgg tggacgtgag ccacgaggac cccgaggtga agttcaactg gtacgtggac | 840 |
| ggcgtggagg tgcacaacgc caagaccaag cccagggagg agcagtacaa cagcacctac | 900 |
| agggtggtga gcgtgctgac cgtgctgcac caggactggc tgaacggcaa ggagtacaag | 960 |
| tgcaaggtga gcaacaaggc cctgcccgcc cccatcgaga agaccatcag caaggccaag | 1020 |
| ggccagccca gggagcccca ggtgtacacc ctgcccccca gcagggagga tgaccaag | 1080 |
| aaccaggtga gcctgacctg cctggtgaag ggcttctacc ccagcgacat cgccgtggag | 1140 |
| tgggagagca acggccagcc cgagaacaac tacaagacca cccccccgt gctggacagc | 1200 |
| gacggcagct tcttcctgta cagcaagctg accgtggaca agagcaggtg gcagcagggc | 1260 |
| aacgtgttca gctgcagcgt gatgcacgag gccctgcaca accactacac ccagaagagc | 1320 |
| ctgagcctga gccccggcaa g | 1341 |

<210> SEQ ID NO 31
<211> LENGTH: 117
<212> TYPE: PRT
<213> ORGANISM: Artificial Sequence
<220> FEATURE:
<223> OTHER INFORMATION: synthetic polypeptide

<400> SEQUENCE: 31

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Glu Thr Arg Leu Glu Trp Val
        35                  40                  45

Ala Thr Ile Ser Ser Gly Gly Ser Asn Thr Tyr Ser Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Tyr Tyr Gly Tyr Tyr Phe Asp Phe Trp Gly Gln Gly Thr Leu
            100                 105                 110

Leu Thr Val Ser Ser
        115

<210> SEQ ID NO 32
<211> LENGTH: 351
<212> TYPE: DNA
<213> ORGANISM: Artificial Sequence
<220> FEATURE:
<223> OTHER INFORMATION: synthetic polynucleotide

<400> SEQUENCE: 32

| | |
|---|---|
| gaggtgatgc tggtggagag cggcggcggc ctggtgcagc ccggcggcag cctgaggctg | 60 |
| agctgcgccg ccagcggctt catcttcagc agctacgcca tgagctgggt gaggcaggcc | 120 |
| ccgagacca ggctggagtg ggtggccacc atcagcagcg gcggcagcaa cacctacagc | 180 |
| cccgacaccg tgaagggcag gttcaccatc agcagggaca acagcaagaa caccctgtac | 240 |
| ctgcagatga acagcctgag ggccgaggac accgccatgt actactgcgc caggtactac | 300 |
| ggctactact tcgacttctg gggccagggc accctgctga ccgtgagcag c | 351 |

```
<210> SEQ ID NO 33
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 33

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Glu Thr Arg Leu Glu Trp Val
        35                  40                  45

Ala Thr Ile Ser Ser Gly Gly Ser Asn Thr Tyr Ser Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Tyr Tyr Gly Tyr Tyr Phe Asp Phe Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 34
<211> LENGTH: 1341
<212> TYPE: DNA
<213> ORGANISM: Artificial Sequence
<220> FEATURE:
<223> OTHER INFORMATION: synthetic polynucleotide

<400> SEQUENCE: 34
gaggtgatgc tggtggagag cggcggcggc ctggtgcagc cggcggcag cctgaggctg      60 agctgcgccg ccagcggctt catcttcagc agctacgcca tgagctgggt gaggcaggcc    120
cccgagacca ggctggagtg ggtggccacc atcagcagcg gcggcagcaa cacctacagc    180
cccgacaccg tgaagggcag gttcaccatc agcagggaca acagcaagaa caccctgtac    240
ctgcagatga acagcctgag ggccgaggac accgccatgt actactgcgc caggtactac    300
ggctactact cgacttctg gggccagggc accctgctga ccgtgagcag cgccagcacc    360
aagggcccca gcgtgttccc cctggccccc agcagcaaga gcaccagcgg cggcaccgcc    420
gccctgggct gcctggtgaa ggactacttc cccgagcccg tgaccgtgag ctggaacagc    480
ggcgccctga ccagcggcgt gcacaccttc cccgccgtgc tgcagagcag cggcctgtac    540
agcctgagca gcgtggtgac cgtgcccagc agcagcctgg gcacccagac ctacatctgc    600
aacgtgaacc acaagcccag caacaccaag gtggacaaga aggtggagcc caagagctgc    660
gacaagaccc acacctgccc ccctgccccc gccccgagc tgctgggcgg cccccagcgtg   720 ttcctgttcc cccccaagcc caaggacacc ctgatgatca gcaggacccc cgaggtgacc    780
tgcgtggtgg tggacgtgag ccacgaggac cccgaggtga agttcaactg gtacgtggac    840
ggcgtggagg tgcacaacgc caagaccaag cccagggagg agcagtacaa cagcacctac    900
agggtggtga gcgtgctgac cgtgctgcac caggactggc tgaacggcaa ggagtacaag    960
tgcaaggtga gcaacaaggc cctgcccgcc cccatcgaga agaccatcag caaggccaag   1020
ggccagcccc gggagcccca ggtgtacacc ctgcccccca gcagggagga gatgaccaag   1080
aaccaggtga gcctgacctg cctggtgaag ggcttctacc ccagcgacat cgccgtggag   1140
tgggagagca acggccagcc cgagaacaac tacaagacca ccccccccgt gctggacagc   1200
gacggcagct tcttcctgta cagcaagctg accgtggaca gagcaggtg gcagcagggc   1260 aacgtgttca gctgcagcgt gatgcacgag gccctgcaca accactacac ccagaagagc   1320
ctgagcctga gccccggcaa g                                              1341

<210> SEQ ID NO 35
<211> LENGTH: 441
<212> TYPE: PRT
<213> ORGANISM: Artificial Sequence
<220> FEATURE:
<223> OTHER INFORMATION: synthetic polypeptide

<400> SEQUENCE: 35

```
Glu Val Met Leu Val Glu Ser Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Glu Thr Arg Leu Glu Trp Val
        35                  40                  45

Ala Thr Ile Ser Ser Gly Gly Ser Asn Thr Tyr Ser Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Tyr Tyr Gly Tyr Tyr Phe Asp Phe Trp Gly Gln Gly Thr Leu
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
            245                 250                 255

Val Val Asp Ile Ser Lys Asp Asp Pro Glu Val Gln Phe Ser Trp Phe
        260                 265                 270

Val Asp Asp Val Glu Val His Thr Ala Gln Thr Gln Pro Arg Glu Glu
    275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
            325                 330                 335

Pro Lys Ala Pro Gln Val Tyr Thr Ile Pro Pro Pro Lys Glu Gln Met
        340                 345                 350

Ala Lys Asp Lys Val Ser Leu Thr Cys Met Ile Thr Asp Phe Phe Pro
    355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
            405                 410                 415
```

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 36
<211> LENGTH: 1323
<212> TYPE: DNA
<213> ORGANISM: Artificial Sequence
<220> FEATURE:
<223> OTHER INFORMATION: synthetic polynucleotide

<400> SEQUENCE: 36

```
gaggtgatgc tggtggagag cggcggcggc ctggtgcagc ccggcggcag cctgaggctg      60
agctgcgccg ccagcggctt catcttcagc agctacgcca tgagctgggt gaggcaggcc     120
cccgagacca ggctggagtg ggtggccacc atcagcagcg gcggcagcaa cacctacagc     180
cccgacaccg tgaagggcag gttcaccatc agcagggaca cagcaagaa caccctgtac      240
ctgcagatga acagcctgag ggccgaggac accgccatgt actactgcgc caggtactac     300
ggctactact cgacttctg gggccagggc accctgctga ccgtgagcag cgccaagacc      360
acccccccca gcgtgtaccc cctggccccc ggcagcgccg cccagaccaa cagcatggtg     420
accctgggct gcctggtgaa gggctacttc cccgagcccg tgaccgtgac ctggaacagc     480
ggcagcctga gcagcggcgt gcacaccttc ccgccgtgc tgcagagcga cctgtacacc      540
ctgagcagca gcgtgaccgt gcccagcagc acctggccca gcgagaccgt gacctgcaac     600
gtggcccacc ccgccagcag caccaaggtg gacaagaaga tcgtgcccag ggactgcggc     660
tgcaagccct gcatctgcac cgtgcccgag gtgagcagcg tgttcatctt ccccccccaag    720
cccaaggacg tgctgaccat caccctgacc cccaaggtga cctgcgtggt ggtggacatc     780
agcaaggacg accccgaggt gcagttcagc tggttcgtgg acgacgtgga ggtgcacacc     840
gcccagaccc agcccaggga ggagcagttc aacagcacct tcaggagcgt gagcgagctg     900
cccatcatgc accaggactg gctgaacggc aaggagttca gtgcagggt gaacagcgcc     960
gccttccccg cccccatcga aagaccatc agcaaggaca agggcaggcc caaggccccc    1020
caggtgtaca ccatcccccc ccccaaggag cagatggcca aggacaaggt gagcctgacc    1080
tgcatgatca ccgacttctt cccccgaggac atcaccgtgg agtggcagtg gaacggccag    1140
cccgccgaga actacaagaa cacccagccc atcatggaca ccgacggcag ctacttcgtg    1200
tacagcaagc tgaacgtgca gaagagcaac tgggaggccg gcaacacctt cacctgcagc    1260
gtgctgcacg agggcctgca caaccaccac accgagaaga gcctgagcca cagccccggc    1320
aag                                                                  1323
```

<210> SEQ ID NO 37
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 37

Asp Ile His Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Val

```
                35                  40                  45
Tyr Asn Ala Lys Thr Leu Ala Glu Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Tyr Val Thr Pro Leu
                 85                  90                  95

Thr Phe Gly Gln Gly Thr Lys Leu Glu Ile Lys Arg Ala Asp Ala Ala
                100                 105                 110

Pro Thr Val Ser Ile Phe Pro Pro Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210
```

<210> SEQ ID NO 38
<211> LENGTH: 642
<212> TYPE: DNA
<213> ORGANISM: Artificial Sequence
<220> FEATURE:
<223> OTHER INFORMATION: synthetic nucleotide

<400> SEQUENCE: 38

```
gacatccaca tgacccagag ccccagcagc ctgagcgcca gcgtgggcga cagggtgacc      60
atcacctgca gggccagcga gaacatctac agctacctgg cctggtacca gcagaagccc     120
ggcaagagcc ccaagctgct ggtgtacaac gccaagaccc tggccgaggg cgtgcccagc     180
aggttcagcg gcagcggcag cggcaccgac ttcaccctga ccatcagcag cctgcagccc     240
gaggacttcg ccacctacta ctgccagcac cactacgtga cccccctgac cttcggccag     300
ggcaccaagc tggagatcaa gagggccgac gccgccccca cgtgagcat cttcccccc      360
agcagcgagc agctgaccag cggcggcgcc agcgtggtgt gcttcctgaa caacttctac     420
cccaaggaca tcaacgtgaa gtggaagatc gacggcagcg agaggcagaa cggcgtgctg     480
aacagctgga ccgaccagga cagcaaggac agcacctaca gcatgagcag caccctgacc     540
ctgaccaagg acgagtacga gaggcacaac agctacacct gcgaggccac ccacaagacc     600
agcaccagcc ccatcgtgaa gagcttcaac aggaacgagt gc                         642
```

<210> SEQ ID NO 39
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 39

```
Asp Ile His Met Thr Gln Ser Pro Ser Ser Leu Ser Ala Ser Val Gly
 1               5                  10                  15
```

Asp Arg Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Thr Leu Lys Ile Asn Ser Leu Gln Pro
65                  70                  75                  80

Glu Asp Phe Ala Thr Tyr Tyr Cys Gln His His Tyr Val Thr Pro Leu
                85                  90                  95

Thr Phe Gly Gln Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 40
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 40
gacatccaca tgacccagag ccccagcagc ctgagcgcca gcgtgggcga cagggtgacc     60
atcacctgca gggccagcga gaacatctac agctacctgg cctggtacca gcagaagcag    120
ggcaagagcc cccagctgct ggtgtacaac gccaagaccc tggccgaggg cgtgcccagc    180
aggttcagcg gcagcggcag cggcacccag ttcaccctga agatcaacag cctgcagccc    240
gaggacttcg ccacctacta ctgccagcac cactacgtga cccccctgac cttcggccag    300
ggcaccaagc tggagatcaa gaggaccgtg gccgccccca gcgtgttcat cttcccccc     360
agcgacgagc agctgaagag cggcaccgcc agcgtggtgt gcctgctgaa caacttctac    420
cccagggagg ccaaggtgca gtggaaggtg gacaacgccc tgcagagcgg caacagccag    480
gagagcgtga ccgagcagga cagcaaggac agcacctaca gcctgagcag cacccctgacc   540
ctgagcaagg ccgactacga gaagcacaag gtgtacgcct gcgaggtgac ccaccagggc    600
ctgagcagcc ccgtgaccaa gagcttcaac aggggcgagt gc                       642

<210> SEQ ID NO 41
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 41

```
Asp Ile His Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 42
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 42

```
gacatccaca tgactcagtc tccagcctcc ctatctgcat ctgtgggaga aactgtcacc    60
atcacatgtc gagcaagtga gaatatttac agttatttag catggtatca gcagaaacag   120
ggaaaatctc ctcagctcct ggtctataat gcaaaaacct agcagaagg tgtgccatca    180
aggttcagtg gcagtggatc aggcacacag ttttctctga agatcaacag cctgcagcct   240
gaagattttg ggagttatta ctgtcaacat cattatgtta ctccgctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cacccctcacg  540
ttgaccaagg acgagtatga acgacataac agctatacct gtgaggccac tcacaagaca   600
tcaacttcac ccattgtcaa gagcttcaac aggaatgagt gt                      642
```

<210> SEQ ID NO 43

```
<211> LENGTH: 441
<212> TYPE: PRT
<213> ORGANISM: Artificial Sequence
<220> FEATURE:
<223> OTHER INFORMATION: synthetic polypeptide

<400> SEQUENCE: 43

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser Tyr
            20                  25                  30

Ala Met Ser Trp Val Arg Gln Ser Pro Glu Thr Arg Leu Glu Trp Val
        35                  40                  45

Ala Thr Ile Ser Ser Gly Gly Ser Asn Thr Tyr Ser Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Tyr Tyr Gly Tyr Tyr Phe Asp Phe Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380
```

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
            405                 410                 415

Phe Thr Cys Ser Val Leu His Glu Gly Leu His Asn His His Thr Glu
        420                 425                 430

Lys Ser Leu Ser His Ser Pro Gly Lys
        435                 440

<210> SEQ ID NO 44
<211> LENGTH: 1323
<212> TYPE: DNA
<213> ORGANISM: Artificial Sequence
<220> FEATURE:
<223> OTHER INFORMATION: synthetic polynucleotide

<400> SEQUENCE: 44

| | | | | | |
|---|---|---|---|---|---|
| gaagtgatgc | tggtggagtc | tgggggaggc | ttagtgaagc | ctggagggtc | cctgaaactc | 60 |
| tcctgtgcag | cctctggatt | cattttcagt | agttatgcca | tgtcttgggt | tcgccagagt | 120 |
| ccggagacga | ggctggagtg | ggtcgcaacc | attagtagtg | gtggtagtaa | cacctactct | 180 |
| ccagacagtg | tgaaggggcg | attcaccatc | tccagagaca | atgccaagaa | caccctgtac | 240 |
| ctgcaaatga | gcagtctgag | gtctgaggac | acggccatgt | attactgtgc | aagatattat | 300 |
| ggttactact | ttgacttctg | gggccaaggc | accactctca | cagtctcctc | agccaaaacg | 360 |
| acacccccat | ctgtctatcc | actggcccct | ggatctgctg | cccaaactaa | ctccatggtg | 420 |
| accctgggat | gcctggtcaa | gggctatttc | cctgagccag | tgacagtgac | ctggaactct | 480 |
| ggatccctgt | ccagcggtgt | gcacaccttc | ccagctgtcc | tgcagtctga | cctctacact | 540 |
| ctgagcagct | cagtgactgt | cccctccagc | acctggccca | gcgagaccgt | cacctgcaac | 600 |
| gttgcccacc | cggccagcag | caccaaggtg | gacaagaaaa | ttgtgcccag | ggattgtggt | 660 |
| tgtaagcctt | gcatatgtac | agtcccagaa | gtatcatctg | tcttcatctt | ccccccaaag | 720 |
| cccaaggatg | tgctcaccat | tactctgact | cctaaggtca | cgtgtgttgt | ggtagacatc | 780 |
| agcaaggatg | atcccgaggt | ccagttcagc | tggtttgtag | atgatgtgga | ggtgcacaca | 840 |
| gctcagacgc | aaccccggga | ggagcagttc | aacagcactt | tccgctcagt | cagtgaactt | 900 |
| cccatcatgc | accaggactg | gctcaatggc | aaggagttca | atgcagggt | caacagtgca | 960 |
| gctttccctg | cccccatcga | gaaaaccatc | tccaaaacca | aaggcagacc | gaaggctcca | 1020 |
| caggtgtaca | ccattccacc | tcccaaggag | cagatggcca | aggataaagt | cagtctgacc | 1080 |
| tgcatgataa | cagacttctt | ccctgaagac | attactgtgg | agtggcagtg | gaatgggcag | 1140 |
| ccagcggaga | actacaagaa | cactcagccc | atcatggaca | cagatggctc | ttacttcgtc | 1200 |
| tacagcaagc | tcaatgtgca | gaagagcaac | tgggaggcag | gaaatacttt | cacctgctct | 1260 |
| gtgttacatg | agggcctgca | caaccaccat | actgagaaga | gcctctccca | ctctcctggt | 1320 |
| aaa | | | | | | 1323 |

<210> SEQ ID NO 45
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 45

Thr Ile Ser Ser Gly Gly Ser Asn Thr Tyr Ser Pro Asp Ser Val Lys
1               5                   10                  15

Gly

<210> SEQ ID NO 46
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 46

Asp Ile His Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Leu
                85                  90                  95

Thr Phe Gly Ala Gly Thr Lys Leu Glu Leu Lys Arg
            100                 105

<210> SEQ ID NO 47
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 47
gacatccaca tgactcagtc tccagcctcc ctatctgcat ctgtgggaga aactgtcacc     60
atcacatgtc gagcaagtga gaatatttac agttatttag catggtatca gcagaaacag    120
ggaaaatctc ctcagctcct gtctataatg caaaaacctt agcagaaggt gtgccatcaa    180
ggttcagtgg cagtggatca ggcacacatt ttctctgaag atcaacagcc tgcagcctga    240
agattttggg agttattact gtcaacatca ttatgttact ccgctcacgt tcggtgctgg    300
gaccaagctg gagctgaaac gggc                                           324

<210> SEQ ID NO 48
<211> LENGTH: 117
<212> TYPE: PRT
<213> ORGANISM: Artificial Sequence
<220> FEATURE:
<223> OTHER INFORMATION: synthetic polypeptide

<400> SEQUENCE: 48

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser Tyr
            20                  25                  30

Ala Met Ser Trp Val Arg Gln Ser Pro Glu Thr Arg Leu Glu Trp Val
        35                  40                  45

Ala Thr Ile Ser Ser Gly Gly Ser Asn Thr Tyr Ser Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Tyr Tyr Gly Tyr Tyr Phe Asp Phe Trp Gly Gln Gly Thr Thr
            100                 105                 110

Leu Thr Val Ser Ser
        115

<210> SEQ ID NO 49
<211> LENGTH: 351
<212> TYPE: DNA
<213> ORGANISM: Artificial Sequence
<220> FEATURE:
<223> OTHER INFORMATION: synthetic polynucleotide

<400> SEQUENCE: 49
gaagtgatgc tggtggagtc tgggggaggc ttagtgaagc ctggagggtc cctgaaactc    60
tcctgtgcag cctctggatt cattttcagt agttatgcca tgtcttgggt tcgccagagt   120
ccggagacga ggctggagtg ggtcgcaacc attagtagtg gtggtagtaa cacctactct   180
ccagacagtg tgaaggggcg attcaccatc tccagagaca atgccaagaa caccctgtac   240
ctgcaaatga gcagtctgag gtctgaggac acggccatgt attactgtgc aagatattat   300
ggttactact ttgacttctg gggccaaggc accactctca cagtctcctc a            351

<210> SEQ ID NO 50
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 50

Asp Ile His Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
            180                 185                 190
Ala Cys Glu Val Thr His Gln Gly Leu Ser Ser Pro Val Thr Lys Ser
            195                 200                 205

Phe Asn Arg Gly Glu Cys
            210

<210> SEQ ID NO 51
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 51
gacatccaca tgacccagag ccccgccagc ctgagcgcca gcgtgggcga gaccgtgacc      60
atcacctgca gggccagcga gaacatctac agctacctgg cctggtacca gcagaagcag     120
ggcaagagcc cccagctgct ggtgtacaac gccaagaccc tggccgaggg cgtgcccagc     180
aggttcagcg gcagcggcag cggcacccag ttcagcctga gatcaacag cctgcagccc      240 gaggacttcg gcagctacta ctgccagcac cactacgtga cccccctgac cttcggcgcc     300
ggcaccaagc tggagctgaa gaggaccgtg gccgccccca gcgtgttcat cttccccccc     360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac aggggcgagt gc                        642

<210> SEQ ID NO 52
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 52

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser Tyr
            20                  25                  30

Ala Met Ser Trp Val Arg Gln Ser Pro Glu Thr Arg Leu Glu Trp Val
            35                  40                  45

Ala Thr Ile Ser Ser Gly Gly Ser Asn Thr Tyr Ser Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Tyr Tyr Gly Tyr Tyr Phe Asp Phe Trp Gly Gln Gly Thr Thr
            100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 53
<211> LENGTH: 1341
<212> TYPE: DNA
<213> ORGANISM: Artificial Sequence
<220> FEATURE:
<223> OTHER INFORMATION: synthetic polypeptide

<400> SEQUENCE: 53
gaggtgatgc tggtggagag cggcggcggc ctggtgaagc ccggcggcag cctgaagctg    60
agctgcgccg ccagcggctt catcttcagc agctacgcca tgagctgggt gaggcagagc   120
cccgagacca ggctggagtg gtggccacc atcagcagcg gcggcagcaa cacctacagc   180
cccgacagcg tgaagggcag gttcaccatc agcagggaca cgccaagaa caccctgtac   240 ctgcagatga gcagcctgag gagcgaggac accgccatgt actactgcgc caggtactac   300
ggctactact tcgacttctg gggccagggc accaccctga ccgtgagcag cgccagcacc   360
aagggcccca gcgtgttccc cctggccccc agcagcaaga gcaccagcgg cggcaccgcc   420
```

```
gccctgggct gcctggtgaa ggactacttc cccgagcccg tgaccgtgag ctggaacagc    480
ggcgccctga ccagcggcgt gcacaccttc ccgccgtgc tgcagagcag cggcctgtac     540
agcctgagca gcgtggtgac cgtgcccagc agcagcctgg gcacccagac ctacatctgc    600
aacgtgaacc acaagcccag caacaccaag gtggacaaga aggtggagcc caagagctgc    660
gacaagaccc acacctgccc ccctgccccc gccccgagc tgctgggcgg ccccagcgtg     720
ttcctgttcc cccccaagcc caaggacacc ctgatgatca gcaggacccc cgaggtgacc    780
tgcgtggtgg tggacgtgag ccacgaggac cccgaggtga agttcaactg gtacgtggac    840
ggcgtggagg tgcacaacgc caagaccaag cccagggagg agcagtacaa cagcaccttac   900 agggtggtga gcgtgctgac cgtgctgcac caggactggc tgaacggcaa ggagtacaag    960
tgcaaggtga gcaacaaggc cctgcccgcc cccatcgaga agaccatcag caaggccaag   1020
ggccagcccc gggagcccca ggtgtacacc ctgcccccca gcagggagga tgaccaag     1080 aaccaggtga gcctgacctg cctggtgaag ggcttctacc ccagcgacat cgccgtggag   1140
tgggagagca acggccagcc cgagaacaac tacaagacca ccccccccgt gctggacagc   1200
gacggcagct tcttcctgta cagcaagctg accgtggaca agagcaggtg gcagcagggc   1260
aacgtgttca gctgcagcgt gatgcacgag gccctgcaca accactacac ccagaagagc   1320
ctgagcctga gccccggcaa g                                             1341
```

<210> SEQ ID NO 54
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 54

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Asn Ala
            20                  25                  30

Val Ala Trp Tyr Gln Gln Lys Pro Gly Gln Ser Pro Arg Leu Leu Ile
        35                  40                  45

Tyr Trp Ala Ser Phe Arg His Thr Gly Val Pro Asp Arg Phe Thr Gly
    50                  55                  60

Ser Gly Ser Gly Thr Glu Tyr Thr Leu Thr Ile Ser Arg Val Gln Ala
65                  70                  75                  80

Glu Asp Leu Ala Leu Tyr Tyr Cys Gln Gln His Tyr Asn Thr Pro Tyr
                85                  90                  95

Thr Phe Gly Gly Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
```

Phe Asn Arg Asn Glu Cys
    210

<210> SEQ ID NO 55
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 55
gacatcgtga tgacccagtc ccacaagttc atgagcacca gcgtgggcga tcgggtgtcc      60
atcacctgta aggcctccca ggacgtgagc aacgccgtgg cctggtatca gcagaagcct     120
ggccagtccc ctcggctgct gatctattgg gcttccttca gcacaccgg cgtgcccgat      180 cggttcaccg gctccggatc cggcaccgag tataccctga ccatctcccg ggtgcaggcc     240
gaggatctgg ctctgtatta ttgtcagcag cactacaata cccctacac cttcggcggc      300 ggcaccaggc tggagatcaa gagagctgat gctgccccca ccgtgagcat cttccctccc    360
tccagcgagc agctgacctc cggcggagcc tccgtggtgt gcttcctgaa caacttctac    420
cccaaggata tcaacgtgaa gtggaagatc gacggcagcg agcggcagaa tggcgtgctg    480
aactcctgga ccgaccagga cagcaaggac tccaccctat tccatgtcct cacccctgacc   540 ctgaccaagg atgagtacga gcggcacaac agctatacct gtgaggccac ccacaagacc    600
tccacctccc ccatcgtgaa gtccttcaat aggaatgagt gc                        642

<210> SEQ ID NO 56
<211> LENGTH: 444
<212> TYPE: PRT
<213> ORGANISM: Artificial Sequence
<220> FEATURE:
<223> OTHER INFORMATION: synthetic polypeptide

<400> SEQUENCE: 56

Glu Val Met Leu Val Glu Ser Gly Gly Gly Leu Val Gln Pro Gly Gly
1               5                  10                  15

Ser Arg Arg Leu Ser Cys Ala Ala Ser Gly Phe Thr Phe Ser Ser Tyr
            20                  25                  30

Pro Met Phe Trp Val Arg Gln Thr Pro Glu Lys Arg Met Glu Trp Val
        35                  40                  45

Ala Tyr Ile Ser Asn Gly Gly Asp Ser Thr Tyr Tyr Pro Asp Thr Val
    50                  55                  60

Lys Gly Arg Phe Thr Val Ser Arg Asp Asn Ala Lys Asn Thr Leu Tyr
65                  70                  75                  80

Leu Gln Met Ser Ser Leu Lys Ser Val Asp Thr Ala Ile Tyr Tyr Cys
                85                  90                  95

Val Arg Pro Ser Ala Arg Tyr Asp Glu Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
            290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
            325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
            370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
            435                 440

<210> SEQ ID NO 57
<211> LENGTH: 1332
<212> TYPE: DNA
<213> ORGANISM: Artificial Sequence
<220> FEATURE:
<223> OTHER INFORMATION: synthetic polynucleotide

<400> SEQUENCE: 57
gaggtgatgc tggtggagag cggcggcggc ctggtgcagc ccggcggcag caggaggctg      60
agctgcgccg ccagcggctt caccttcagc agctacccca tgttctgggt gaggcagacc     120
cccgagaaga ggatggagtg ggtggcctac atcagcaacg gcggcgacag cacctactac     180
cccgacaccg tgaagggcag gttcaccgtg agcagggaca cgccaagaa caccctgtac     240 ctgcagatga gcagcctgaa gagcgtggac accgccatct actactgcgt gaggcccagc     300
gccaggtacg acgagtggtt cgcctactgg ggccagggca ccctggtgac cgtgagcagc     360
gccaagacca cccccccag cgtgtacccc ctggccccg gcagcgccgc ccagaccaac     420
agcatggtga ccctgggctg cctggtgaag ggctacttcc ccgagcccgt gaccgtgacc     480
tggaacagcg gcagcctgag cagcggcgtg cacaccttcc ccgccgtgct gcagagcgac     540

```
ctgtacaccc tgagcagcag cgtgaccgtg cccagcagca cctggcccag cgagaccgtg      600
acctgcaacg tggcccaccc cgccagcagc accaaggtgg acaagaagat cgtgcccagc      660
gactgcggct gcaagccctg catctgcacc gtgcccgagg tgagcagcgt gttcatcttc      720
ccccccaagc caaggacgt gctgaccatc accctgaccc ccaaggtgac ctgcgtggtg      780
gtggacatca gcaaggacga ccccgaggtg cagttcagct ggttcgtgga cgacgtggag      840
gtgcacaccg cccagaccca gcccaggag gagcagttca cagcaccttc aggagcgtg      900 agcgagctgc ccatcatgca ccaggactgg ctgaacggca aggagttcaa gtgcagggtg      960
aacagcgccg ccttccccgc ccccatcgag aagaccatca gcaagaccaa gggcaggccc     1020 aaggccccc aggtgtacac catcccccc cccaaggagc agatggccaa ggacaaggtg     1080
agcctgacct gcatgatcac cgacttcttc ccgaggaca tcaccgtgga gtggcagtgg     1140
aacggccagc ccgccgagaa ctacaagaac acccagccca tcatggacac cgacggcagc     1200
tacttcgtgt acagcaagct gaacgtgcag aagagcaact gggaggccgg caacaccttc     1260
acctgcagcg tgctgcacga gggcctgcac aaccaccaca ccgagaagag cctgagccac     1320
agccccggca ag                                                         1332
```

<210> SEQ ID NO 58
<211> LENGTH: 202
<212> TYPE: PRT
<213> ORGANISM: Homo sapiens

<400> SEQUENCE: 58

```
Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200
```

<210> SEQ ID NO 59
<211> LENGTH: 202

<212> TYPE: PRT
<213> ORGANISM: Artificial Sequence
<220> FEATURE:
<223> OTHER INFORMATION: synthetic polypeptide

<400> SEQUENCE: 59

```
Met Lys Val Leu Ala Ala Gly Val Val Pro Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
        50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Thr Tyr Lys
            180                 185                 190

Gln Val Ile Ser Val Val Gln Ala Phe
        195                 200
```

<210> SEQ ID NO 60
<211> LENGTH: 202
<212> TYPE: PRT
<213> ORGANISM: Artificial Sequence
<220> FEATURE:
<223> OTHER INFORMATION: synthetic polypeptide

<400> SEQUENCE: 60

```
Met Lys Val Leu Ala Ala Gly Val Val Pro Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
        50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125
```

```
Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Pro Pro Val Pro Asp His Ser Asp Lys Glu
                165                 170                 175

Ala Phe Gln Arg Lys Lys Leu Gly Cys Gln Leu Leu Gly Thr Tyr Lys
            180                 185                 190

Gln Val Ile Ser Val Val Val Gln Ala Phe
            195                 200

<210> SEQ ID NO 61
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 61

Thr Tyr Gly Pro Asp Thr Ser Gly Lys Asp Val Phe Gln Lys Lys
1               5                   10                  15

<210> SEQ ID NO 62
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 62

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 63
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 63
caggtgcagc tgcaggagag cggcggcggc ctggtgaagc ccggcggcag cctgaggctg      60
agctgcgccg ccagcggctt caccttcagc cacgcctgga tgcactgggt gaggcaggcc     120
cccggcaagg gcctggagtg ggtgggccag atcaaggcca gagcgacga ctacgccacc      180 tactacgccg agagcgtgaa gggcaggttc accatcagca gggacgacag caagaacacc     240
ctgtacctgc agatgaacag cctgaagacc gaggacaccg ccgtgtacta ctgcacctgc     300
tgggagtggg acctggactt ctggggccag ggcaccatgg tgaccgtgag cagcgccagc     360
accaagggcc ccagcgtgtt ccccctggcc ccagcagca gagcaccag cggcggcacc       420 gccgccctgg gctgcctggt gaaggactac ttccccgagc ccgtgaccgt gagctggaac     480
agcggcgccc tgaccagcgg cgtgcacacc ttccccgccg tgctgcagag cagcggcctg     540
tacagcctga gcagcgtggt gaccgtgccc agcagcagcc tgggcaccca gacctacatc     600
tgcaacgtga accacaagcc cagcaacacc aaggtggaca gagggtggag gccaagagc      660 tgcgacaaga cccacacctg cccccccctgc ccgccccccg agctgctggg cggccccagc    720
gtgttcctgt tccccccaa gcccaaggac accctgatga tcagcaggac ccccgaggtg     780

-continued

```
acctgcgtgg tggtggacgt gagccacgag gaccccgagg tgaagttcaa ctggtacgtg    840
gacggcgtgg aggtgcacaa cgccaagacc aagcccaggg aggagcagta caacagcacc    900
tacagggtgg tgagcgtgct gaccgtgctg caccaggact ggctgaacgg caaggagtac    960
aagtgcaagg tgagcaacaa ggccctgccc gcccccatcg agaagaccat cagcaaggcc   1020
aagggccagc ccagggagcc ccaggtgtac accctgcccc cagcaggga ggagatgacc    1080 aagaaccagg tgagcctgac ctgcctggtg aagggcttct accccagcga catcgccgtg   1140
gagtgggaga gcaacggcca gcccgagaac aactacaaga ccaccccccc cgtgctggac   1200
agcgacggca gcttcttcct gtacagcaag ctgaccgtgg acaagagcag gtggcagcag   1260
ggcaacgtgt tcagctgcag cgtgatgcac gaggccctgc acaaccacta cacccagaag   1320
agcctgagcc tgagccccgg caag                                          1344
```

<210> SEQ ID NO 64
<211> LENGTH: 220
<212> TYPE: PRT
<213> ORGANISM: Artificial Sequence
<220> FEATURE:
<223> OTHER INFORMATION: synthetic polypeptide

<400> SEQUENCE: 64

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Leu Asp Ser
            20                  25                  30

Asp Gly His Thr Tyr Leu Asn Trp Leu Gln Gln Arg Pro Gly Gln Pro
        35                  40                  45

Pro Arg Leu Leu Ile Tyr Ser Val Ser Asn Leu Glu Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Ala Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 65
<211> LENGTH: 660
<212> TYPE: DNA
<213> ORGANISM: Artificial Sequence
<220> FEATURE:

<223> OTHER INFORMATION: synthetic polynucleotide

<400> SEQUENCE: 65

```
gacatcgtga tgacccagac cccctgagc agccccgtga ccctgggcca gcccgccagc    60
atcagctgca ggagcagcca gagcctgctg gacagcgacg gccacaccta cctgaactgg   120
ctgcagcaga ggcccggcca gccccccagg ctgctgatct acagcgtgag caacctggag   180
agcggcgtgc ccgacaggtt cagcggcagc ggcgccggca ccgacttcac cctgaagatc   240
agcagggtgg aggccgagga cgtgggcgtg tactactgca tgcaggccac ccacgccccc   300
ccctacacct tcggccaggg caccaagctg gagatcaaga ggaccgtggc cgcccccagc   360
gtgttcatct ccccccccag cgacgagcag ctgaagagcg gcaccgccag cgtggtgtgc   420
ctgctgaaca acttctaccc cagggaggcc aaggtgcagt ggaaggtgga caacgccctg   480
cagagcggca cagccagga gagcgtgacc gagcaggaca gcaaggacag cacctacagc   540
ctgagcagca ccctgaccct gagcaaggcc gactacgaga agcacaaggt gtacgcctgc   600
gaggtgaccc accagggcct gagcagcccc gtgaccaaga gcttcaacag gggcgagtgc   660
```

<210> SEQ ID NO 66
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 66

Lys Ala Ser Gln Asp Val Ser Asn Ala Val Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 67

Trp Ala Ser Phe Arg His Thr
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 68

Gln Gln His Tyr Asn Thr Pro Tyr Thr
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 69

Ser Tyr Pro Met Phe
1               5

-continued

```
<210> SEQ ID NO 70
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 70

Tyr Ile Ser Asn Gly Gly Asp Ser Thr Tyr Tyr Pro Asp Thr Val Lys
1               5                   10                  15
Gly

<210> SEQ ID NO 71
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 71

Pro Ser Ala Arg Tyr Asp Glu Trp Phe Ala Tyr
1               5                   10

<210> SEQ ID NO 72
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 72
gacatcgtga tgacccagtc ccacaagttc atgagcacca gcgtgggcga tcgggtgtcc      60
atcacctgta aggcctccca ggacgtgagc aacgccgtgg cctggtatca gcagaagcct     120
ggccagtccc ctcggctgct gatctattgg gcttccttca gcacaccgg cgtgcccgat      180 cggttcaccg gctccggatc cggcaccgag tataccctga ccatctcccg ggtgcaggcc     240
gaggatctgg ctctgtatta ttgtcagcag cactacaata ccccctacac cttcggcggc     300
ggcaccaggc tggagatcaa g                                                321

<210> SEQ ID NO 73
<211> LENGTH: 360
<212> TYPE: DNA
<213> ORGANISM: Artificial Sequence
<220> FEATURE:
<223> OTHER INFORMATION: synthetic polynucleotide

<400> SEQUENCE: 73
gaggtgatgc tggtggagag cggcggcggc ctggtgcagc ctggaggatc tcggaggctg      60
agctgtgccg ccagcggctt caccttctcc tcctatccca tgttctgggt gaggcagacc     120
cccgagaagc ggatggagtg ggtggcctat atctccaatg gcggcgattc cacctattat     180
cctgacaccg tgaagggccg gttcaccgtg agcggata cgccaagaa taccctgtac        240 ctgcagatga gcagcctgaa gtccgtggac accgctatct actattgcgt gaggccctcc     300
gctcggtacg acgagtggtt cgcctattgg ggccagggca ccctggtgac agtgagcgct     360

<210> SEQ ID NO 74
<211> LENGTH: 109
<212> TYPE: PRT
<213> ORGANISM: Artificial Sequence
<220> FEATURE:
<223> OTHER INFORMATION: synthetic polypeptide
```

<400> SEQUENCE: 74

Asp Ile His Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Leu
                85                  90                  95

Thr Phe Gly Ala Gly Thr Lys Leu Glu Leu Lys Arg Ala
            100                 105

<210> SEQ ID NO 75
<211> LENGTH: 117
<212> TYPE: PRT
<213> ORGANISM: Artificial Sequence
<220> FEATURE:
<223> OTHER INFORMATION: synthetic polypeptide

<400> SEQUENCE: 75

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser Tyr
            20                  25                  30

Ala Met Ser Trp Val Arg Gln Ser Pro Glu Thr Arg Leu Glu Trp Val
        35                  40                  45

Ala Thr Ile Ser Ser Gly Gly Ser Asn Thr Tyr Ser Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Tyr Tyr Gly Tyr Tyr Phe Asp Phe Trp Gly Gln Gly Thr Thr
            100                 105                 110

Leu Thr Val Ser Ser
        115

<210> SEQ ID NO 76
<211> LENGTH: 327
<212> TYPE: DNA
<213> ORGANISM: Artificial Sequence
<220> FEATURE:
<223> OTHER INFORMATION: synthetic polynucleotide

<400> SEQUENCE: 76
gacatccaca tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcagctcct ggtctataat gcaaaaacct tagcagaagg tgtgccatca     180
aggttcagtg gcagtggatc aggcacacag ttttctctga gatcaacag cctgcagcct      240 gaagattttg ggagttatta ctgtcaacat cattatgtta ctccgctcac gttcggtgct     300
gggaccaagc tggagctgaa acgggct                                         327

<210> SEQ ID NO 77
<211> LENGTH: 351
<212> TYPE: DNA
<213> ORGANISM: Artificial Sequence
<220> FEATURE:
<223> OTHER INFORMATION: synthetic polynucleotide

<400> SEQUENCE: 77

```
gaagtgatgc tggtggagtc tgggggaggc ttagtgaagc ctggagggtc cctgaaactc      60
tcctgtgcag cctctggatt cattttcagt agttatgcca tgtcttgggt tcgccagagt     120
ccggagacga ggctggagtg ggtcgcaacc attagtagtg gtggtagtaa cacctactct     180
ccagacagtg tgaaggggcg attcaccatc tccagagaca atgccaagaa caccctgtac     240
ctgcaaatga gcagtctgag gtctgaggac acggccatgt attactgtgc aagatattat     300
ggttactact ttgacttctg gggccaaggc accactctca cagtctcctc a              351
```

<210> SEQ ID NO 78
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 78

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met His Trp Val Arg Gln Ala Pro Gly Lys Gly Leu Glu Trp Val
        35                  40                  45

Gly Gln Ile Lys Ala Lys Ser Asp Asp Tyr Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Cys Trp Glu Trp Asp Leu Asp Phe Trp Gly Gln Gly Thr
            100                 105                 110

Met Val Thr Val Ser Ser
        115

<210> SEQ ID NO 79
<211> LENGTH: 116
<212> TYPE: PRT
<213> ORGANISM: Artificial Sequence
<220> FEATURE:
<223> OTHER INFORMATION: synthetic polypeptide

<400> SEQUENCE: 79

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Leu Asp Ser
            20                  25                  30

Asp Gly His Thr Tyr Leu Asn Trp Leu Gln Gln Arg Pro Gly Gln Pro
        35                  40                  45

Pro Arg Leu Leu Ile Tyr Ser Val Ser Asn Leu Glu Ser Gly Val Pro
    50                  55                  60

Asp Arg Phe Ser Gly Ser Gly Ala Gly Thr Asp Phe Thr Leu Lys Ile

```
                65                  70                  75                  80
Ser Arg Val Glu Ala Glu Asp Val Gly Val Tyr Tyr Cys Met Gln Ala
                    85                  90                  95

Thr His Ala Pro Pro Tyr Thr Phe Gly Gln Gly Thr Lys Leu Glu Ile
                    100                 105                 110

Lys Arg Thr Val
        115

<210> SEQ ID NO 80
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 80
caggtgcagc tgcaggagag cggcggcggc ctggtgaagc ccggcggcag cctgaggctg      60
agctgcgccg ccagcggctt caccttcagc cacgcctgga tgcactgggt gaggcaggcc    120
cccggcaagg gcctggagtg ggtgggccag atcaaggcca gagcgacga ctacgccacc     180 tactacgccg agagcgtgaa gggcaggttc accatcagca gggacgacag caagaacacc    240
ctgtacctgc agatgaacag cctgaagacc gaggacaccg ccgtgtacta ctgcacctgc    300
tgggagtggg acctggactt ctggggccag ggcaccatgg tgaccgtgag cagc          354

<210> SEQ ID NO 81
<211> LENGTH: 348
<212> TYPE: DNA
<213> ORGANISM: Artificial Sequence
<220> FEATURE:
<223> OTHER INFORMATION: synthetic polynucleotide

<400> SEQUENCE: 81
gacatcgtga tgacccagac cccccctgagc agccccgtga ccctgggcca gcccgccagc    60
atcagctgca ggagcagcca gagcctgctg gacagcgacg gccacaccta cctgaactgg   120
ctgcagcaga ggcccggcca gccccccagg ctgctgatct acagcgtgag caacctggag   180
agcggcgtgc ccgacaggtt cagcggcagc ggcgccggca ccgacttcac cctgaagatc    240
agcagggtgg aggccgagga cgtgggcgtg tactactgca tgcaggccac ccacgccccc    300
ccctacacct tcggccaggg caccaagctg gagatcaaga ggaccgtg                348

<210> SEQ ID NO 82
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 82

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Asn Ala
                20                  25                  30

Val Ala Trp Tyr Gln Gln Lys Pro Gly Gln Ser Pro Arg Leu Leu Ile
            35                  40                  45

Tyr Trp Ala Ser Phe Arg His Thr Gly Val Pro Asp Arg Phe Thr Gly
        50                  55                  60

Ser Gly Ser Gly Thr Glu Tyr Thr Leu Thr Ile Ser Arg Val Gln Ala
65                  70                  75                  80
```

Glu Asp Leu Ala Leu Tyr Tyr Cys Gln Gln His Tyr Asn Thr Pro Tyr
                85                  90                  95

Thr Phe Gly Gly Gly Thr Arg Leu Glu Ile Lys
            100                 105

<210> SEQ ID NO 83
<211> LENGTH: 120
<212> TYPE: PRT
<213> ORGANISM: Artificial Sequence
<220> FEATURE:
<223> OTHER INFORMATION: synthetic polynucleotide

<400> SEQUENCE: 83

Glu Val Met Leu Val Glu Ser Gly Gly Leu Val Gln Pro Gly Gly
1               5                   10                  15

Ser Arg Arg Leu Ser Cys Ala Ala Ser Gly Phe Thr Phe Ser Ser Tyr
                20                  25                  30

Pro Met Phe Trp Val Arg Gln Thr Pro Glu Lys Arg Met Glu Trp Val
            35                  40                  45

Ala Tyr Ile Ser Asn Gly Gly Asp Ser Thr Tyr Tyr Pro Asp Thr Val
        50                  55                  60

Lys Gly Arg Phe Thr Val Ser Arg Asp Asn Ala Lys Asn Thr Leu Tyr
65                  70                  75                  80

Leu Gln Met Ser Ser Leu Lys Ser Val Asp Thr Ala Ile Tyr Tyr Cys
                85                  90                  95

Val Arg Pro Ser Ala Arg Tyr Asp Glu Trp Phe Ala Tyr Trp Gly Gln
            100                 105                 110

Gly Thr Leu Val Thr Val Ser Ala
        115                 120

<210> SEQ ID NO 84
<211> LENGTH: 3692
<212> TYPE: DNA
<213> ORGANISM: Artificial Sequence
<220> FEATURE:
<223> OTHER INFORMATION: LIF encoding sequence

<400> SEQUENCE: 84
atgaacctct gaaaactgcc ggcatctgag gtttcctcca aggccctctg aagtgcagcc      60
cataatgaag tcttggcgg cagtacacag cccaggggga gccgttcccc aacaacctgg     120
acaagctatg tggccccaac gtgacggact cccgccctt ccacgccaac ggcacggaga     180
aggccaagct ggtggagctg taccgcatag tcgtgtacct tggcacctcc ctgggcaaca    240
tcacccggga ccagaagatc ctcaacccca gtgccctcag cctccacagc aagctcaacg    300
ccaccgccga catcctgcga ggcctcctta gcaacgtgct gtgccgcctg tgcagcaagt    360
accacgtggg ccatgtggac gtgacctacg ccctgacac tcgggtaag gatgtcttcc      420 agaagaagaa gctgggctgt caactcctgg ggaagtataa gcagatcatc gccgtgttgg    480
cccaggcctt ctagcaggag gtcttgaagt gtgctgtgaa ccgagggatc tcaggagttg    540
ggtccagatg tgggggcctg tccaagggtg gctgggccc agggcatcgc taaacccaaa     600
tgggggctgc tggcagaccc cgagggtgcc tggccagtcc actccactct gggctgggct    660
gtgatgaagc tgagcagagt ggaaacttcc atagggaggg agctagaaga aggtgcccct    720
tcctctggga gattgtggac tggggagcgt gggctggact tctgcctcta cttgtccctt    780
tggccccttg ctcactttgt gcagtgaaca aactacacaa gtcatctaca agagccctga    840

```
ccacagggtg agacagcagg gcccagggga gtggaccagc ccccagcaaa ttatcaccat    900
ctgtgccttt gctgcccctt aggttgggac ttaggtgggc cagaggggct aggatcccaa    960
aggactcctt gtcccctaga agtttgatga gtggaagata gagaggggcc tctgggatgg   1020
aaggctgtct tcttttgagg atgatcagag aacttgggca taggaacaat ctggcagaag   1080
tttccagaag gaggtcactt ggcattcagg ctcttgggga ggcagagaag ccaccttcag   1140
gcctgggaag gaagacactg ggaggaggag aggcctggaa agctttggta ggttcttcgt   1200
tctcttcccc gtgatcttcc ctgcagcctg ggatggccag ggtctgatgg ctggacctgc   1260
agcaggggtt tgtggaggtg ggtagggcag gggcaggttg ctaagtcagg tgcagaggtt   1320
ctgagggacc caggctcttc ctctgggtaa aggtctgtaa gaaggggctg gggtagctca   1380
gagtagcagc tcacatctga ggccctggga ggccttgtga ggtcacacag aggtacttga   1440
gggggactgg aggccgtctc tggtccccag ggcaagggaa cagcagaact tagggtcagg   1500
gtctcaggga accctgagct ccaagcgtgc tgtgcgtctg acctggcatg atttctattt   1560
attatgatat cctatttata ttaacttatt ggtgctttca gtggccaagt taattcccct   1620
ttccctggtc cctactcaac aaaatatgat gatggctccc gacacaagcg ccagggccag   1680
ggcttagcag ggcctggtct ggaagtcgac aatgttacaa gtggaataag ccttacgggt   1740
gaagctcaga gaagggtcgg atctgagaga atggggaggc ctgagtggga gtgggggggcc  1800
ttgctccacc cccccccatc ccctactgtg acttgcttta gggtgtcagg gtccaggctg   1860
caggggctgg gccaatttgt ggagaggccg ggtgcctttc tgtcttgatt ccaggggggct  1920
ggttcacact gttcttgggc gccccagcat tgtgttgtga ggcgcactgt tcctggcaga   1980
tattgtgccc cctggagcag tgggcaagac agtccttgtg gcccaccctg tccttgtttc   2040
tgtgtcccca tgctgcctct gaaatagcgc cctggaacaa ccctgcccct gcacccagca   2100
tgctccgaca cagcagggaa gctcctcctg tggcccggac acccatagac ggtgcggggg   2160
gcctggctgg gccagacccc aggaaggtgg ggtagactgg ggggatcagc tgcccattgc   2220
tcccaagagg aggagaggga ggctgcagat gcctgggact cagaccagga agctgtgggc   2280
cctcctgctc cacccccatc ccactcccac ccatgtctgg gctcccaggc agggaacccg   2340
atctcttcct ttgtgctggg gccaggcgag tggagaaacg ccctccagtc tgagagcagg   2400
ggagggaagg aggcagcaga gttggggcag ctgctcagag cagtgttctg gcttcttctc   2460
aaaccctgag cgggctgccg gcctccaagt tcctccgaca agatgatggt actaattatg   2520
gtacttttca ctcactttgc acctttccct gtcgctctct aagcacttta cctggatggc   2580
gcgtgggcag tgtgcaggca ggtcctgagg cctggggttg gggtggaggg tgcggcccgg   2640
agttgtccat ctgtccatcc caacagcaag acgaggatgt ggctgttgag atgtgggcca   2700
cactcacccct tgtccaggat gcagggactg ccttctcctt cctgcttcat ccggcttagc   2760
ttggggctgg ctgcattccc ccaggatggg cttcgagaaa gacaaacttg tctgaaaacc   2820
agagttgctg attccacccg gggggccggg ctgactcgcc catcacctca tctccctgtg   2880
gacttgggag ctctgtgcca ggccaccttt gcggccctgg ctctgagtcg ctctcccacc   2940
cagcctggac ttggccccat gggacccatc ctcagtgctc cctccagatc ccgtccggca   3000
gcttggcgtc caccctgcac agcatcactg aatcacagag cctttgcgtg aaacagctct   3060
gccaggccgg gagctgggtt tctcttcct ttttatctgc tggtgtggac cacacctggg    3120
cctgccggga ggaagagaga gtttaccaag agagatgtct ccgggccctt atttattatt   3180
taaacatttt tttaaaaagc actgctagtt tacttgtctc tcctccccat cgtccccatc   3240
```

```
gtcctccttg tccctgactt ggggcacttc caccctgacc cagccagtcc agctctgcct      3300
tgccggctct ccagagtaga catagtgtgt ggggttggag ctctggcacc cggggaggta      3360
gcatttccct gcagatggta cagatgttcc tgccttagag tcatctctag ttccccacct      3420
caatcccggc atccagcctt cagtcccgcc cacgtgctag ctccgtgggc ccaccgtgcg      3480
gccttagagg tttccctcct tcctttccac tgaaaagcac atggccttgg gtgacaaatt      3540
cctctttgat gaatgtaccc tgtggggatg tttcatactg acagattatt tttatttatt      3600
caatgtcata tttaaaatat ttattttttta taccaaatga atactttttt ttttaagaaa      3660
aaaaagagaa atgaataaag aatctactct tg                                    3692
```

<210> SEQ ID NO 85
<211> LENGTH: 4114
<212> TYPE: DNA
<213> ORGANISM: Artificial Sequence
<220> FEATURE:
<223> OTHER INFORMATION: mouse LIF encoding sequence

<400> SEQUENCE: 85

```
atggtccggg caccgcgcgc ccagcccgcc ggggccagca ggttggcggt gagggacctg        60
gccggcgtag ccttgctcca ccgccttctc tcctcgcccc actgctctcc tgtgctgctc       120
ttacttctcc gctgtcgcct agatttaccc tccctctttc ttttctttc tttccgcttt        180 ctcttttcca actgcgtccc gggctgctcc ctgggagggg cgcaggcggc tgagcagctt       240
gcaaactccg gccaggaccg cgcaggtgc ggcttccgtc tgctagtccc tggaaagctg        300
tgattggcgc gagatgagat gcagggattg tgcccttact gctgctggtt ctgcactgga       360
aacacggggc agggagccct cttcccatca cccctgtaaa tgccacctgt gccatacgcc       420
acccatgcca cggcaacctc atgaaccaga tcaagaatca actggcacag ctcaatggca       480
gcgccaatgc tctcttcatt tcctattaca cagctcaagg ggagccgttt cccaacaacg       540
tggaaaagct atgtgcgcct aacatgacag acttcccatc tttccatggc aacgggacag       600
agaagaccaa gttggtggag ctgtatcgga tggtcgcata cctgagcgcc tccctgacca       660
atatcacccg ggaccagaag gtcctgaacc ccactgccgt gagcctccag gtcaagctca       720
atgctactat agacgtcatg aggggcctcc tcagcaatgt gctttgccgt ctgtgcaaca       780
agtaccgtgt gggccacgtg gatgtgccac ctgtccccga ccactctgac aaagaagcct       840
tccaaaggaa aaagttgggt tgccagcttc tgggacata caagcaagtc ataagtgtgg        900
tggtccaggc cttctagaga ggaggtcttg aatgtaccat ggactgaggg acctcaggag       960
caggatccgg aggtggggag ggggctcaaa atgtgctggg gtttgggaca ttgttaaatg      1020
caaaacgggc tgctggcag accccaggga tttccaggta ctcactgcac tctgggctgg       1080
gccatgatgg aatctggcaa agttgaaact tccataggca gagcttctat acagcccagc     1140
accagctaga aatggcaatg agggtgttgg tctgagagat ttctgtctca ctcactcact      1200
cactcactct cactcactca ctcactcact cactcagccc cttgcttgct gggtgtatga      1260
acaagctgca caagttgtct acagcagaca gcaaagggct gggaagtgtc ctagacccct      1320
acagagtcac catcatctgg tcctttgctg tctctcagag aaactttgga aggcttggtt      1380
gggatgtgag agagctaagg ggactgggat ccagaaggaa tccttttatt ttatttttatt    1440 ttattttatt ttattttatt ttataagttt tgtgggtgga agggtaccct ggggtggaat      1500 gatgaatgt gtcttctctt gagttggatg agagagttca ggcttagaga ctgtcagatg       1560
```

```
gaagagtcta ggtcaccagt gttcaggctc ccacagaagc acagcggcca gcttccagtt   1620
gtcaaagcct gacgaactcg gttagcttct atgcagttcc ccccacagcc tggcgtggtt   1680
ggggtctgcc agctggacct agaggtgagg tgtgtgcagg caggaagagg caggctgcaa   1740
aggcaggttc ccagagtcct cccggggaag gacctctaac tgtctaggag tcagggaagg   1800
agcaaggcag ccagccattg ctgaggcagt agccgactgc agctctcatc tgcttctcaa   1860
cccctgagaa caggtgatct tgagcagaca gacaggtagc ataaagtaga atgtcgggtc   1920
tgaggccccg gaggtcgcaa aggtacttga aggggaccag agggctgtct tgggtccctg   1980
gagcatggag aagcagaact tgaggtcagg gtctcaggga agatgaggcc cagagtgctg   2040
tgtttgatcc agcacagctg tctatttatt actatgtcct atttatatta acttattggt   2100
gctttaaatg gcaaagttaa ttccccgaaa tggtatgagg ctccttccat gggagctggg   2160
gccgagactc tccacctagt ggggcctggt ctggaggcac atgattgtta caggtgcagc   2220
tcatgggtca aatcagagag ctggctagct cctctgtctc ccactgtgac tcacttttag   2280
ggtgtcaggg tcccccagaa aaagctgggc cagtttgtct ctctgcttct gtctctgtct   2340
ctccgagtct gtctctgtct gtctctgtgt ctctgtctct ttgtctctct ctgtctctgt   2400
ctctctctct ctctccccgc ccccccccct tctccctctg gtctccaagg gggtggaaca   2460
gtttcttgtt gttttgtccc actgagctct ctggcacccc ctagattcct gctatgcggt   2520
gcaccattca taatgaagtg aatggctctg gaaccttggg caaaactgat tccttcctca   2580
aatcgtagct gaggagtgct gaaacatcct gacccggcac ccagcgtgct ttcgaccagc   2640
atggaagctc ctcgggtggc ccgaacaccc acagagggtg aatacaggag gttggagcag   2700
tgcaggccct gaactgggcc tgaacagctg cccagtgcgc cagagaaggg gagatcaagg   2760
cccgagacgc ctgggacaca gaccaggaag ctgtggtcct tgcttcatcg ctgccttccc   2820
actcccgccc atgtctgggc tcccaggcag ggaatccgat ctgatctctc ctttgtgctg   2880
aggccaggca agcagaggaa cgccctcgat ctgggagcag ggtagggagg aaggcagcca   2940
agctggggca gtggctgact acagagctag ctgcctgcct ctcaggctct gaacagggcg   3000
gtccttagca gttcagcagt gggattctgc ttcacgcggt tttgcacctt tctctgtcac   3060
tctctaagca cttacctgg acggcaggtg gacaggccct ggagctctgg cttaggaaag   3120
gcctggaacc atagatgcag caaggagact atggtggggg ccacgcgtgt cagcgacaaa   3180
gttactccac cgtactcctg ttgctgcgtc aggctcatct caggactggc tgcccttctc   3240
caagctgaga gtcaatttgt ctaaaagcca agatgatgcc acagcctggg gcctgttggg   3300 cttttgtcatc acttcacatt tgtatggact tggactctct gggctccgcc cacctggcag   3360
ctttgaaggc tcagggacca atggactctc tccgtgcacg cccccgtccc cccaacgcaa   3420
ccacctacct gcgtcttact ccatcagttg cccagcatcc cagaaccatt gagcctttgg   3480
ggaaaacaga cttttagggg caggtagttgc tcacctgaca tctttcacct ggaagcattg   3540
acttccaccg agcatagtag gtagtgtgtc tggaccagag aaaaagggat ggggcatttt   3600
gcagtttatc cagagagaag caaaggggcc tttatttatt atttaaaact tcaaacctga   3660
aagcactgag agtttactgg tctgcccccc tcccccccact cttgtctatt tctgtgtcct   3720
tgatcccgac tcaagcaacc cagctctgct ttgcctgctc tctggagcag acatggtatg   3780
tgggccagga ccccggagtc ttgcatggta gcggcttcag aagggaaatg atatggctgt   3840
ctgcattcgg atgactcccc agtcccagcc cagcctctcc tttgcactgc tgctctccct   3900 cttttccttcc ctttggaagg gacttggcct tgggtgacaa attcctcttt gatgaatgta   3960
```

```
ccctgtggga atgtttcata ctgacagatt attttattt attcaatgtc atatttaaaa    4020
tatttatttt ttatactgaa ggagtgtctt tttttttaa agaaaaaatg aaataataaa     4080
gaactcattc ttgttgaaaa aaaaaaaaaa aaaa                                4114
```

<210> SEQ ID NO 86
<211> LENGTH: 6393
<212> TYPE: DNA
<213> ORGANISM: Artificial Sequence
<220> FEATURE:
<223> OTHER INFORMATION: machin LIF encoding sequence

<400> SEQUENCE: 86

```
gggggttggag ggtgaggagc agcgattgtt ggagacacac gccggggcac acgcaggcct    60
ggaggctcag aaatgcacgc gtgcacgccc agggttagac cgccttgctc acctagccct   120
cgtgcccagg atccacagt cccacacaaa ctcaggcaga cacgaggcca gacacacagt    180
cgcactggct tcatgcccat gggcacgtgt gcacacaaac acacacacag acacactcac    240
acaaccacac ggacaactca caatagcagc cagagatgtg caccatctag ctctcagtca    300
cacaaagcaa aaggtacaag cagatctaca cacgtgaaca cacttgcaca caccacacat    360
gcacacacgg taccagacac aggcatgcac agacacagag gcactcacta cacacgcatg    420
ctcaggcaaa tgcccactca gactcggaca gacagacaga caaacacact cagccacgtc    480
ccagggccac agggagccca agtgtgcgcc ctctactgca ggctggggct cttggcctca    540
ggctgccctg gaaggtggc tgtggccact tcctcttccc gcaccctgcg gtgaggatga    600
aaggctccct ggtggagtag gaaagaaagg cctgtgactg tcctgggctc cacccaggtg    660
ggatggggca gggcagagag cccaggggtc tgaggctgcg gaagggagtg gacagtgagc    720
ggctgggctc tgggaggcct ttgtcacggc acagggtgcc accaggtccc ctacgttgag    780
cacctgctca gccctgcccc gtcctaccct gcggcacctc tggcccattc cagagctgga    840
agggaagtca ggagccccgt gagacactgc tgagtgacct tgggcaagtc actcctcagc    900
ccctctgggc ctggctttca acatcgatac cagcggcttg caaatgtttt tgactgccac    960
ccacagtaag aaatacattg caccttgcaa ccagatgagg atgcagatac tgacacacac   1020
aggcaaccgg aaaaaaagtt tcatggagcg atcctcgccc tggctctggg cgatgccagg   1080
tgatttcgct attccatttc ctttttgaaa gtgttggtgg caaccctcta attgaatcca   1140
tggcccacga agaggcagag gcccgcagtg tgaaaacaca gctctctcta catctgccag   1200
caatggtctc aggctagttc gaaattcagg gagagcctgg gggaggtaaa agtgcttgca   1260
gagtctcaaa ggccatgctc acgaaatgct gatggctgag gtagacagca acccattcta   1320
cagagccctg gggggaccg gccccacgca acgccacagc caggcctctg gctggccctg    1380
ccaatgatca ggggctgctg cttcccttgc aatttctatc agaaatgaag aaaaaaaaat   1440
gcagtcactc tgattcatct caggggggtt gattcctgac acagtaggtc gggaaatgtc   1500
agggtgatga tgggagcagt tggcagaagg ccagggtggc ttctggcttc tcgttggccc   1560 tgagggggata ctgctggtcg ctgccagaga ctggatccag taagggtgag aaggggcagg   1620
cgataggccc agcatctgga cctcaagagc ccccagaaga cagctgggct ctccagggcc   1680
cagagatggg gggagtactg cttatttccc ccaccgaggc cctgagatgc tactcactct   1740
cctaaaaccc acaccagact ccattaactg agaggaccca ggagccacct cctgctctga   1800
ctctcagacc ccactgcgct gaccacggga cccagcccta acccaagccc ctgactcggt   1860
```

```
ctggggtttg agctccttct tcggccatag ccagatctta ttagaatggc tgccacacgt    1920
taggtgtttg tccacatttc ccaggaaaca tcccggtgat ggccccacaa ggctgttaca    1980
acagcatcct catttgcaga gggaaaactg aggctgtgag agaggaagcg cgttgccccg    2040
ggccacatag ctggtggttg gggcaggagg gatttgaacc cacaccctg gggtgagaac     2100 agtagaggca cggtccgctg gtggcattac actgtcactc ctcaagcatt gaagagtgtg    2160
gtgctcttgc cttttttggcc aggatgccca attggctggg ctgtgccagg cattcctgag   2220
tttccccatc tcctctggcc acccctcacc agccctgggc ctgggaccca ccctctggac    2280
cccggcttcc ttcctaggcc cacctgagga ctctgttcat tttccaggta ccagggccag    2340
aggagttggg gaaggaagga gggaggacag actgggcagc cgggggtgcc cggagcgctg    2400
tttctgggtc accggtcttg gggaattccc cagtgcccgg agagctgctt acctggctcc    2460
agtatataaa tcaggcaaat tccccatttg agcatgaacc tctgaaaact gccggcatct    2520
gaggtttcct ccaaggccct ctgaagtgca gcccataatg aaggtcttgg cggcaggagt    2580
tgtgcccctg ctgctggttc tgcactggaa acatggggca gggagcccc tcccatcac     2640 ccctgtcaac gccacctgtg ccatacgcca cccatgtcac aacaacctca tgaaccagat    2700
caggagccaa ctggcacagc tcaatggcag tgctaatgcc ctctttattc tctattacac    2760
agcccagggg gagccgttcc ccaacaacct ggacaagctg tgcggcccca acgtgacgga    2820
cttcccgccc ttcacgcca acggcacgga gaaggccaaa ctggtggagc tgtaccgcat     2880
agtcgtgtac ctcggcacct ccctgggcaa catcacccgg gaccagaaga tcctcaaccc    2940
cagtgccctc agcctccata gcaagctcaa cgccactgct gacatcctgc gaggcctcct    3000
tagcaacgtg ctgtgccgcc tgtgcagcaa gtaccacgtg ggccatgtgg acgtgaccta    3060
tggccctgac acctcgggta aggacgtttt ccagaagaag aagctgggct gtcaactcct    3120
ggggaagtat aaggagacca tcgccgtgtt ggcccaggcc ttctagcaag aggtcttgaa    3180
gcgtgctgtg aaccaaagga tctcaggagt gaggtccaga tgtgggggcc tgtcctagag    3240
tggctggggc ccagggcatg gctaaaccca atggggggct gctggcagac cccgagggtg    3300
cctggccagt ccactcccct ctgggctggg ctgtgatgaa gctgagcaga gtggaaactt    3360
ccatagggag ggagctagaa gaaggtgccc cttcctctgg gagattgtgg actggggagc    3420
gtgggctgga cttctgcctc cacttgtccc tttggcttct tgctcacttt gtgcagtggg    3480
caaactacac agtcatctac aacagccctg accacagcga gacagcaggg ccccggggag    3540
tggaccagcc cctggtaaat gatcaccatc tgtgcctttg ctgcccctta ggttgggact    3600
caggtgggcc agaggggctg gggtcccaaa ggactccttg tcccctagaa gtttgatgag    3660
tggaagatag agaggggcct ctgggatggg aggctgtctt cttttgagga tgatcagaga    3720
acttgggcat aggaacagtc aggcagaagt ttccagaagg aggtcacttg gcattcaggc    3780
tcttggggag gcaaagaagc caccttcagg cctgggaagt aagacgctgg gaggaggaga    3840
ggccccgaaa gctttggtgg gttcttcctt ctcttcctcg tgatcttcct tacagcctgg    3900
gatggccagg gtctggtggc tgaacctgca gcaggggttt gtggaggtgg gtagggcagg    3960
ggcaggttgc taagtcaggt gcagaggttc tgaaggaccc agggtcttcc tctgggtaag    4020
agtctgtaag gagggggctag ggtagctcag agtagcagct cacatctgag gccctgggag    4080
gccttgtgag gtcacacaga ggacttgag ggggaccgga ggccttctct ggtcccagg      4140 gcaaagggat agcagaactt gaggtcaggg tctcaggaa ccctgagctt caagcgtgct     4200
gtgcgtctga cccggaatga tttctatttta ttatgatatc ctatttatat taacttattg   4260
```

```
gtgctttcag tggcaaagtt aattcccctt tccctggtcc ctactcggca aaatatgatg    4320
atggttcccg acacaagcgc cagggccagg gcttagcagg gcctggtctg aaagtcgaca    4380
atgttacaag tggaataagc cttataggtg aagctcagag aagggtcgga tctgagagaa    4440
tggggaggcc tgagtgggag tgcggggcct ggctccaccc ccatccccta ctgtgacttg    4500
ctttggggtc tcagggtcca ggctgcaggg gctgggccag tttgtggaga ggccgggtgc    4560
ctttctgtct tggttccagg gggctggttc acactgttct cgggcgcccc agcgttgtgt    4620
tgcgaggagc actgctcctg gttgaaattg tgcccctgg agcagtgggc aagacagtcc    4680
ttgtggccca ccctgtccct gtttctgtgt ccccatgttg cctctgaaat agtgccctgg    4740
aacaatcctg ccccagcacc cagcgtgctc ccacgcagca gggaagctcc tccggtggcc    4800
cggacaccca tagagggtgg gggggcctgg ctgggccaga ccccaggaag gtgggggaga    4860 ctgggggat cagctgccca ctgctcccaa gaggaggaga gggaggctgc agacgcctgg    4920
gactcagacc aggaagctgt gggccctcct gccccacccc catcccactc ccacccatgt    4980
ctgggctccc aggcagggaa cccgatctct ttctttgtgc tggggccagg cgagtggaga    5040
aacgccctcc agtctgagag caggggaggg agggaggcag ccgaaccggg gcagctgctc    5100
agagcagtgt tctggcttct tctcaaaccc tgagtcgct gccggcctcc aagttcctct    5160
gacaagatga tggtactaat tatggtactt ttcactcact ttgcaccttt ccctgtcgct    5220
ctctaagcac tttacctgga tggcgcatgg gcagcgtgca ggcaggtcct gaggcctggg    5280
gttggggtgg agggtgcggc cgggagttgt ccatctgtcc gtcccaatgg caagatgagg    5340
atgtggctgt tgagattttg gccacactca cccttgtcta ggatgcaggg gccgccttcc    5400
ccttcctgct ccatctggct tagcttgggg caggctgcac tccccaaga tggacttcaa    5460 gaaagacaaa tttgcctgga aaccagagtt gctgattcca cccagtgtgc cccgctgact    5520
cacccatcac ctcatctccc tgtggacttg ggtgctctgt gccgagacca cctggcggcc    5580
ctggtggccc tggctctgag tcactctcct gcccagcctg gactcggacc catggtaccc    5640
atcctcagtg ctccctccag atcccatctg gcagctcggc atccactctg cacagcatca    5700
ctgaatcacg gagcctttgc gtgaaacagc tctgccggac caggagctga gttcctcttc    5760 ccttttatc tgctggtgcg gatcacacct gggcctggcc agaggaagag agagggacag    5820
tcattttgta gtttaccaag agagacgtct ccagctctgg gtccttattt attatttaaa    5880
cattttttta aaaagcactg ctagtttact tgtctctcct ccccatcgtc cccatcgtcc    5940
tccttgtccc tgacttgcgg cacttccacc ctgacccagc cagtccagct ctgccttgac    6000
ggctctccag agtagacata gtgtgtgggg ttggagctct ggcacccggg gaggtagcgt    6060
ttccctgcag atggtacaga tgttcctgcc ttagaatcat ctctagttcc tcaccccaat    6120
cccggcatcc agccttcagt ctcgcccacg tgctagctcc gtgggcccac cgtgcggcct    6180
tagaggtttc cctccttcct ttccactgta aagcacttgg ccttgggtga caaattcctc    6240
tttgatgaat gtaccctgtg gggatgtttc atactgacag attattttta tttattcaat    6300
gtcatattta aaatatttat tttttatacc aaatgaatac ttttttttt aagaaaaaaa    6360 gataaatgaa taaagaatct actcttggtt agc                                 6393
```